(12) United States Patent
Oohashi et al.

(10) Patent No.: US 7,851,126 B2
(45) Date of Patent: Dec. 14, 2010

(54) LITHOGRAPHIC PRINTING PLATE PRECURSOR AND LITHOGRAPHIC PRINTING PROCESS

(75) Inventors: Hidekazu Oohashi, Shizuoka (JP); Akihiro Endo, Shizuoka (JP)

(73) Assignee: Fujifilm Corporation, Tokyo (JP)

( * ) Notice: Subject to any disclaimer, the term of this patent is extended or adjusted under 35 U.S.C. 154(b) by 135 days.

(21) Appl. No.: 11/505,468

(22) Filed: Aug. 17, 2006

(65) Prior Publication Data

US 2007/0042293 A1 Feb. 22, 2007

(30) Foreign Application Priority Data

Aug. 19, 2005 (JP) ............................ P2005-238820

(51) Int. Cl.
*G03F 7/00* (2006.01)
*G03F 7/26* (2006.01)

(52) U.S. Cl. .............. 430/270.1; 430/273.1; 430/281.1; 101/453; 101/450.1

(58) Field of Classification Search .............. 430/270.1, 430/278.1, 302; 101/454
See application file for complete search history.

(56) References Cited

U.S. PATENT DOCUMENTS

| | | | |
|---|---|---|---|
| 4,854,969 A | 8/1989 | Bassemir et al. | |
| 6,399,270 B1 * | 6/2002 | Mori et al. | 430/270.1 |
| 6,806,031 B2 * | 10/2004 | Endo et al. | 430/278.1 |
| 2005/0069811 A1 * | 3/2005 | Mitsumoto et al. | 430/270.1 |
| 2006/0093974 A1 * | 5/2006 | Maskasky et al. | 430/619 |
| 2006/0216660 A1 * | 9/2006 | Oyamada et al. | 430/619 |

FOREIGN PATENT DOCUMENTS

| | | |
|---|---|---|
| EP | 0-516-372 A1 | 12/1992 |
| EP | 1-403-716 A2 | 3/2004 |
| EP | 1 493 562 A2 | 1/2005 |
| JP | 02-268144 A | 11/1990 |
| JP | 04-107569 A | 4/1992 |
| JP | 05-289413 A | 11/1993 |
| JP | 07-070361 A | 3/1995 |
| JP | 10-246956 A | 9/1998 |
| JP | 11-129639 A | 5/1999 |
| JP | 2938397 B2 | 6/1999 |
| JP | 11-288082 A | 10/1999 |
| JP | 2001-277740 A | 10/2001 |
| JP | 2001-277742 A | 10/2001 |
| JP | 2002-287334 A | 10/2002 |
| JP | 2002318452 A * | 10/2002 |
| JP | 2003-312159 A | 11/2003 |
| JP | 2004-109320 A | 4/2004 |
| JP | 2005-060332 A | 3/2005 |
| JP | 2005-119273 A | 5/2005 |
| JP | 2005-219393 A | 8/2005 |

OTHER PUBLICATIONS

Lin, Tu-Chen et al., Journal of Chinese Chemical Societu, 1995, 42, 543-546.*
Scriven et al., Chemical Review, Mar./Apr. 1988, vol. 88, No. 2, 1-72.*
Lin et al., "Reactivity of Iminophosphoranes. Formation of the Piperazine Ring", Journal of the Chinese Chemical Society, 1995, vol. 42 No. 3, pp. 543-546.
Klamann et al., "Alkylierung tertiärer Phosphine mit Sulfonsäureestern", Apr. 1964, vol. 97, pp. 2534-2538.
JP 2005-238820, Office Action with English Translation, Sep. 14, 2010.

* cited by examiner

*Primary Examiner*—Cynthia H Kelly
*Assistant Examiner*—Chanceity N Robinson
(74) *Attorney, Agent, or Firm*—Birch, Stewart, Kolasch & Birch, LLP

(57) ABSTRACT

A lithographic printing plate precursor, which comprises: a support; an image-recording layer; and a protective layer, in this order, wherein at least one of the image-recording layer and the protective layer comprises a phosphonium salt having a specific structure, and a lithographic printing process, which comprises: exposing a lithographic printing plate precursor; supplying an oil-based ink and a fountain solution comprising a phosphonium salt having a specific structure to the exposed lithographic printing plate precursor on a printing machine to remove an unexposed area of an image-recording layer; and conducting printing.

13 Claims, No Drawings

LITHOGRAPHIC PRINTING PLATE PRECURSOR AND LITHOGRAPHIC PRINTING PROCESS

BACKGROUND OF THE INVENTION

1. Field of the Invention

The present invention relates to a lithographic printing plate precursor and lithographic printing process. More particularly, the invention relates to a lithographic printing plate precursor which gives a lithographic printing plate stably showing ink receptibility during printing and having excellent printing durability, and to a lithographic printing process.

2. Description of the Related Art

A lithographic printing plate generally has oleophilic image areas which receive an ink during printing and hydrophilic nonimage areas which receive a fountain solution. Lithographic printing is a process in which the surface of a lithographic printing plate is made to have a difference in ink adhesion by forming oleophilic image areas as ink-receiving areas and hydrophilic nonimage areas as fountain-solution-receiving areas (non-ink-receiving areas) based on the fact that water has the property of repelling oil-based inks, and an ink is adhered only to the image areas and then transferred to a material to be printed, e.g., paper, to conduct printing.

A lithographic printing plate precursor (PS plate) comprising a hydrophilic support and an oleophilic photosensitive resin layer (image-recording layer) formed thereon has hitherto been in wide use for producing such lithographic printing plate therefrom. Usually, a lithographic printing plate is produced from a lithographic printing plate precursor by a method which comprises exposing the precursor through an original, e.g., a lith film, and then dissolving and removing those unnecessary parts of the image-recording layer which become nonimage areas with an alkaline developing solution or organic solvent to thereby expose the corresponding surface parts of the hydrophilic support and form nonimage areas while leaving those parts of the image-recording layer which become image areas.

Such platemaking processes heretofore in use for producing a printing plate from a lithographic printing plate precursor necessitate a step in which unnecessary parts of the image-recording layer after exposure are dissolved and removed with a developing solution or the like. However, to eliminate or simplify such a wet treatment performed additionally is one of the subjects to be accomplished. In particular, the discard of waste liquids resulting from wet treatments has recently become a matter of considerable concern of the whole industrial world from the standpoint of care of the global environment and, hence, there is an increasingly growing desire for the accomplishment of that subject.

For this purpose, a technique called on-press development has been proposed as a simple platemaking method. In this technique, an image-recording layer is used whose unnecessary parts can be removed in an ordinary printing process. After exposure, the unnecessary parts of the image-recording layer are removed on a printing machine to obtain a lithographic printing plate.

Examples of the on-press development include: a method which uses a lithographic printing plate precursor having an image-recording layer capable of being dissolved or dispersed in a fountain solution or ink solvent or in a fountain solution/ink emulsion; a method in which an image-recording layer is mechanically removed by contact with rollers or the blanket of a printing machine; and a method in which the cohesive force of an image-recording layer or adhesion between the image-recording layer and the support is reduced by the penetration of a fountain solution, ink solvent, or the like and, thereafter, the image-recording layer is mechanically removed by contact with rollers or the blanket.

In the invention, the term "development step" means, unless otherwise indicated, a step in which an apparatus (usually, an automatic processor) other than printing machines is used to remove unexposed areas of the image-recording layer of a lithographic printing plate precursor by contact with a liquid (usually, an alkaline developing solution) to expose a surface of the hydrophilic support. Furthermore, the term "on-press development" herein means, unless otherwise indicated, a method and step in which a printing machine is used to remove unexposed areas of the image-recording layer of a lithographic printing plate precursor by contact with a liquid (usually, a printing ink and/or a fountain solution) to expose a surface of the hydrophilic support.

However, in the case of using the related-art image-recording layer in which images are recorded with ultraviolet or visible light, it has been necessary to employ a troublesome procedure in which the lithographic printing plate precursor which has been exposed is, for example, kept in a completely light-shielded state or under constant-temperature conditions until it is mounted on a printing machine because the image-recording layer does not fix even after the exposure.

On the other hand, digitization technology in which image information is electronically processed, accumulated, and outputted by a computer has recently come to spread extensively, and various new image output techniques suitable for such digitization technology have come to be practically used. Under these circumstances, attention is focused on a computer-to-plate technique in which a highly convergent radiation such as a laser light is caused to carry digitized image information and this light is used to scan and expose a lithographic printing plate precursor to directly produce a lithographic printing plate without via a lith film. Consequently, to obtain a lithographic printing plate precursor suitable for such a technique has become one of important technical subjects.

As described above, simplification of platemaking and use of a dry platemaking process involving no development step have recently come to be more strongly desired than before from the standpoints of care of the global environment and suitability for digitization.

High-output lasers such as a semiconductor laser emitting infrared rays having a wavelength of from 760 to 1,200 nm and a YAG laser have recently become available at low cost. Because of this, a process for lithographic printing plate production using any of these high-output lasers as a device for image recording is coming to be regarded as a promising process which employs scanning exposure and is easy to incorporate into the digitization technology.

In the conventional platemaking process, a photosensitive lithographic printing plate precursor is imagewise exposed at a low to medium illuminance to record an image based on an imagewise property change caused by a photochemical reaction in the image-recording layer. In contrast, in the above-described process using a high-output laser, a large quantity of light energy is applied to exposed areas in an extremely short time period to efficiently convert the light energy to heat energy and the image-recording layer is caused by this heat to thermally undergo a change such as a chemical change, phase change, or change in form or structure. This change is utilized for image recording. Consequently, although image information is inputted by means of light energy such as laser light, image recording is influenced not only by the light energy but also by the reaction caused by heat energy. Usually, the recording technique utilizing the heat generated by such highpower-density exposure is called heat mode recording, and the conversion of light energy into heat energy is called light/heat conversion.

Great merits of platemaking processes employing heat mode recording are that the image-recording layer is not sensitive to light on an ordinary illuminance level, such as indoor light, and that an operation for fixing the image recorded by high-illuminance exposure is not essential. Namely, there is no possibility that the lithographic printing plate precursor for use in heat mode recording might be influenced by indoor light before exposure, and it is not essential to conduct an operation for image fixing after exposure. Consequently, when there is a lithographic printing plate precursor capable of on-press development which employs an image-recording layer which is insolubilized or solubilized by exposure with, e.g., a high-output laser, then a printing system is possible in which the image is not influenced even when the image-recording layer after the exposure is exposed to indoor ambient light. Namely, it is expected that when heat mode recording is utilized, a lithographic printing plate precursor suitable for on-press development can be obtained. However, most of the related-art photosensitive recording materials practically useful as image-recording layers are sensitive to light in the visible region having wavelengths of 760 nm and shorter and, hence, image recording therein with an infrared laser is impossible. Because of this, there is a desire for a material capable of image recording with an infrared laser.

Under these circumstances, Japanese Patent No. 2938397, for example, describes a lithographic printing plate precursor comprising a hydrophilic support and, formed thereon, an image-forming layer comprising a hydrophilic binder and hydrophobic thermoplastic-polymer particles dispersed therein. There is a description in Japanese Patent No. 2938397 to the effect that this lithographic printing plate precursor can be used in the following manner. The precursor is exposed with an infrared laser to thermally bond the hydrophobic thermoplastic-resin particles to one another and thereby form an image. Thereafter, this precursor is attached to the cylinder of a printing machine and developed thereon with a fountain solution and/or an ink.

The technique described above in which an image is formed by the mere bonding of fine particles by thermal fusion attains satisfactory on-press developability. However, this technique has had a problem that image strength (adhesion to the support) is considerably low and printing durability is insufficient.

On the other hand, JP-A-2001-277740 and JP-A-2001-277742 describe a lithographic printing plate precursor which comprises a hydrophilic support and deposited thereon microcapsules containing a polymerizable compound.

Furthermore, JP-A-2002-287334 describes a lithographic printing plate precursor comprising a support and formed thereon a photosensitive layer (image-recording layer) comprising an infrared absorber, a radical polymerization initiator, and a polymerizable compound.

Those techniques utilizing a polymerization reaction have a feature in that image strength is relatively satisfactory because the image areas have a higher chemical-bond density than the image areas formed by the thermal fusion bonding of fine polymer particles.

However, the radical polymerization type photosensitive layer has a feature in that it is apt to be influenced by oxygen during image formation. It has hence been necessary to form a protective layer comprising a hydrophilic resin having high oxygen barrier properties, such as poly(vinyl alcohol). Such a protective layer has had drawbacks that the removal thereof in on-press development requires much times to incur a large paper loss and that in case where the protective layer is not completely removed and remains in a slight amount on the image areas, then the residue attracts a hydrophilic ingredient in the fountain solution to reduce ink receptibility. The reduced ink receptibility arouses troubles, for example, that the image areas during printing come to suffer ink adhesion failures, resulting in reduced printing durability. For overcoming these drawbacks, it is effective to add a hydrophilic compound to the protective layer and the image-recording layer and thereby enhance the penetration of a fountain solution in on-press development. However, this technique has had a problem that the addition of a hydrophilic compound simultaneously reduces the image strength and ink receptibility of the image areas and, hence, satisfactory printed matters are not obtained.

SUMMARY OF THE INVENTION

Accordingly, an object of the invention is to provide a lithographic printing plate precursor which gives a lithographic printing plate stably showing ink receptibility during printing and having excellent printing durability. Another object of the invention is to provide a lithographic printing plate precursor in which an image can be recorded with a laser and which, after the image recording, can be satisfactorily developed on a printing machine without via a development step to give a printing plate stably showing ink receptibility during printing and having excellent printing durability. Still another object of the invention is to provide a lithographic printing process which includes image recording with a laser and on-press development and which attains stable ink receptibility during printing and excellent printing durability while maintaining satisfactory on-press developability.

The present inventor made intensive investigations on the problems described above. As a result, it was found that a specific phosphonium compound is effective in attaining an excellent balance between on-press developability and the ink receptibility of image areas. The invention has been thus achieved.

The invention provides the following.

(1) A lithographic printing plate precursor, which comprises:

a support;

an image-recording layer; and a protective layer, in this order, wherein at least one of the image-recording layer and the protective layer comprises a phosphonium salt represented by formula (1):

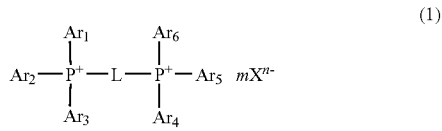

wherein $Ar_1$ to $Ar_6$ each independently represents an aryl group or a heterocyclic group;

L represents a divalent connecting group;

X represents a counter anion having a valence of n;

n represents an integer of from 1 to 3; and m is a number satisfying n×m=2.

(2) A lithographic printing plate precursor, which comprises:

a support;

an image-recording layer; and a protective layer, in this order, wherein at least one of the image-recording layer and the protective layer comprises a phosphonium salt represented by formula (2):

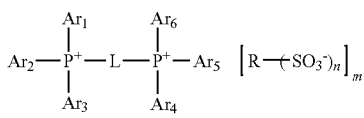

wherein $Ar_1$ to $Ar_6$ each independently represents an aryl group having from 6 to 15 carbon atoms;

L represents a divalent connecting group;

R represents an alkyl group, an aryl group, a heterocyclic group, an alkoxy group, an alkylamino group or an arylamino group;

n represents an integer of from 1 to 3; and m is a number satisfying n×m=2.

(3) The lithographic printing plate precursor as described in (1) or (2) above, wherein the image-recording layer further comprises an infrared absorber.

(4) The lithographic printing plate precursor as described in any of (1) to (3) above, wherein the image-recording layer further comprises a radical polymerization initiator and a radical-polymerizable compound.

(5) The lithographic printing plate precursor as described in any of (1) to (4) above, wherein the protective layer further comprises an inorganic layer compound.

(6) The lithographic printing plate precursor as described in any of (1) to (5) above, which can be developed on a printing machine after imagewise exposure.

(7) A lithographic printing process, which comprises:

imagewise exposing a lithographic printing plate precursor as described in (6) above;

mounting the printing plate precursor on a printing machine without via a development step; and conducting printing, or mounting a lithographic printing plate precursor as described in (6) above on a printing machine; then imagewise exposing the printing plate precursor; and conducting printing.

(8) A lithographic printing process, which comprises:

exposing a lithographic printing plate precursor, so as to form an exposed lithographic printing plate precursor;

supplying an oil-based ink and a fountain solution to the exposed lithographic printing plate precursor on a printing machine to remove an unexposed area of an image-recording layer of the exposed lithographic printing plate precursor; and conducting printing, wherein the fountain solution is a fountain solution comprising a phosphonium salt represented by formula (1) or (2):

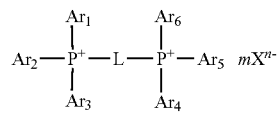

wherein $Ar_1$ to $Ar_6$ each independently represents an aryl group or a heterocyclic group;

L represents a divalent connecting group;

X represents a counter anion having a valence of n;

n represents an integer of from 1 to 3; and m is a number satisfying n×m=2:

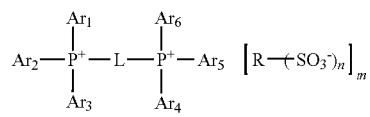

wherein $Ar_1$ to $Ar_6$ each independently represents an aryl group having from 6 to 15 carbon atoms;

L represents a divalent connecting group;

R represents an alkyl group, an aryl group, a heterocyclic group, an alkoxy group, an alkylamino group or an arylamino group;

n represents an integer of from 1 to 3; and m is a number satisfying n×m=2.

(9) A phosphonium salt represented by formula (2):

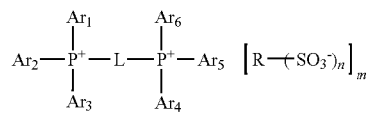

wherein $Ar_1$ to $Ar_6$ each independently represents an aryl group having from 6 to 15 carbon atoms;

L represents a divalent connecting group;

R represents an alkyl group, an aryl group, a heterocyclic group, an alkoxy group, an alkylamino group or an arylamino group;

n represents an integer of from 1 to 3; and m is a number satisfying n×m=2.

On-press developability and ink receptibility could be reconciled in the invention by incorporating a phosphonium salt represented by formula (1) in a lithographic printing plate precursor or a fountain solution.

Phosphonium compounds have generally been known from long ago as photosensitive acid generators as apparent from the fact that such application is shown in, e.g., JP-A-50-158698. Furthermore, to add a phosphonium compound to a fountain solution and cause the compound to function as a protective agent for the image areas of a PS plate is known as apparent from the fact that it is disclosed in, e.g., JP-A-5-112085. However, those patent documents neither disclose nor suggest any technique effective in accomplishing the subject in on-press development type plate precursor systems as in the invention that exposed area of a protective layer comprising a hydrophilic resin as the main component are removed and inhibited from being readsorbed while maintaining the penetration of a fountain solution during on-press development.

DETAILED DESCRIPTION OF THE INVENTION

The lithographic printing plate precursor of the invention is characterized in that a specific phosphonium salt is contained in the image-recording layer or the protective layer. One of the lithographic printing processes of the invention is characterized in that a fountain solution containing the specific phosphonium salt is used.

[Phosphonium Salt]

The phosphonium salt represented by formula (1) to be used in the lithographic printing plate precursor of the invention is described below.

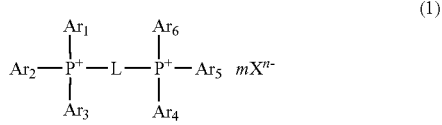

(1)

In the formula, $Ar_1$ to $Ar_6$ each independently represent an aryl group or a heterocyclic group; L represents a divalent connecting group; X represents a counter anion having a valence of n; n represents an integer of 1-3; and m is a number satisfying n×m=2. Preferred examples of the aryl group include phenyl, naphthyl, tolyl, xylyl, fluorophenyl, chlorophenyl, bromophenyl, methoxyphenyl, ethoxyphenyl, dimethoxyphenyl, methoxycarbonylphenyl, and dimethylaminophenyl. Examples of the heterocyclic group include pyridyl, quinolyl, pyrimidinyl, thienyl, and furyl.

The divalent connecting group represented by L is a connecting group comprising one or more nonmetallic atoms. Specifically, it comprises 1-60 carbon atoms, 0-10 nitrogen atoms, 0-50 oxygen atoms, 1-100 hydrogen atoms, and 0-20 sulfur atoms. More specific examples of the connecting group include ones each comprising a combination of two or more of the following structural units.

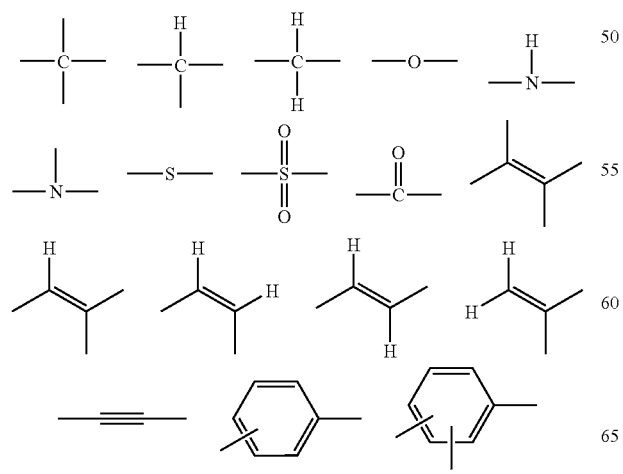

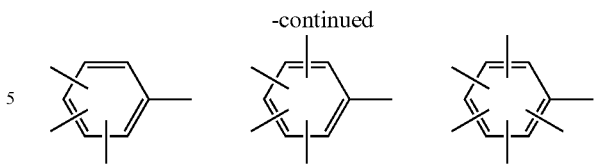

In the case where the divalent connecting group represented by L has one or more substituents, examples of the substituents include alkyl groups having 1-20 carbon atoms, such as methyl and ethyl, aryl groups having 6-16 carbon atoms such as phenyl and naphthyl, hydroxyl, carboxyl, sulfonamide groups, N-sulfonylamide groups, acyloxy groups having 1-6 carbon atoms, such as acetoxy, alkoxy groups having 1-6 carbon atoms, such as methoxy and ethoxy, halogen atoms such as chlorine and bromine, alkoxycarbonyl groups having 2-7 carbon atoms, such as methoxycarbonyl, ethoxycarbonyl, and cyclohexyloxycarbonyl, cyano, and carbonic ester groups such as t-butyl carbonate.

Preferred examples of the connecting group L include the following. Especially preferred of these are the connecting groups having 6-12 carbon atoms.

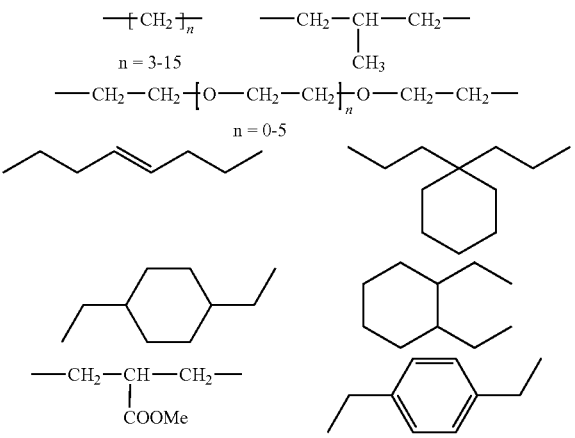

Preferred examples of the counter anion X include halogen anions, nitrate anion, sulfate anion, phosphate anion, sulfonate anions, carboxylate anions, $PF_6$, $BF_4$, perchlorate anion, and tetraarylborate anions. Especially preferred are phosphonium salts represented by the following formula (2), in which the counter anion is a sulfonate anion. Use of a phosphonium salt represented by formula (2) in the on-press development type lithographic printing plate precursor is effective in improving on-press developability.

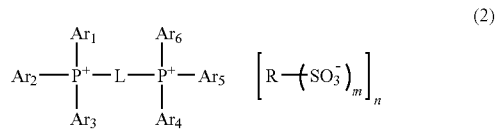

(2)

In the formula, R represents an alkyl, aryl, heterocyclic, alkoxy, alkylamino, or arylamino group. $Ar_1$ to $Ar_6$, L, m, and n have the same meanings as in formula (1).

Specific examples of the counter anion in formula (2) are shown below.
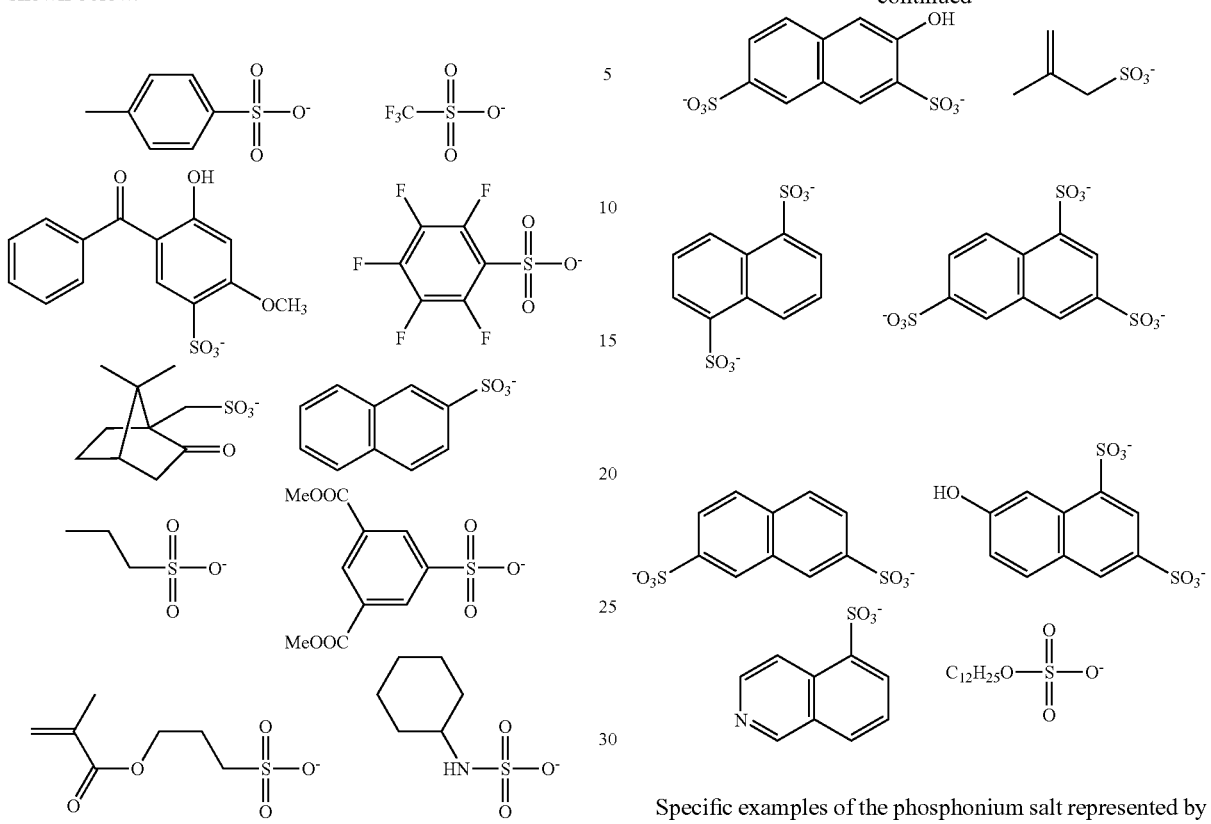
Specific examples of the phosphonium salt represented by formula (1) or (2) to be used in the invention are shown below.
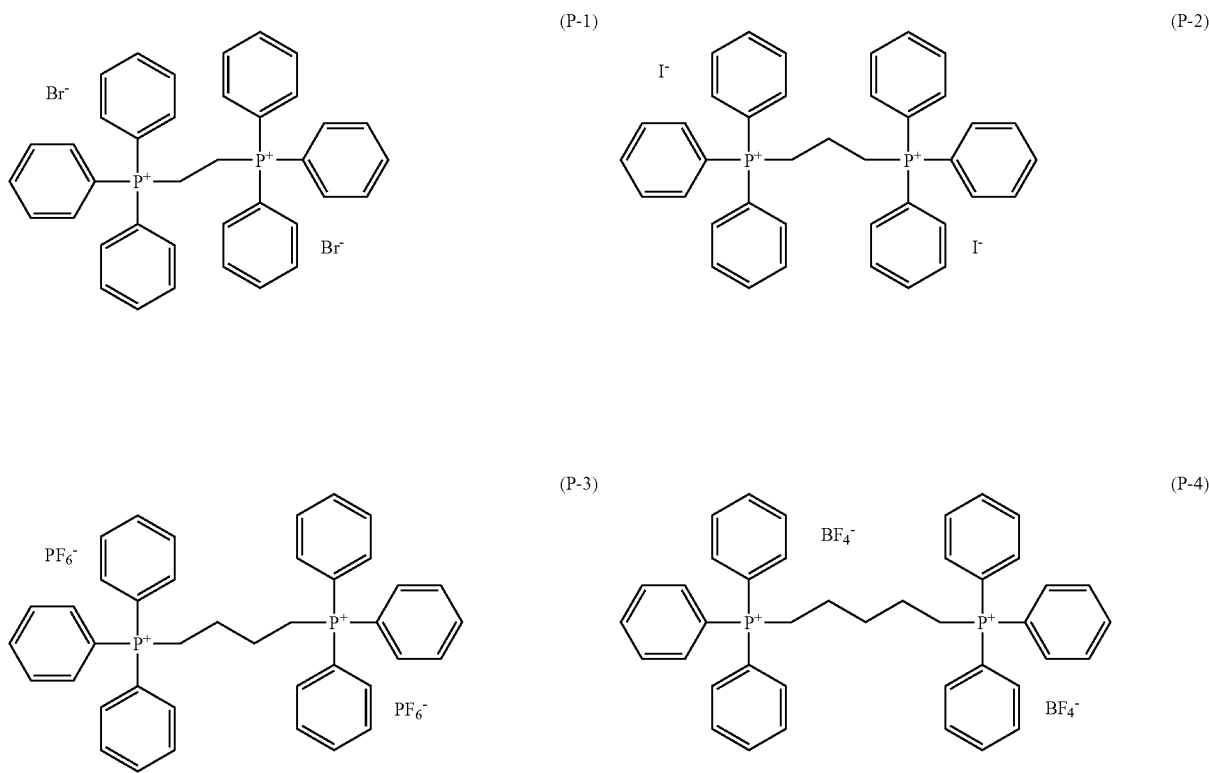

-continued
(P-5)
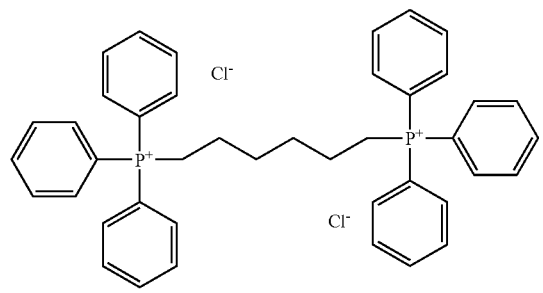
(P-6)
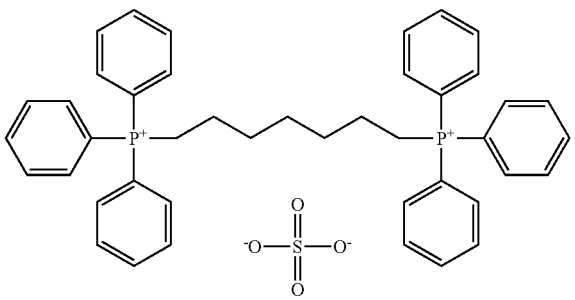
(P-7)
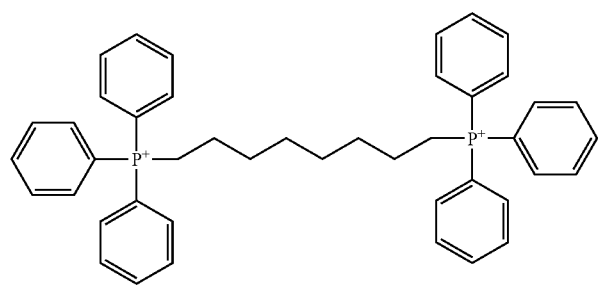
(P-8)
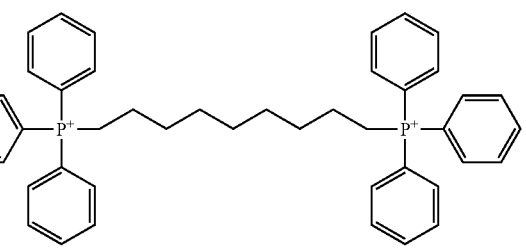
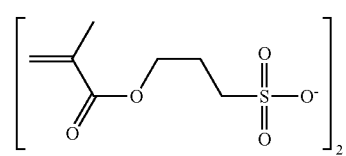
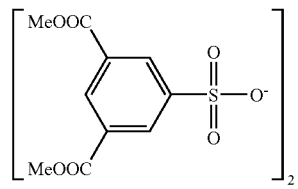
(P-9)
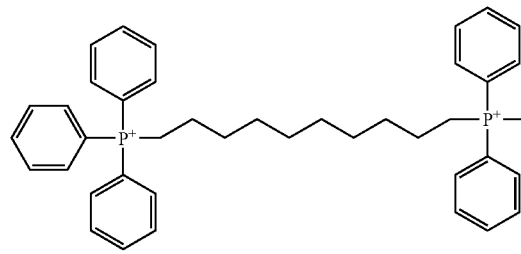
(P-10)
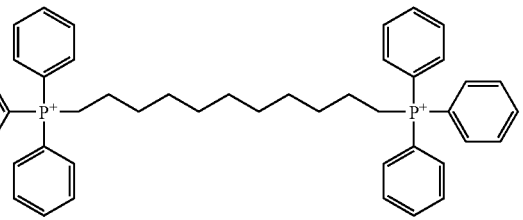
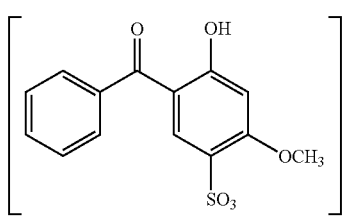
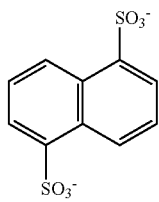
(P-11)
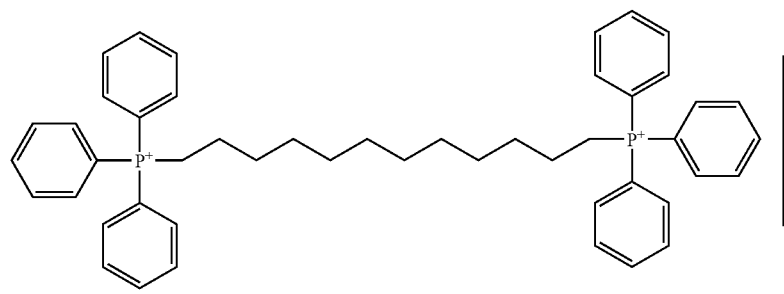
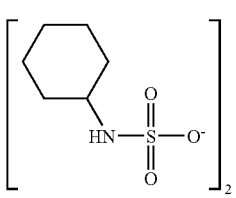

-continued
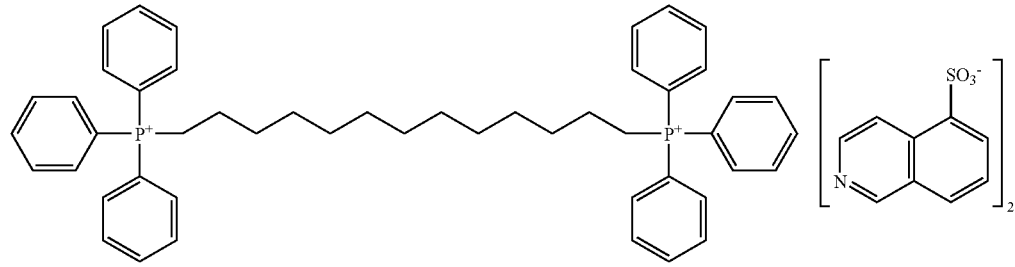
(P-12)
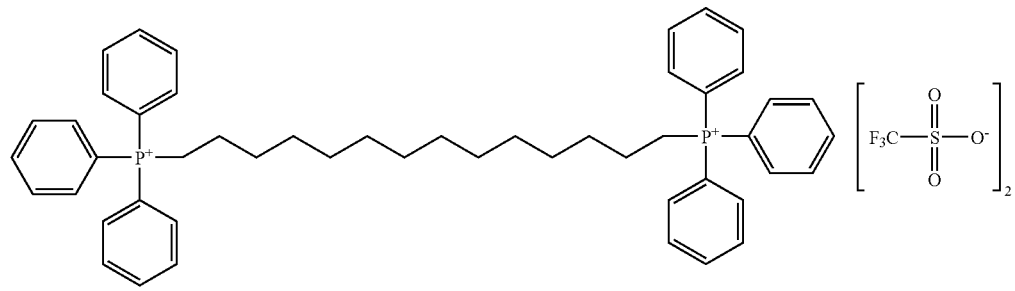
(P-13)
(P-14)
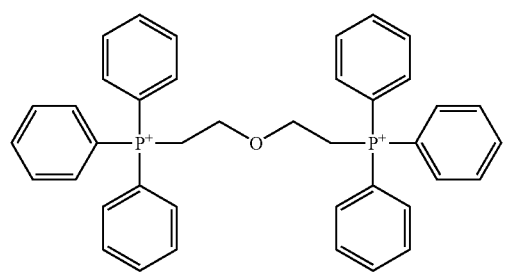
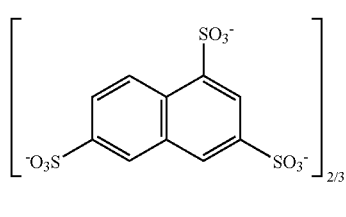
(P-15)
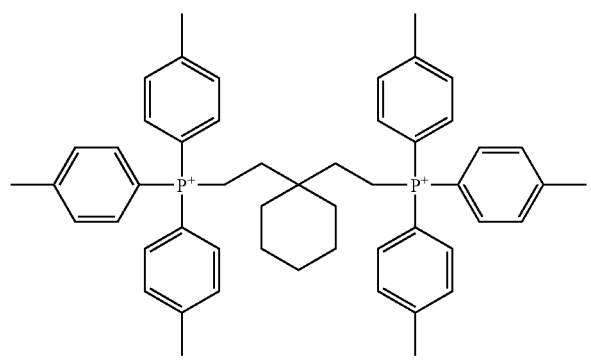
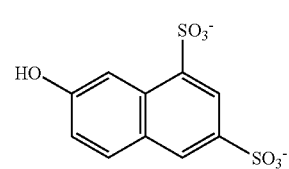

-continued
(P-16)
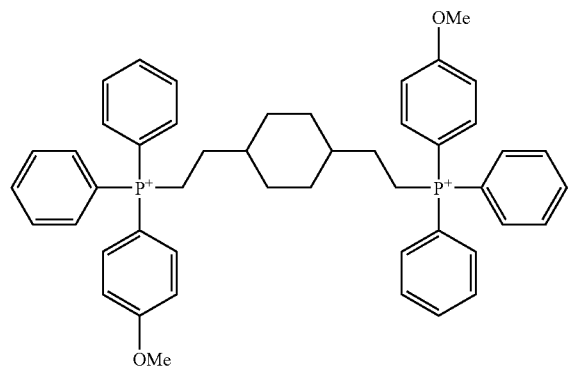
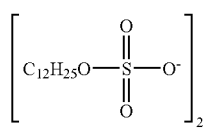
(P-17)
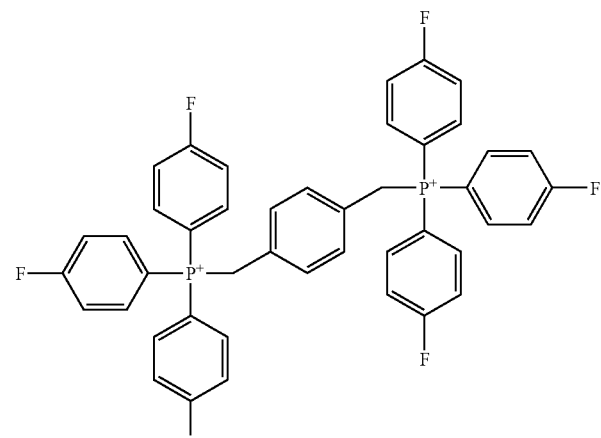
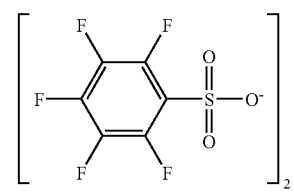
(P-18)
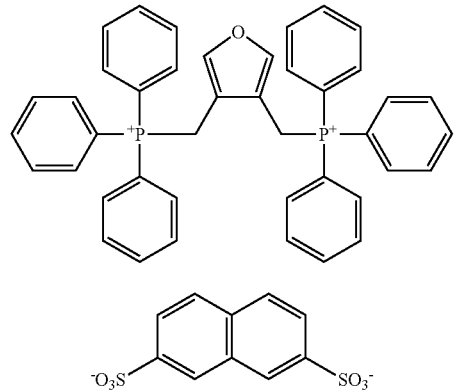
(P-19)
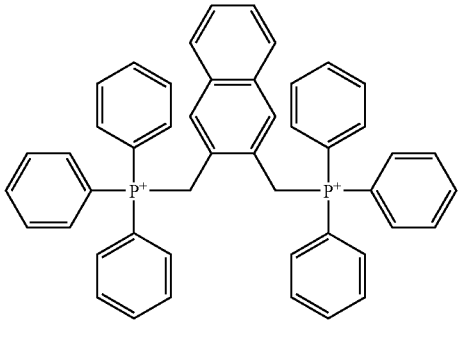
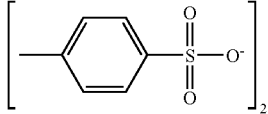
(P-20)
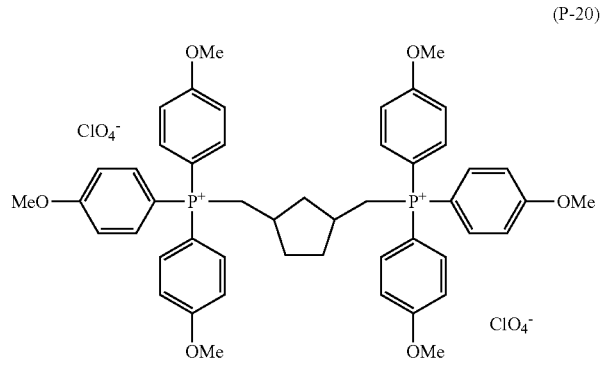
(P-21)
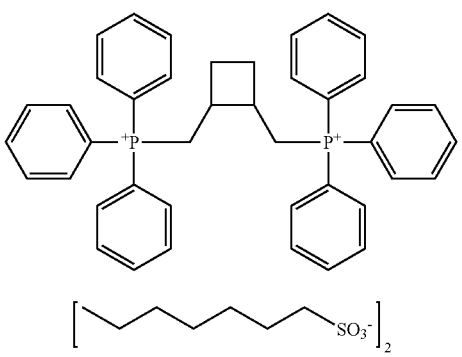
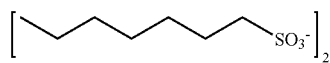

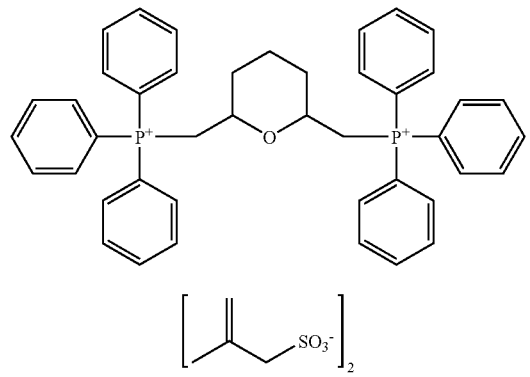

(P-22)

Examples of the synthesis of phosphonium salts for use in the invention are shown below.

<Synthesis of Nonamethylenebis(triphenylphosphonium) Dibromide>

28.61 Grams of 1,9-dibromononane and 52.46 g of triphenylphosphine were weighed out and placed in a 500-mL three-necked flask. These compounds were dissolved in 100 mL of N-methylpyrrolidone. This solution was stirred at 80° C. for 5 hours and the resultant reaction mixture was cooled to room temperature. Thereafter, the reaction mixture was poured into 500 mL of ethyl acetate kept being sufficiently stirred. The solid precipitated was collected by suction filtration and washed with 50 mL of ethyl acetate twice. The solid obtained was placed on a Petri dish and dried at room temperature under vacuum until the mass of the solid became constant. As a result, nonamethylenebis(triphenylphosphonium)dibromide was obtained as a white solid in an amount of 73 g (yield: 90%).

<Synthesis of Nonamethylenebis(triphenylphosphonium) Di(dimethyl 5-Sulfoisophthalate) (P-8)>

29.62 Grams of sodium dimethyl 5-sulfoisophthalate and 118.48 g of water were weighed out and placed in a 500-mL three-necked flask. The contents were heated to 80° C. to completely dissolve the salt. On the other hand, 16.22 g of nonamethylenebis(triphenylphosphonium)dibromide and 16.22 g of water were weighed out and placed in a 100-mL eggplant type flask, and the contents were heated to 80° C. to completely dissolve the salt. The aqueous nonamethylenebis (triphenylphosphonium)dibromide solution thus obtained was added to the aqueous sodium dimethyl 5-sulfoisophthalate solution kept being stirred at 80° C. The resultant mixture was continuously stirred for 1 hour under the same conditions. After the 1-hour stirring, heating was stopped and the mixture was allowed to cool. At the time when the temperature reached 70° C., 34 mL of acetone was added. The resultant mixture was allowed to cool while continuously stirring it under the same conditions. At the time when the liquid reaction mixture opacified (about 63° C.), seed crystals of the target compound were added thereto. After the mixture was allowed to cool to room temperature, it was cooled on an ice bath and continuously stirred for 2 hours at an internal temperature of about 0° C. After the 2-hour stirring, the solid precipitated was collected by suction filtration and washed with 400 mL of distilled water. The solid obtained was placed in a 1-L beaker and 400 mL of distilled water was added thereto. This mixture was continuously stirred at room temperature for 1 hour. The solid was collected by suction filtration and washed with 100 mL of distilled water twice. The solid obtained was placed on a Petri dish and dried at 50° C. under vacuum until the mass of the solid became constant. As a result, nonamethylenebis(triphenylphosphonium)di(dimethyl 5-sulfoisophthalate) (P-8) was obtained as a white solid in an amount of 19.6 g (yield: 82%).

[Image-Recording Layer]

The image-recording layer in the invention preferably contains an infrared absorber so as to be capable of recording by infrared irradiation. Furthermore, the image-recording layer preferably is one containing a radical polymerization initiator and a radical-polymerizable compound. Moreover, the image-recording layer in the invention preferably is one in which, after exposure, the unexposed areas can be removed on a printing machine by supplying an oil-based ink and an aqueous ingredient thereto without via any development step.

In the lithographic printing plate precursor having such a composition, when the image-recording layer is irradiated with infrared, the exposed areas of the layer cure to form hydrophobic (oleophilic) regions. Upon initiation of printing, the unexposed areas are rapidly removed from the support surface with a fountain solution and an oily ingredient such as an ink or with an emulsion comprising a fountain solution and an oily ingredient.

<Infrared Absorber>

In the case where the lithographic printing plate precursor of the invention is subjected to image formation with a laser which emits infrared rays of 760-1,200 nm as a light source, it is generally essential to use an infrared absorber. An infrared absorber has the function of converting absorbed infrared rays into heat. The radical polymerization initiator (radical generator), which will be described later, is pyrolyzed by the resultant heat to generate a radical. The infrared absorber to be used in the invention is a dye or pigment having an absorption maximum in the wavelength range of from 760 to 1,200 nm.

As the dye can be used any of commercial dyes and known dyes described in the literature, e.g., Senryô Binran (edited by The Society of Synthetic Organic Chemistry, Japan, published in 1970). Examples thereof include dyes such as azo dyes, metal complex azo dyes, pyrazolone azo dyes, naphthoquinone dyes, anthraquinone dyes, phthalocyanine dyes, carbonium dyes, quinoneimine dyes, methine dyes, cyanine dyes, squarylium dyes, pyrylium salts, and metal thiolate complexes.

Preferred examples of such dyes include the cyanine dyes shown in, e.g., JP-A-58-125246, JP-A-59-84356, and JP-A-60-78787, the methine dyes shown in, e.g., JP-A-58-173696, JP-A-58-181690, and JP-A-58-194595, the naphthoquinone dyes shown in, e.g., JP-A-58-112793, JP-A-58-224793, JP-A-59-48187, JP-A-59-73996, JP-A-60-52940, and JP-A-60-63744, the squarylium dyes shown in, e.g., JP-A-58-112792, and the cyanine dyes shown in British Patent No. 434,875.

The near-infrared-absorbing sensitizer described in U.S. Pat. No. 5,156,938 also is advantageously used. Furthermore, the substituted arylbenzo(thio)pyrylium salts shown in U.S. Pat. No. 3,881,924, the trimethinethiapyrylium salts shown in JP-A-57-142645 (U.S. Pat. No. 4,327,169), the pyrylium compounds shown in JP-A-58-181051, JP-A-58-220143, JP-A-59-41363, JP-A-59-84248, JP-A-59-84249, JP-A-59-146063, and JP-A-59-146061, the cyanine dyes shown in JP-A-59-216146, the pentamethinethiopyrylium salts shown in U.S. Pat. No. 4,283,475, and the pyrylium compounds shown in JP-B-5-13514 and JP-B-5-19702 are advantageously used. Other preferred examples of the dye include the near-infrared-absorbing dyes represented by the formulae (I) and (II) shown in U.S. Pat. No. 4,756,993.

Other preferred examples of the infrared-absorbing dye in the invention include the specific indolenine cyanine dyes shown below, which are given in JP-A-2002-278057.

Especially preferred of those dyes are cyanine dyes, squarylium dyes, pyrylium salts, nickel thiolate complexes, and indolenine cyanine dyes. More preferred are cyanine dyes and indolenine cyanine dyes. An especially preferred example is a cyanine dye represented by the following formula (i).

Formula (i)

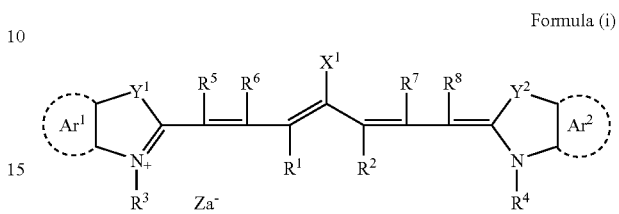

In formula (i), $X^1$ represents a hydrogen atom, halogen atom, —NPh$_2$, $X^2$-L$^1$, or the group shown below, wherein $X^2$ represents an oxygen atom, nitrogen atom, or sulfur atom and L$^1$ represents a hydrocarbon group having 1-12 carbon atoms,

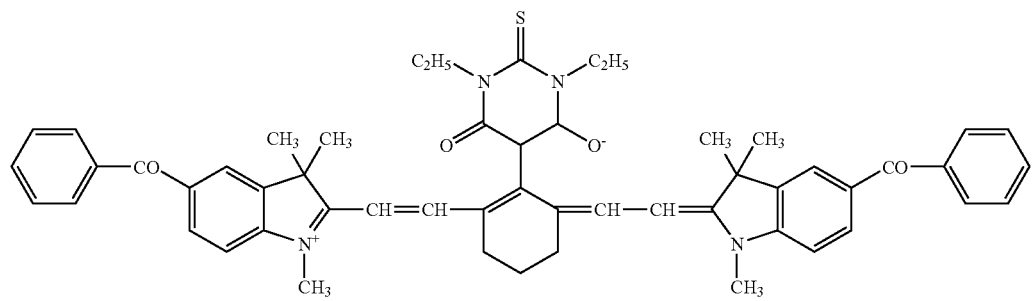

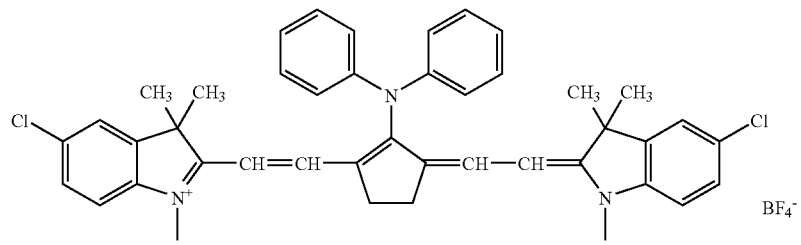

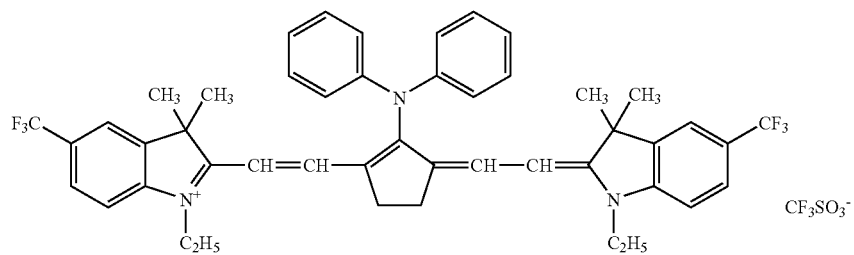

an aromatic ring having one or more heteroatoms, or a hydrocarbon group having 1-12 carbon atoms and containing one or more heteroatoms. The term heteroatoms herein means N, S, O, halogen atoms, and Se. Xa⁻ has the same meaning as Za⁻, which will be described later. $R^a$ represents a hydrogen atom or a substituent selected from alkyl groups, aryl groups, a substituted or unsubstituted amino group, and halogen atoms.

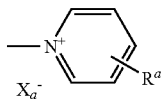

$R^1$ and $R^2$ each independently represent a hydrocarbon group having 1-12 carbon atoms. From the standpoint of the storage stability of a coating fluid for recording layer formation, $R^1$ and $R^2$ preferably are hydrocarbon groups having 2 or more carbon atoms, and especially preferably are bonded to each other to form a 5- or 6-membered ring.

$Ar^1$ and $Ar^2$ may be the same or different and each represent an aromatic hydrocarbon group which may have one or more substituents. Preferred examples of the aromatic hydrocarbon group include a benzene ring and a naphthalene ring. Preferred examples of the substituents include hydrocarbon groups having up to 12 carbon atoms, halogen atoms, and alkoxy groups having up to 12 carbon atoms. $Y^1$ and $Y^2$ may be the same or different and each represent a sulfur atom or a dialkylmethylene group having up to 12 carbon atoms. $R^3$ and $R^4$ may be the same or different and each represent a hydrocarbon group having up to 20 carbon atoms and optionally having one or more substituents. Preferred examples of the substituents include alkoxy groups having up to 12 carbon atoms, carboxyl, and sulfo. $R^5$, $R^6$, $R^7$, and $R^8$ may be the same or different and each represent a hydrogen atom or a hydrocarbon group having up to 12 carbon atoms. From the standpoint of starting-material availability, $R^5$, $R^6$, $R^7$, and $R^8$ preferably are hydrogen atoms. Za⁻ represents a counter anion, provided that when the cyanine dye represented by formula (i) has an anionic substituent in its structure and does not necessitate charge neutralization, then Za⁻ is not necessary. From the standpoint of the storage stability of a coating fluid for recording layer formation, preferred examples of Za⁻ are a halogen ion, perchlorate ion, tetrafluoroborate ion, hexafluorophosphate ion, and sulfonate ion. Especially preferred are a perchlorate ion, hexafluorophosphate ion, and arylsulfonate ion.

Examples of the cyanine dye represented by formula (i) which are suitable for use in the invention include the cyanine dyes shown in JP-A-2001-133969, paragraphs [0017] to [0019].

Other especially preferred examples thereof include the specific indolenine cyanine dyes given in JP-A-2002-278057 which were shown above.

As the pigment for use in the invention can be utilized any of commercial pigments and pigments described in *Color Index (C.I.) Binran, Saishin Ganryô Binran* (edited by Japan Association of Pigment Technology, published in 1977), *Saishin Ganryô Ôyô Gijutsu* (CMC Publishing Co., Ltd. published in 1986), and *Insatsu Inki Gijutsu* (CMC Publishing Co., Ltd. published in 1984).

Examples of the kinds of such pigments include black pigments, yellow pigments, orange pigments, brown pigments, red pigments, violet pigments, blue pigments, green pigments, fluorescent pigments, metal powder pigments, and polymer-bonded dyes. Specific examples thereof include insoluble azo pigments, azo lake pigments, condensation azo pigments, chelate azo pigments, phthalocyanine pigments, anthraquinone pigments, perylene and perinone pigments, thioindigo pigments, quinacridone pigments, dioxazine pigments, isoindolinone pigments, quinophthalone pigments, dyed lake pigments, azine pigments, nitroso pigments, nitro pigments, natural pigments, fluorescent pigments, inorganic pigments, and carbon black. Preferred of these pigments is carbon black. Those pigments may be used without being surface-treated, or may be used after having undergone a surface treatment. Possible techniques for the surface treatment include a method in which the pigment surface is coated with a resin or wax, a method in which a surfactant is adhered, and a method in which a reactive substance (e.g., a silane coupling agent, epoxy compound, or polyisocyanate) is bonded to the pigment surface. These surface treatment techniques are described in *Kinzoku Sekken No Seishitsu To Ôyô* (Saiwai Shobo), *Insatsu Inki Gijutsu* (CMC Publishing Co., Ltd., published in 1984), and *Saishin Ganryô Ôyô Gijutsu* (CMC Publishing Co., Ltd., published in 1986).

The particle diameter of the pigment is in the range of preferably 0.01-10 μm, more preferably 0.05-1 μm, especially preferably 0.1-1 μm. When the pigment has a particle diameter within this range, a pigment dispersion which is satisfactorily stable in a coating fluid for image-recording layer formation and an image-recording layer having satisfactory evenness are obtained.

For dispersing the pigment, known dispersion techniques for use in ink production, toner production, or the like can be used. Examples of dispersing machines include an ultrasonic disperser, sand mill, attritor, pearl mill, supermill, ball mill, impeller, disperser, KD mill, colloid mill, dynatron, three-roll mill, and pressure kneader. Such dispersion techniques are described in detail in *Saishin Ganryô Ôyô Gijutsu* (CMC Publishing Co., Ltd., published in 1986).

Those infrared absorbers may be added to the same layer as other ingredients or may be added to another layer separately formed. However, the infrared absorbers are added so that the image-recording layer of the negative lithographic printing plate precursor produced has an absorbance in the range of 0.3-1.2 when examined by the reflection method at an absorption-maximum wavelength in the wavelength range of 760-1,200 nm. Preferably, the absorbance thereof is in the range of 0.4-1.1. When the image-recording layer has an absorbance within that range, polymerization reaction proceeds evenly throughout the whole depth of the image-recording layer to give image areas satisfactory in film strength and adhesion to the support.

The absorbance of the image-recording layer can be regulated by changing the amount of the infrared absorber to be added to the image-recording layer and the thickness of the image-recording layer. For measuring the absorbance, ordinary methods can be used. Examples of usable methods include a method in which an image-recording layer is formed on a reflective support, e.g., aluminum, in a suitably determined dry thickness in the range necessary for the lithographic printing plate precursor and the reflection density of the layer is measured with an optical densitometer or is measured with a spectrophotometer by the reflection method using an integrating sphere.

<Radical Polymerization Initiator>

The radical polymerization initiator (hereinafter often referred to simply as "polymerization initiator") to be used in the invention is a compound which generates a radical by the action of light energy or heat energy or both and thereby initiate and accelerate the polymerization of compounds having a polymerizable unsaturated group. Examples of polymerization initiators usable in the invention include known heat polymerization initiators, compounds having a low bond dissociation energy, and photopolymerization initiators. Of these, preferred polymerization initiators for use in the invention are compounds which generate a radical by the action of heat energy and thereby initiate and accelerate the polymerization of compounds having a polymerizable unsaturated group.

Such polymerization initiators for use in the invention will be explained below in more detail. These polymerization initiators may be used alone or in combination of two or more thereof.

Examples of those polymerization initiators include organic halogen compounds, carbonyl compounds, organic peroxides, azo polymerization initiators, azide compounds, metallocene compounds, hexaarylbiimidazole compounds, organoboron compounds, disulfone compounds, oxime ester compounds, and onium salt compounds.

Examples of the organic halogen compounds include the compounds given in Wakabayashi et al., *Bull. Chem. Soc. Japan*, 42, 2924 (1969), U.S. Pat. No. 3,905,815, JP-B-46-4605, JP-A-48-36281, JP-A-53-133428, JP-A-55-32070, JP-A-60-239736, JP-A-61-169835, JP-A-61-169837, JP-A-62-58241, JP-A-62-212401, JP-A-63-70243, JP-A-63-298339, and M. P. Hutt, *Journal of Heterocyclic Chemistry*, 1 (No. 3), (1970). Preferred of these are the oxazole compounds and s-triazine compounds substituted by one or more trihalomethyl groups.

More preferred are s-triazine derivatives in which at least one mono-, di-, or trihalogenated methyl group is bonded to the s-triazine ring. Specific examples thereof include 2,4,6-tris(monochloromethyl)-s-triazine, 2,4,6-tris(dichloromethyl)-s-triazine, 2,4,6-tris(trichloromethyl)-s-triazine, 2-methyl-4,6-bis(trichloromethyl)-s-triazine, 2-n-propyl-4,6-bis(trichloromethyl)-s-triazine, 2-($\alpha,\alpha,\beta$-trichloroethyl)-4,6-bis(trichloromethyl)-s-triazine, 2-phenyl-4,6-bis(trichloromethyl)-s-triazine, 2-(p-methoxyphenyl)-4,6-bis(trichloromethyl)-s-triazine, 2-(3,4-epoxyphenyl)-4,6-bis(trichloromethyl)-s-triazine, 2-(p-chlorophenyl)-4,6-bis(trichloromethyl)-s-triazine, 2-[1-(p-methoxyphenyl)-2,4-butadienyl]-4,6-bis(trichloromethyl)-s-triazine, 2-styryl-4,6-bis(trichloromethyl)-s-triazine, 2-(p-methoxystyryl)-4,6-bis(trichloromethyl)-s-triazine, 2-(p-isopropyloxystyryl)-4,6-bis(trichloromethyl)-s-triazine, 2-(p-tolyl)-4,6-bis(trichloromethyl)-s-triazine, 2-(4-methoxynaphthyl)-4,6-bis(trichloromethyl)-s-triazine, 2-phenylthio-4,6-bis(trichloromethyl)-s-triazine, 2-benzylthio-4,6-bis(trichloromethyl)-s-triazine, 2,4,6-tris(dibromomethyl)-s-triazine, 2,4,6-tris(tribromomethyl)-s-triazine, 2-methyl-4,6-bis(tribromomethyl)-s-triazine, and 2-methoxy-4,6-bis(tribromomethyl)-s-triazine.

Examples of the carbonyl compounds include benzophenone and derivatives thereof such as Michler's ketone, 2-methylbenzophenone, 3-methylbenzophenone, 4-methylbenzophenone, 2-chlorobenzophenone, 4-bromobenzophenone, and 2-carboxybenzophenone, acetophenone derivatives such as 2,2-dimethoxy-2-phenylacetophenone, 2,2-diethoxyacetophenone, 1-hydroxycyclohexyl phenyl ketone, $\alpha$-hydroxy-2-methylphenylpropanone, 1-hydroxy-1-methylethyl p-isopropylphenyl ketone, 1-hydroxy-1-(p-dodecylphenyl) ketone, 2-methyl-(4'-(methylthio)phenyl)-2-morpholino-1-propanone, and 1,1,1-trichloromethyl p-butylphenyl ketone, thioxanthone and derivatives thereof such as 2-ethylthioxanthone, 2-isopropylthioxanthone, 2-chlorothioxanthone, 2,4-dimethylthioxanthone, 2,4-diethylthioxanthone, and 2,4-diisopropylthioxanthone, and benzoic ester derivatives such as ethyl p-dimethylaminobenzoate and ethyl p-diethylaminobenzoate.

Examples of the azo compounds include the azo compounds given in JP-A-8-108621.

Examples of the organic peroxides include trimethylcyclohexanone peroxide, acetylacetone peroxide, 1,1-bis(tert-butylperoxy)-3,3,5-trimethylcyclohexane, 1,1-bis(tert-butylperoxy)cyclohexane, 2,2-bis(tert-butylperoxy)butane, tert-butyl hydroperoxide, cumene hydroperoxide, diisopropylbenzene hydroperoxide, 2,5-dimethylhexane 2,5-dihydroperoxide, 1,1,3,3-tetramethylbutyl hydroperoxide, tert-butyl cumyl peroxide, dicumyl peroxide, 2,5-dimethyl-2,5-di(tert-butylperoxy)hexane, 2,5-oxanoyl peroxide, succinic acid peroxide, benzoyl peroxide, 2,4-dichlorobenzoyl peroxide, diisopropyl peroxydicarbonate, di-2-ethylhexyl peroxydicarbonate, di-2-ethoxyethyl peroxydicarbonate, dimethoxyisopropyl peroxycarbonate, di(3-methyl-3-methoxybutyl)peroxydicarbonate, tert-butyl peroxyacetate, tert-butyl peroxypivalate, tert-butyl peroxylaurate, tosyl carbonate, 3,3',4,4'-tetra(t-butylperoxycarbonyl)benzophenone, 3,3',4,4'-tetra(t-hexylperoxycarbonyl)benzophenone, 3,3',4,4'-tetra(p-isopropylcumylperpoxycarbonyl)benzophenone, carbonyldi(t-butyl peroxydihydrodiphthalate), and carbonyldi(t-hexyl peroxydihydrodiphthalate).

Examples of the metallocene compounds include the various titanocene compounds given in JP-A-59-152396, JP-A-61-151197, JP-A-63-41484, JP-A-2-249, JP-A-2-4705, and JP-A-5-83588, such as, e.g., di-cyclopentadienyl-Ti-bisphenyl, di-cyclopentadienyl-Ti-bis-2,6-difluorophen-1-yl, di-cyclopentadienyl-Ti-bis-2,4-difluorophen-1-yl, di-cyclopentadienyl-Ti-bis-2,4,6-trifluorophen-1-yl, di-cyclopentadienyl-Ti-bis-2,3,5,6-tetrafluorophen-1-yl, di-cyclopentadienyl-Ti-bis-2,3,4,5,6-pentafluorophen-1-yl, di-methylcyclopentadienyl-Ti-bis-2,6-diflorophen-1-yl, di-methylcyclopentadienyl-Ti-bis-2,4,6-trifluorophen-1-yl, di-methylcyclopentadienyl-Ti-bis-2,3,5,6-tetrafluorophen-1-yl, and di-methylcyclopentadienyl-Ti-bis-2,3,4,5,6-pentafluorophen-1-yl, and the iron-arene complexes given in JP-A-1-304453 and JP-A-1-152109.

Examples of the hexaarylbiimidazole compounds include the various compounds given in JP-B-6-29285 and U.S. Pat. Nos. 3,479,185, 4,311,783, and 4,622,286. Specific examples thereof include 2,2'-bis(o-chlorophenyl)-4,4',5,5'-tetraphenylbiimidazole, 2,2'-bis(o-bromophenyl)-4,4',5,5'-tetraphenylbiimidazole, 2,2'-bis(o,p-dichlorophenyl)-4,4',5,5'-tetraphenylbiimidazole, 2,2'-bis(o-chlorophenyl)-4,4',5,5'-tetra(m-methoxyphenyl)biimidazole, 2,2'-bis(o,o'-dichlorophenyl)-4,4',5,5'-tetraphenylbiimidazole, 2,2'-bis(o-nitrophenyl)-4,4',5,5'-tetraphenylbiimidazole, 2,2'-bis(o-methylphenyl)-4,4',5,5'-tetraphenylbiimidazole, and 2,2'-bis(o-trifluorophenyl)-4,4',5,5'-tetraphenylbiimidazole.

Examples of the organoboron compounds include the organic boric acid salts given in JP-A-62-143044, JP-A-62-150242, JP-A-9-188685, JP-A-9-188686, JP-A-9-188710, JP-A-2000-131837, JP-A-2002-107916, Japanese Patent No. 2764769, JP-A-2002-116539, and Kunz, Martin, *Rad Tech '98. Proceeding*, Apr. 19-22, 1998, Chicago, the organic boron-sulfonium complexes or organic boron-oxosulfonium complexes given in JP-A-6-157623, JP-A-6-175564, and JP-A-6-175561, the organic boron-iodonium complexes given in JP-A-6-175554 and JP-A-6-175553, the organic boron-phosphonium complexes given in JP-A-9-188710, and the organic boron-transition metal coordination complexes given in JP-A-6-348011, JP-A-7-128785, JP-A-7-140589, JP-A-7-306527, and JP-A-7-292014.

Examples of the disulfone compounds include the compounds given in JP-A-61-166544 and JP-A-2003-328465.

Examples of the oxime ester compounds include the compounds given in *J. C. S. Perkin II* (1979) 1653-1660, *J. C. S. Perkin II* (1979) 156-162, *Journal of Photopolymer Science and Technology* (1995) 202-232, and JP-A-2000-66385 and the compounds given in JP-A-2000-80068. Specific examples thereof include the compounds represented by the following structural formulae.

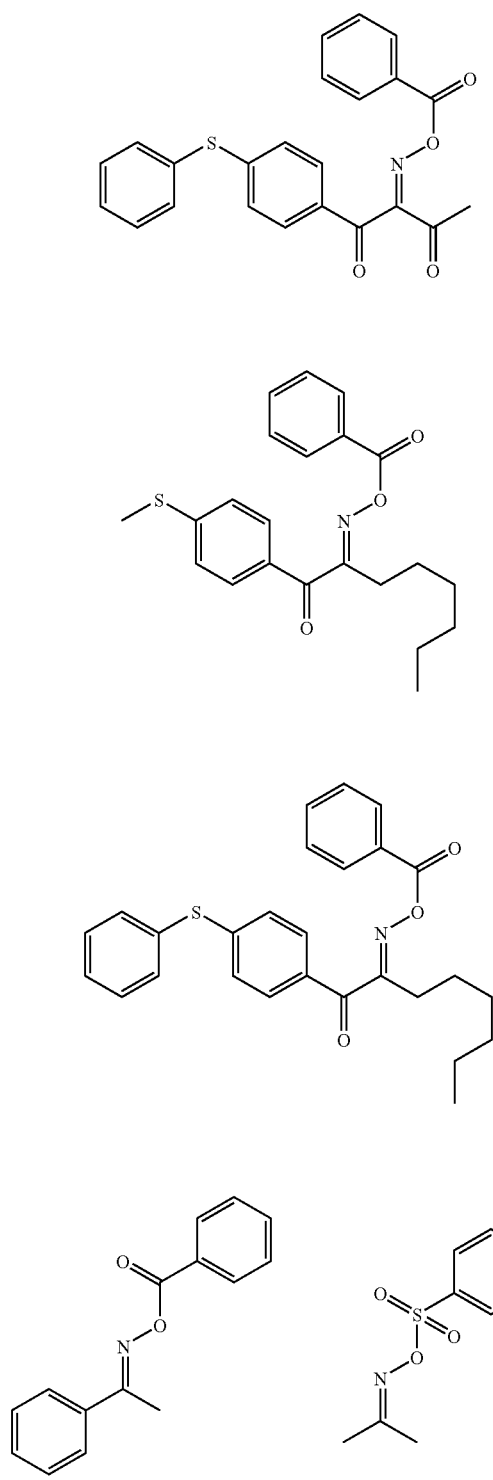

-continued

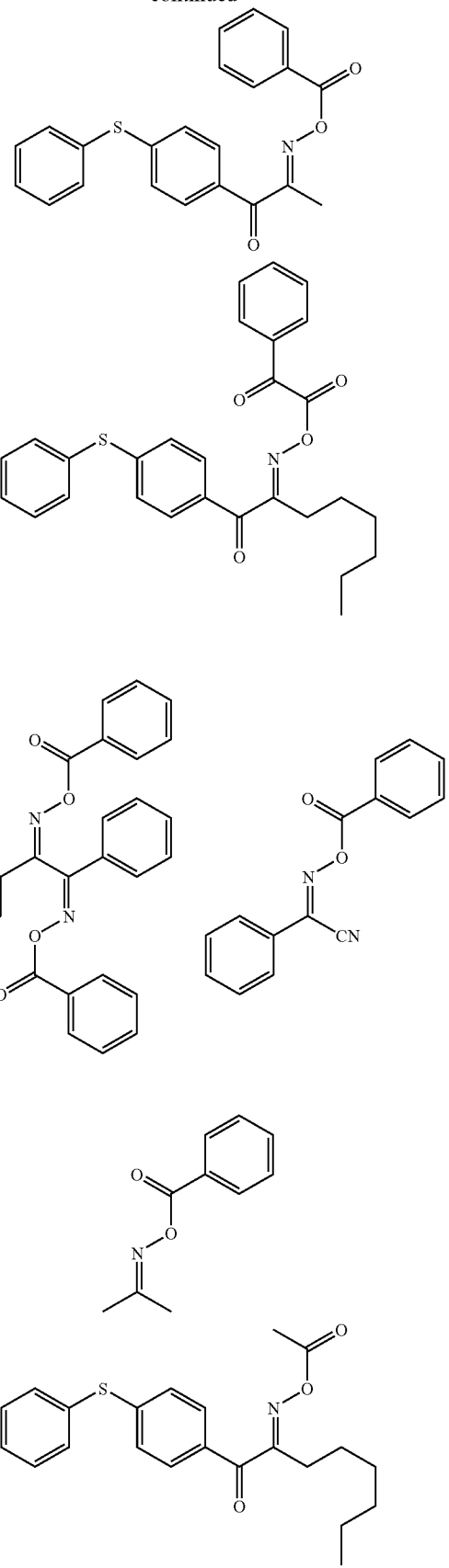

-continued

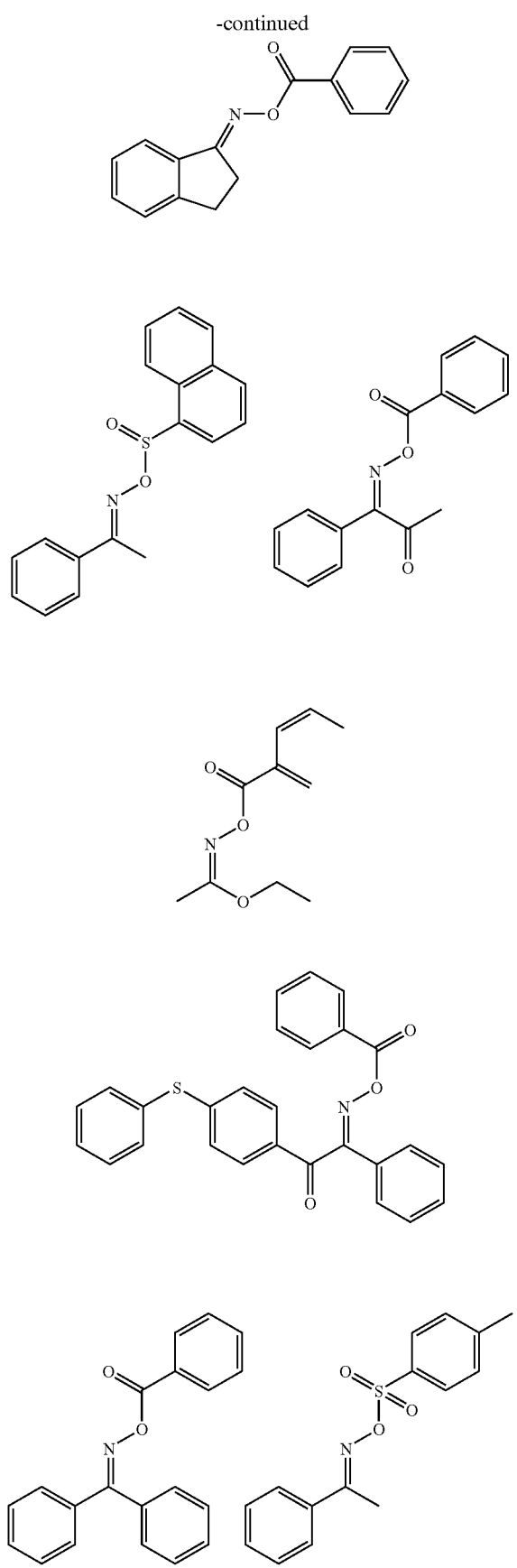

-continued

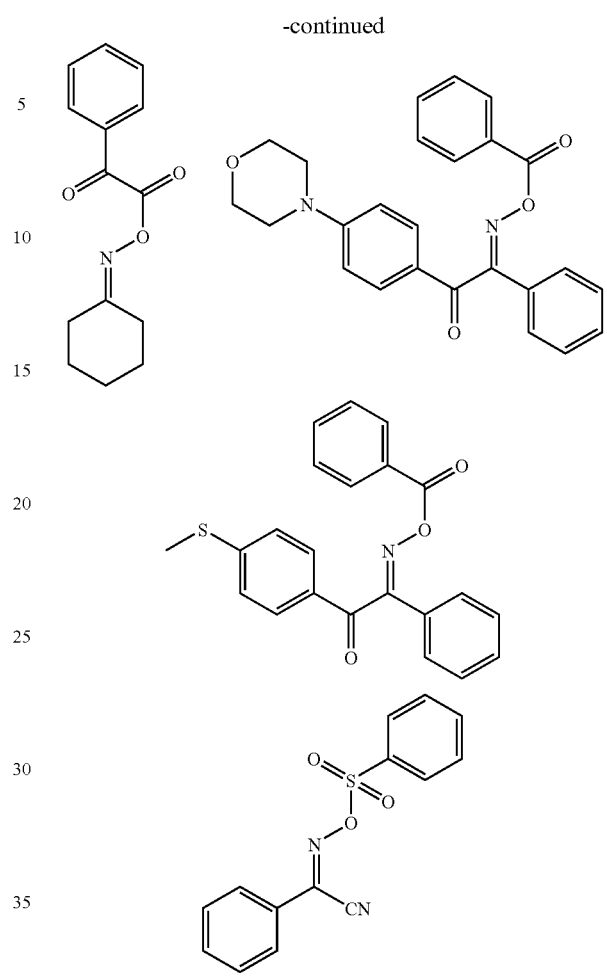

Examples of the onium salt compounds include the diazonium salts given in S. I. Schlesinger, *Photogr. Sci. Eng.*, 18, 387 (1974) and T. S. Bal et al., *Polymer*, 21, 423 (1980), the ammonium salts given in U.S. Pat. No. 4,069,055 and JP-A-4-365049, the phosphonium salts given in U.S. Pat. Nos. 4,069,055 and 4,069,056, the iodonium salts given in European Patent No. 104,143, U.S. Pat. Nos. 339,049 and 410,201, JP-A-2-150848, and JP-A-2-296514, the sulfonium salts given in European Patents Nos. 370,693, 390,214, 233,567, 297,443, and 297,442, U.S. Pat. Nos. 4,933,377, 161,811, 410,201, 339,049, 4,760,013, 4,734,444, and 2,833,827, German Patents Nos. 2,904,626, 3,604,580, and 3,604,581, the selenonium salts given in J. V. Crivello et al., *Macromolecules*, 10(6), 1307 (1977) and J. V. Crivello et al., *J. Polymer Sci.*, Polymer Chem. Ed., 17, 1047 (1979), and the arsonium salts given in C. S. Wen et al., *Teh. Proc. Conf. Rad. Curing ASIA*, p. 478, Tokyo, October (1988).

Especially from the standpoints of reactivity and stability, preferred examples include the oxime ester compounds or onium salts (diazonium salts, iodonium salts, or sulfonium salts) shown above. In the invention, these onium salts function not as acid generators but as ionic radical polymerization initiators.

The onium salts suitable for use in the invention are onium salts represented by the following formulae (RI-I) to (RI-III).

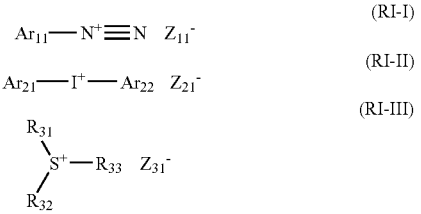

In formula (RI-I), $Ar_{11}$ represents an aryl group which has up to 20 carbon atoms and may have 1-6 substituents. Preferred examples of the substituents include alkyl groups having 1-12 carbon atoms, alkenyl groups having 1-12 carbon atoms, alkynyl groups having 1-12 carbon atoms, aryl groups having 1-12 carbon atoms, alkoxy groups having 1-12 carbon atoms, aryloxy groups having 1-12 carbon atoms, halogen atoms, alkylamino groups having 1-12 carbon atoms, dialkylamino groups having 1-12 carbon atoms, alkylamide or arylamide groups having 1-12 carbon atoms, carbonyl, carboxyl, cyano, sulfonyl, thioalkyl groups having 1-12 carbon atoms, and thioaryl groups having 1-12 carbon atoms. $Z_{11}^-$ represents a monovalent anion. Examples thereof include halogen ions, perchlorate ion, hexafluorophosphate ion, tetrafluoroborate ion, sulfonate ions, sulfinate ions, thiosulfinate ions, and sulfate ion. Preferred of these from the standpoint of safety are perchlorate ion, hexafluorophosphate ion, tetrafluoroborate ion, sulfonate ions, and sulfinate ions.

In formula (RI-II), $Ar_{21}$ and $Ar_{22}$ each independently represent an aryl group which has up to 20 carbon atoms and may have 1-6 substituents. Preferred examples of the substituents include alkyl groups having 1-12 carbon atoms, alkenyl groups having 1-12 carbon atoms, alkynyl groups having 1-12 carbon atoms, aryl groups having 1-12 carbon atoms, alkoxy groups having 1-12 carbon atoms, aryloxy groups having 1-12 carbon atoms, halogen atoms, alkylamino groups having 1-12 carbon atoms, dialkylamino groups having 1-12 carbon atoms, alkylamide or arylamide groups having 1-12 carbon atoms, carbonyl, carboxyl, cyano, sulfonyl, thioalkyl groups having 1-12 carbon atoms, and thioaryl groups having 1-12 carbon atoms. $Z_{21}^-$ represents a monovalent anion. Examples thereof include halogen ions, perchlorate ion, hexafluorophosphate ion, tetrafluoroborate ion, sulfonate ions, sulfinate ions, thiosulfinate ions, and sulfate ion. Preferred of these from the standpoints of safety and reactivity are perchlorate ion, hexafluorophosphate ion, tetrafluoroborate ion, sulfonate ions, sulfinate ions, and carboxylate ions.

In formula (RI-III), $R_{31}$, $R_{32}$, and $R_{33}$ each independently represent an aryl, alkyl, alkenyl, or alkynyl group which has up to 20 carbon atoms and may have 1-6 substituents. Aryl groups are preferred of these from the standpoints of reactivity and safety. Examples of the substituents include alkyl groups having 1-12 carbon atoms, alkenyl groups having 1-12 carbon atoms, alkynyl groups having 1-12 carbon atoms, aryl groups having 1-12 carbon atoms, alkoxy groups having 1-12 carbon atoms, aryloxy groups having 1-12 carbon atoms, halogen atoms, alkylamino groups having 1-12 carbon atoms, dialkylamino groups having 1-12 carbon atoms, alkylamide or arylamide groups having 1-12 carbon atoms, carbonyl, carboxyl, cyano, sulfonyl, thioalkyl groups having 1-12 carbon atoms, and thioaryl groups having 1-12 carbon atoms. $Z_{31}^-$ represents a monovalent anion. Examples thereof include halogen ions, perchlorate ion, hexafluorophosphate ion, tetrafluoroborate ion, sulfonate ions, sulfinate ions, thiosulfinate ions, sulfate ion, and carboxylate ions. Preferred of these from the standpoints of safety and reactivity are perchlorate ion, hexafluorophosphate ion, tetrafluoroborate ion, sulfonate ions, sulfinate ions, and carboxylate ions. More preferred examples thereof include the carboxylate ions shown in JP-A-2001-343742. Especially preferred examples include the carboxylate ions shown in JP-A-2002-148790.

Specific examples of the onium salt compounds suitable for use in the invention are shown below, but the onium salt compounds should not be construed as being limited to the following examples.

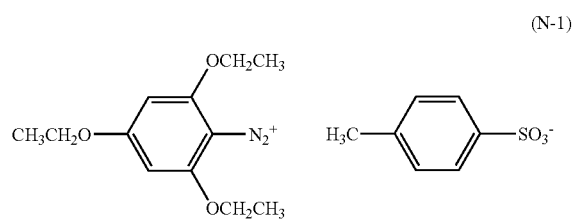

(N-1)

(N-2)

PF$_6^-$ (N-3)

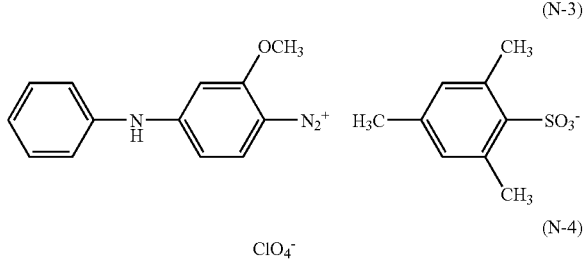

ClO$_4^-$ (N-4)

PF$_6^-$ (N-5)

(N-6)

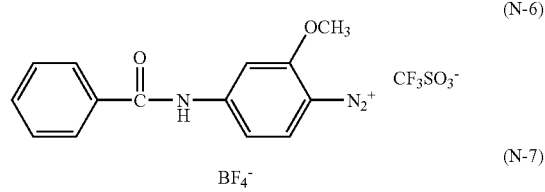

BF$_4^-$ (N-7)

(N-8)

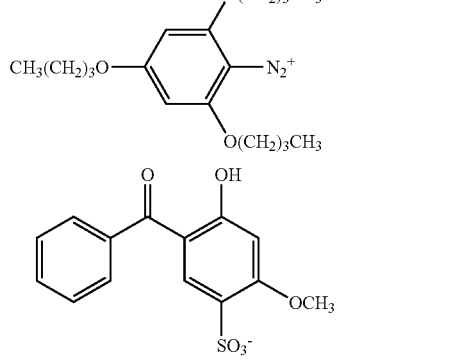

ClO$_4^-$ (N-9)

(N-10)

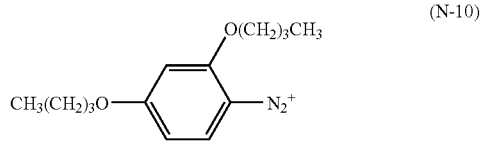

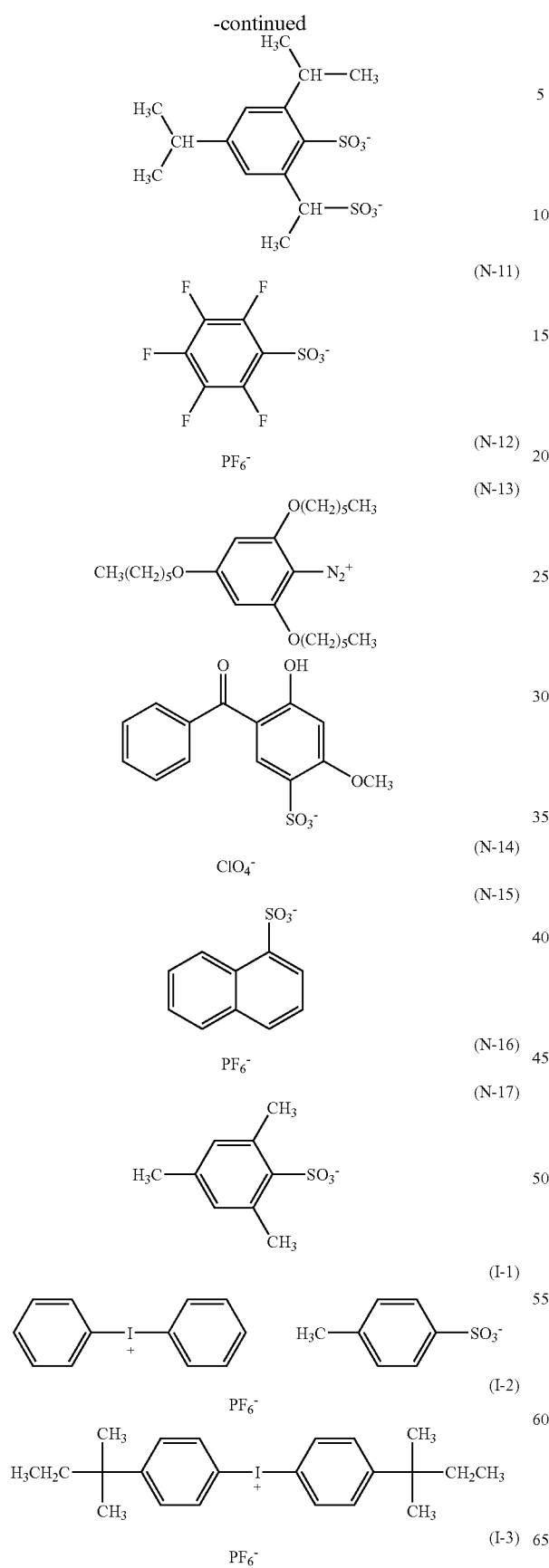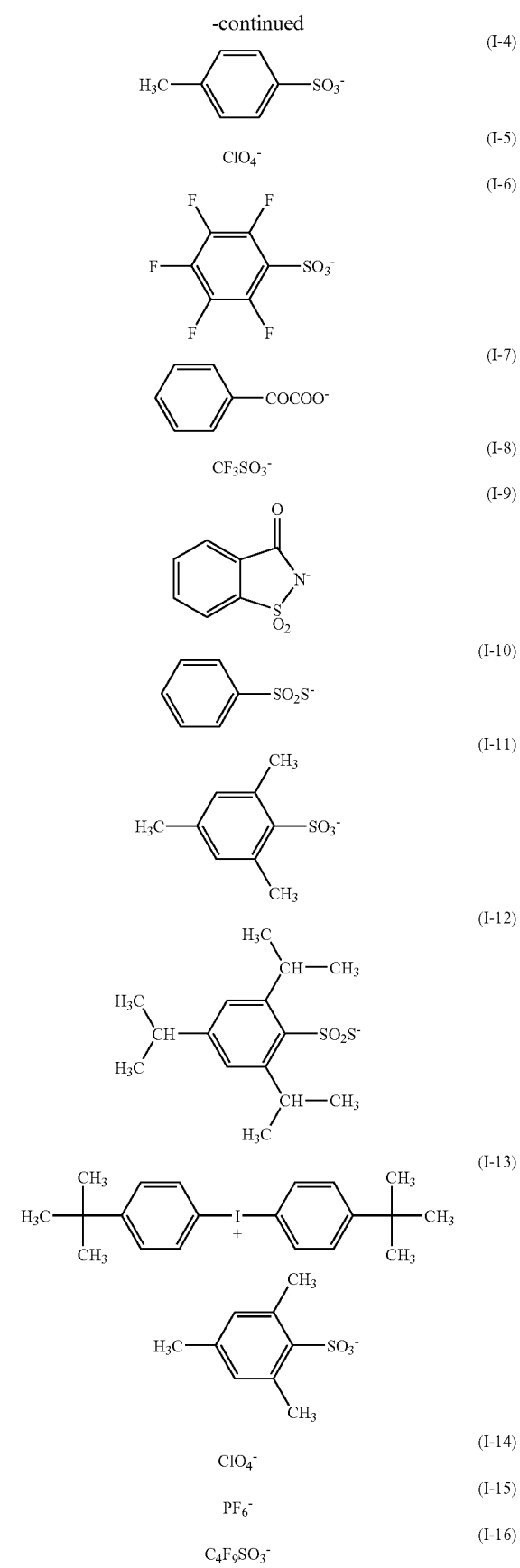

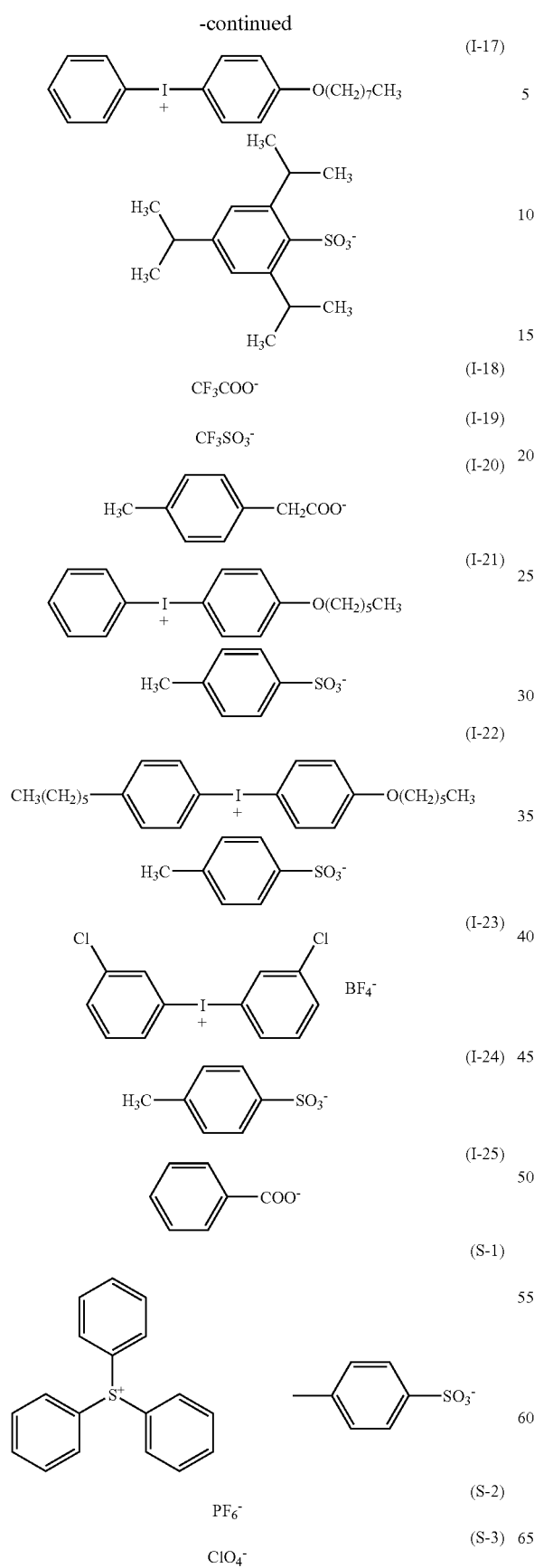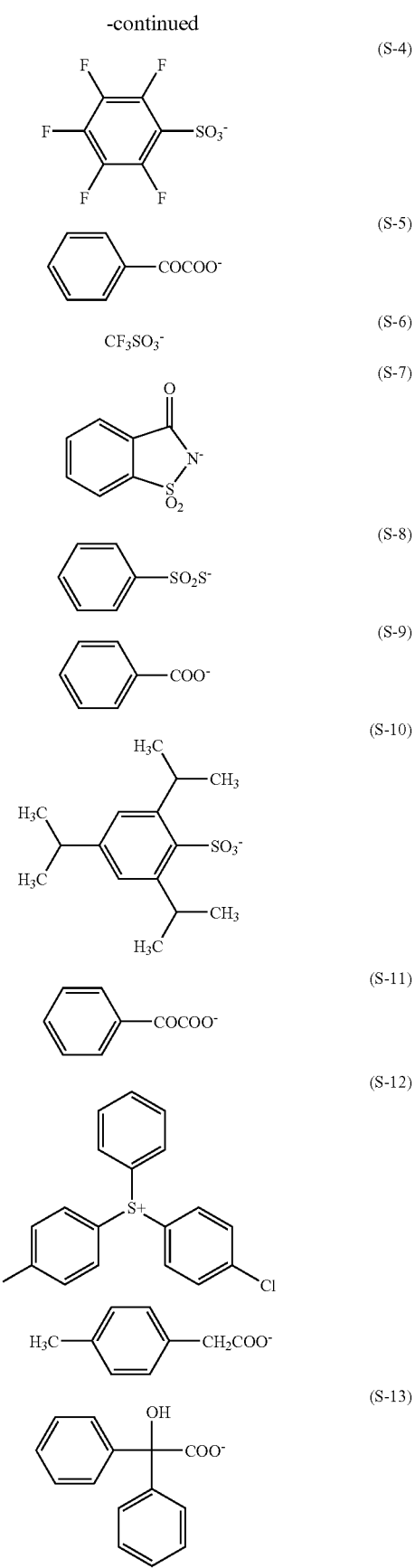

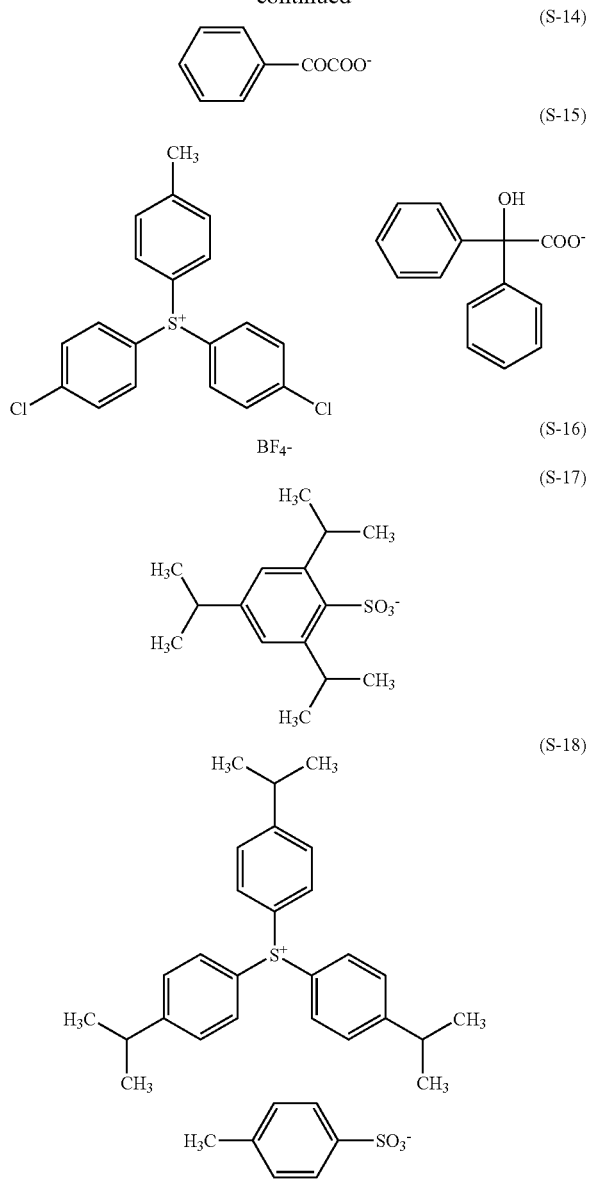

Those polymerization initiators can be added in an amount of 0.1-50% by mass, preferably 0.5-30% by mass, especially preferably 1-20% by mass, based on all solid ingredients constituting the image-recording layer. (In this specification, mass ratio is equal to weight ratio.) When the initiator amount is within this range, satisfactory sensitivity is obtained and the nonimage areas have satisfactory insusceptibility to scumming during printing. Those polymerization initiators may be used alone or in combination of two or more thereof. Any of those polymerization initiators and other ingredients may be added to the same layer. Alternatively, a layer containing any of the polymerization initiators may be separately formed.

<Radical-Polymerizable Compound>

The radical-polymerizable compound (hereinafter often referred to simply as "polymerizable compound") usable in the invention is an addition-polymerizable compound having at least one ethylenically unsaturated double bond. It is selected from compounds having at least one, preferably two or more ethylenically unsaturated bonds. Such compounds are well known in this industrial field, and can be used in the invention without particular limitations.

These are in chemical forms such as, e.g., a monomer, a prepolymer, i.e., dimer, trimer, or oligomer, and a mixture of two or more of these. Examples of such polymerizable compounds include unsaturated carboxylic acids (e.g., acrylic acid, methacrylic acid, itaconic acid, crotonic acid, isocrotonic acid, and maleic acid) and esters and amides of these. Preferably, an ester of an unsaturated carboxylic acid with an aliphatic polyhydric alcohol compound or an amide of an unsaturated carboxylic acid with an aliphatic polyamine compound is used. Also preferably used are: a product of the addition reaction of an unsaturated carboxylic acid ester or amide having a nucleophilic substituent, such as hydroxyl, amino, or mercapto, with a mono- or polyfunctional isocyanate or epoxy; a product of the dehydrating condensation reaction of the unsaturated carboxylic acid ester or amide with a mono- or polyfunctional carboxylic acid; and the like. Furthermore, a product of the addition reaction of an unsaturated carboxylic acid ester or amide having an electrophilic substituent, such as an isocyanate group or epoxy group, with a mono- or polyfunctional alcohol, amine, or thiol and a product of the substitution reaction of an unsaturated carboxylic acid ester or amide having an eliminable substituent, such as a halogen group or tosyloxy, with a mono- or polyfunctional alcohol, amine, or thiol are also preferred. Other usable examples include compounds obtained through these reactions using an unsaturated phosphonic acid, styrene, vinyl ether, or the like in place of the unsaturated carboxylic acid.

Examples of the monomeric ester of an aliphatic polyhydric alcohol compound with an unsaturated carboxylic acid include acrylic esters such as ethylene glycol diacrylate, triethylene glycol diacrylate, 1,3-butanediol diacrylate, tetramethylene glycol diacrylate, propylene glycol diacrylate, neopentyl glycol diacrylate, trimethylolpropane triacrylate, trimethylolpropane tri(acryloyloxypropyl)ether, trimethylolethane triacrylate, hexanediol diacrylate, 1,4-cyclohexanediol diacrylate, tetraethylene glycol diacrylate, pentaerythritol diacrylate, pentaerythritol triacrylate, pentaerythritol tetraacrylate, dipentaerythritol diacrylate, dipentaerythritol hexaacrylate, sorbitol triacrylate, sorbitol tetraacrylate, sorbitol pentaacrylate, sorbitol hexaacrylate, tri(acryloyloxyethyl)isocyanurate, polyester acrylate oligomers, and isocyanuric acid EO-modified triacrylate.

Examples of methacrylic esters include tetramethylene glycol dimethacrylate, triethylene glycol dimethacrylate, neopentyl glycol dimethacrylate, trimethylolpropane trimethacrylate, trimethylolethane trimethacrylate, ethylene glycol dimethacrylate, 1,3-butanediol dimethacrylate, hexanediol dimethacrylate, pentaerythritol dimethacrylate, pentaerythritol trimethacrylate, pentaerythritol tetramethacrylate, dipentaerythritol dimethacrylate, dipentaerythritol hexamethacrylate, sorbitol trimethacrylate, sorbitol tetramethacrylate, bis[p-(3-methacryloxy-2-hydroxypropoxy)phenyl]dimethylmethane, and bis[p-(methacryloxyethoxy)phenyl]dimethylmethane.

Examples of itaconic esters include ethylene glycol diitaconate, propylene glycol diitaconate, 1,3-butanediol diitaconate, 1,4-butanediol diitaconate, tetramethylene glycol diitaconate, pentaerythritol diitaconate, and sorbitol tetraitaconate. Examples of crotonic esters include ethylene glycol dicrotonate, tetramethylene glycol dicrotonate, pentaerythritol dicrotonate, and sorbitol tetradicrotonate. Examples of isocrotonic esters include ethylene glycol diisocrotonate, pentaerythritol diisocrotonate, and sorbitol tetraisocrotonate. Examples of maleic esters include ethylene glycol dimaleate, triethylene glycol dimaleate, pentaerythritol dimaleate, and sorbitol tetramaleate.

Examples of other preferred esters include the aliphatic alcohol esters described in JP-B-51-47334 and JP-A-57-196231, the esters having an aromatic framework which are described in JP-A-59-5240, JP-A-59-5241, and JP-A-2-226149, and the esters having an amino group which are described in JP-A-1-165613. The ester monomers mentioned above can be used also as a mixture of two or more thereof.

Examples of the monomeric amide of an aliphatic polyamine compound with an unsaturated carboxylic acid include methylenebisacrylamide, methylenebismethacrylamide, 1,6-hexamethylenebisacrylamide, 1,6-hexamethylenebismethacrylamide, diethylenetriaminetrisacrylamide, xylylenebisacrylamide, and xylylenebismethacrylamide. Other preferred examples of the amide monomer include the amides having a cyclohexylene structure which are described in JP-B-54-21726.

An addition-polymerizable urethane compound produced by the addition reaction of an isocyanate with hydroxyl groups is also preferred. Examples of this compound include the vinyl urethane compounds having two or more polymerizable vinyl groups per molecule which are described in JP-B-48-41708. These vinyl urethane compounds are obtained by causing a hydroxyl-containing vinyl monomer represented by the following formula (a) to add to a polyisocyanate compound having two or more isocyanate groups per molecule.

$$CH_2=C(R_4)COOCH_2CH(R_5)OH \quad (a)$$

(In formula (a), $R_4$ and $R_5$ each represent H or $CH_3$.)

Furthermore, the urethane acrylates described in JP-A-51-37193, JP-B-2-32293, and JP-B-2-16765 and the urethane compounds having an ethylene oxide-based backbone which are described in JP-B-58-49860, JP-B-56-17654, JP-B-62-39417, and JP-B-62-39418 are also preferred. In addition, when any of the addition-polymerizable compounds having an amino structure or sulfide structure in the molecule which are described in JP-A-63-277653, JP-A-63-260909, and JP-A-1-105238 is used, a photopolymerizable composition having exceedingly high photosensitivity can be obtained.

Other examples of the polymerizable compound include polyfunctional acrylates or methacrylates, such as the polyester acrylates described in JP-A-48-64183, JP-B-49-43191, and JP-B-52-30490 and epoxy acrylates obtained by reacting an epoxy resin with (meth)acrylic acid. Examples thereof further include the specific unsaturated compounds described in JP-B-46-43946, JP-B-1-40337, and JP-B-1-40336 and the vinylphosphonic acid compound described in JP-A-2-25493. In some cases, the perfluoroalkyl-containing structure described in JP-A-61-22048 is advantageously used. Furthermore, the photocurable monomers and oligomers shown in Nihon Setchaku Kyôkai-shi, Vol. 20, No. 7, pp. 300-308 (1984) can be used.

Details of the structures of those polymerizable compounds and of methods of using these, e.g., as to whether the compounds are used alone or in combination and the amount of the compounds to be added, can be determined at will according to the performance design of the final lithographic printing plate precursor. For example, selections are made from the following standpoints.

From the standpoint of sensitivity, a structure having a larger amount of unsaturated bonds per molecule is preferred. In many cases, a structure having a functionality of 2 or higher is preferred. From the standpoint of enhancing the strength of image areas, i.e., cured film, a structure having a functionality of 3 or higher is preferred. To use a combination of compounds having different functionalities or different polymerizable groups (e.g., an acrylic ester, methacrylic ester, styrene compound, and vinyl ester compound) is an effective method for regulating both sensitivity and strength.

Furthermore, a selection of addition-polymerizable compounds and methods of using these are important factors which influence compatibility with and dispersibility in other ingredients in the image-recording layer (e.g., the binder polymer, initiator, colorant, etc.). For example, there are cases where use of a low-impurity compound or use of a combination of two or more compounds can improve compatibility. There also are cases where a specific structure is selected for the purpose of improving adhesion to the substrate or to the protective layer which will be described later, etc.

Those polymerizable compounds are used in an amount in the range of preferably 5-48% by mass, more preferably 10-45% by mass, based on all solid ingredients constituting the image-recording layer. Those compounds may be used alone or in combination of two or more thereof.

In addition, with respect to methods of using the polymerizable compounds, it is possible to freely select appropriate structures, proportions, and addition amounts from the standpoints of the degree of polymerization inhibition by oxygen, resolution, susceptibility to fogging, refractive index change, surface tackiness, etc. In some cases, a layer constitution/coating method including undercoating and overcoating is possible.

<Binder Polymer>

A binder polymer can be used in the image-recording layer in the invention in order to improve the film strength of the layer. Any of known binder polymers can be used without limitations. Polymers having film-forming properties are preferred. Examples of such binder polymers include acrylic resins, poly(vinyl acetal) resins, polyurethane resins, polyurea resins, polyimide resins, polyamide resins, epoxy resins, methacrylic resins, polystyrene resins, novolac type phenolic resins, polyester resins, synthetic rubbers, and natural rubber.

The binder polymer may have crosslinkability so as to improve the film strength of image areas. A binder polymer having crosslinkability can be obtained by incorporating crosslinkable functional groups such as, e.g., ethylenically unsaturated bonds into the main chain or side chains of a polymer. The crosslinkable functional groups may be incorporated by copolymerization.

Examples of polymers having ethylenically unsaturated bonds in the main chain of the molecule include poly(1,4-butandiene) and poly(1,4-isoprene).

Examples of polymers having ethylenically unsaturated bonds in side chains of the molecule include polymers of esters or amides of acrylic or methacrylic acid, in which the ester or amide residues (i.e., R in either —COOR or —CONHR) have an ethylenically unsaturated bond.

Examples of the residues (the R) having an ethylenically unsaturated bond include —$(CH_2)_nCR^1=CR^2R^3$, —$(CH_2O)_n CH_2CR^1=CR^2R^3$, —$(CH_2CH_2O)_n CH_2CR^1=CR^2R^3$, —$(CH_2)_nNH-CO-O-CH_2CR^1=CR^2R^3$, —$(CH_2)_n-O-CO-CR^1=CR^2R^3$, and —$(CH_2CH_2O)_2-X$ (wherein $R^1$ to $R^3$ each represent a hydrogen atom, a halogen atom, or an alkyl, aryl, alkoxy, or aryloxy group having 1 to 20 carbon atoms, provided that $R^1$ may be bonded to $R^2$ or $R^3$ to form a ring; n represents an integer of 1 to 10; and X represents a dicyclopentadienyl residue).

Examples of the ester residues include —$CH_2CH=CH_2$ (given in JP-B-7-21633), —$CH_2CH_2O-CH_2CH=CH_2$, —$CH_2C(CH_3)=CH_2$, —$CH_2CH=CH-C_6H_5$, —CH$_2$CH$_2$OCOCH=CH—C$_6$H$_5$, —CH$_2$CH$_2$—NH-COO—CH$_2$CH=CH$_2$, and —CH$_2$CH$_2$O—X (wherein X represents a dicyclopentadienyl residue).

Examples of the amide residues include —CH$_2$CH=CH$_2$, —CH$_2$CH$_2$—Y (wherein Y represents a cyclohexene residue), and —CH$_2$CH$_2$—OCO—CH=CH$_2$.

A binder polymer having crosslinkability cures, for example, by the following mechanism. Free radicals (polymerization initiator radicals or growth radicals which are radicals of a polymerizable compound which is polymerizing) add to crosslinkable functional groups of the binder polymer to cause addition polymerization directly between polymer molecules or through polymeric chains of the polymerizable compound. As a result, crosslinks are formed between polymer molecules, whereby the binder polymer cures. Alternatively, atoms in the polymer (e.g., hydrogen atoms bonded to the carbon atoms adjacent to the functional crosslinkable groups) are withdrawn by free radicals to yield polymer radicals, and these polymer radicals bond to one another to form crosslinks between polymer molecules, whereby the binder polymer cures.

The content of crosslinkable groups in the binder polymer (content of radical-polymerizable unsaturated double bonds as determined by iodometric titration) is preferably 0.1-10.0 mmol, more preferably 1.0-7.0 mmol, most preferably 2.0-5.5 mmol, per g of the binder polymer. When the content of crosslinkable groups is within this range, satisfactory sensitivity and satisfactory storage stability are obtained.

From the standpoint of improving the removability of unexposed areas of the image-recording layer in on-press development, the binder polymer preferably has high solubility or dispersibility in inks and/or fountain solutions.

In order for a binder polymer to have improved solubility or dispersibility in inks, it desirably is oleophilic. In order for a binder polymer to have improved solubility or dispersibility in fountain solutions, it desirably is hydrophilic. Because of this, it is also effective in the invention to use an oleophilic binder polymer and a hydrophilic binder polymer in combination.

Preferred examples of the hydrophilic binder polymer include binder polymers having hydrophilic groups such as hydroxy, carboxyl, carboxylate, hydroxyethyl, polyoxyethyl, hydroxypropyl, polyoxypropyl, amino, aminoethyl, aminopropyl, ammonium, amide, carboxymethyl, sulfo, or phosphate groups.

Specific examples thereof include gum arabic, casein, gelatin, starch derivatives, carboxymethyl cellulose and the sodium salt thereof, cellulose acetate, sodium alginate, vinyl acetate/maleic acid copolymers, styrene/maleic acid copolymers, poly(acrylic acid)s and salts thereof, poly(methacrylic acid)s and salts thereof, homopolymer and copolymers of hydroxyethyl methacrylate, homopolymer and copolymers of hydroxyethyl acrylate, homopolymer and copolymers of hydroxypropyl methacrylate, homopolymer and copolymers of hydroxypropyl acrylate, homopolymer and copolymers of hydroxybutyl methacrylate, homopolymer and copolymers of hydroxybutyl acrylate, polyethylene glycols, hydroxypropylene polymers, poly(vinyl alcohol)s, hydrolyzed poly(vinyl acetate) having a degree of hydrolysis of 60% by mole or higher, preferably 80% by mole or higher, poly(vinyl formal), poly(vinyl butyral), polyvinylpyrrolidone, homopolymer and copolymers of acrylamide, homopolymer and copolymers of methacrylamide, homopolymer and copolymers of N-methylolacrylamide, alcohol-soluble nylons, and polyethers of 2,2-bis(4-hydroxyphenyl)propane with epichlorohydrin.

The binder polymer has a mass-average molecular weight of preferably 5,000 or higher, more preferably 10,000, and a number-average molecular weight of preferably 1,000 or higher, more preferably 2,000. The polydispersity coefficient (mass-average molecular weight/number-average molecular weight) thereof is preferably 1.1-10.

The binder polymer can be synthesized by known methods. Examples of solvents usable for the synthesis include tetrahydrofuran, ethylene dichloride, cyclohexanone, methyl ethyl ketone, acetone, methanol, ethanol, ethylene glycol monomethyl ether, ethylene glycol monoethyl ether, 2-methoxyethyl acetate, diethylene glycol dimethyl ether, 1-methoxy-2-propanol, 1-methoxy-2-propyl acetate, N,N-dimethylformamide, N,N-dimethylacetamide, toluene, ethyl acetate, methyl lactate, ethyl lactate, dimethyl sulfoxide, and water. These may be used alone or as a mixture of two or more thereof.

A radical polymerization initiator may be used in synthesizing the binder polymer. As the initiator can be used any of known compounds such as azo initiators and peroxide initiators.

The content of the binder polymer may be 5-90% by mass and is preferably 5-80% by mass, more preferably 10-70% by mass, based on all solid components of the image-recording layer. When the binder polymer content is within this range, satisfactory image area strength and image-forming properties are obtained.

It is preferred that the polymerizable compound and the binder polymer be used in a proportion of from 0.5/1 to 4/1 in terms of mass ratio.

<Microcapsules>

For incorporating those ingredients for image-recording layer constitution and the other constituent ingredients which will be described later into an image-recording layer in the invention, several methods can be used. There are hence several embodiments of the image-recording layer. One embodiment of the image-recording layer is a molecule dispersion type image-recording layer formed by dissolving the constituent ingredients in an appropriate solvent and applying the solution, as described in, e.g., JP-A-2002-287334. Another embodiment is a microcapsule type image-recording layer which contains all or part of the constituent ingredients in a microencapsulated form, as described in, e.g., JP-A-2001-277740 and JP-A-2001-277742. In the microcapsule type image-recording layer, the constituent ingredients may be contained also outside the microcapsules. A preferred embodiment of the microcapsule type image-recording layer contains hydrophobic constituent ingredients in microcapsules and contains hydrophilic constituent ingredients outside the microcapsules. For obtaining better on-press developability, it is preferred to form the image-recording layer as a microcapsule type image-recording layer.

For microencapsulating ingredients for constituting the image-recording layer, known methods can be used. Examples of processes for microcapsule production include: the method utilizing coacervation as described in U.S. Pat. Nos. 2,800,457 and 2,800,458; the method based on interfacial polymerization as described in U.S. Pat. No. 3,287,154, JP-B-38-19574, and JP-B-42-446; the method based on polymer deposition as described in U.S. Pat. Nos. 3,418,250 and 3,660,304; the method using an isocyanate/polyol wall material as described in U.S. Pat. No. 3,796,669; the method using an isocyanate wall material as described in U.S. Pat. No. 3,914,511; the method using a urea-formaldehyde or urea-formaldehyde-resorcinol wall-forming material as described in U.S. Pat. Nos. 4,001,140, 4,087,376, and 4,089,802; the method using a wall material such as a melamine-formaldehyde resin or hydroxycellulose as described in U.S. Pat. No. 4,025,445; the in-situ method based on monomer polymerization as described in JP-B-36-9163 and JP-B-51-9079; the spray drying method as described in British Patent No. 930,422 and U.S. Pat. No. 3,111,407; and the electrolytic dispersion/cooling method as described in British Patents Nos. 952,807 and 967,074. However, usable methods for microencapsulation should not be construed as being limited to these examples.

Preferred microcapsule walls for use in the invention have three-dimensional crosslinks and have the property of swelling with solvents. From this standpoint, preferred materials of microcapsule walls are polyureas, polyurethanes, polyesters, polycarbonates, polyamides, and mixtures thereof. Especially preferred are polyureas and polyurethanes. A compound having a crosslinkable functional group capable of being incorporated into the binder polymer, such as, e.g., an ethylenically unsaturated bond, may be incorporated into microcapsule walls.

The average particle diameter of the microcapsules is preferably 0.01-3.0 µm, more preferably 0.05-2.0 µm, especially preferably 0.10-1.0 µm. When the average microcapsule diameter is within this range, satisfactory resolution and long-term stability are obtained.

<Other Components of Image-Recording Layer>

Various compounds can be further incorporated into the image-recording layer in the invention according to need. Such optional ingredients will be explained below.

<Surfactant>

A surfactant is preferably used for the image-recording layer in the invention in order to enhance on-press developability in printing initiation and to improve the state of coating surface. Examples of the surfactant include nonionic surfactants, anionic surfactants, cationic surfactants, amphoteric surfactants, and fluorochemical surfactants. Such surfactants may be used alone or in combination of two or more thereof.

The nonionic surfactants for use in the invention are not particularly limited, and known ones can be used. Examples thereof include polyoxyethylene alkyl ethers, polyoxyethylene alkylphenyl ethers, polyoxyethylene-polystyryl phenyl ethers, polyoxyethylene-polyoxypropylene alkyl ethers, partial fatty acid esters of glycerol, partial fatty acid esters of sorbitan, partial fatty acid esters of pentaerythritol, monoesters of fatty acids with propylene glycol, partial fatty acid esters of sucrose, partial fatty acid esters of polyoxyethylene-sorbitan, partial fatty acid esters of polyoxyethylene-sorbitol, polyethylene glycol/fatty acid esters, partial fatty acid esters of polyglycerol, polyoxyethylated castor oils, partial fatty acid esters of polyoxyethylene-glycerol, fatty acid diethanolamides, N,N-bis-2-hydroxyalkylamines, polyoxyethylene alkylamines, triethanolamine/fatty acid esters, trialkylamine oxides, polyethylene glycol, and copolymers of polyethylene glycol and polypropylene glycol.

The anionic surfactants for use in the invention are not particularly limited, and known ones can be used. Examples thereof include fatty acid salts, abietic acid salts, hydroxyalkanesulfonic acid salts, alkanesulfonic acid salts, dialkylsulfosuccinic acid salts, (linear alkyl)benzenesulfonic acid salts, (branched alkyl)benzenesulfonic acid salts, alkylnaphthalenesulfonic acid salts, alkylphenoxypolyoxyethylenepropylsulfonic acid salts, polyoxyethylene alkylsulfophenyl ether salts, N-methyl-N-oleyltaurine sodium salt, N-alkylsulfosuccinic acid monoamide disodium salts, petroleumsulfonic acid salts, sulfonated tallow oil, sulfuric acid ester salts of fatty acid alkyl esters, alkylsulfuric acid ester salts, polyoxyethylene alkyl ether sulfuric acid ester salts, fatty acid monoglyceride sulfuric acid ester salts, polyoxyethylene alkylphenyl ether sulfuric acid ester salts, polyoxyethylene styrylphenyl ether sulfuric acid ester salts, alkylphosphoric acid ester salts, polyoxyethylene alkyl ether phosphoric acid ester salts, polyoxyethylene alkylphenyl ether phosphoric acid ester salts, partially saponified styrene/maleic anhydride copolymers, partially saponified olefin/maleic anhydride copolymers, and naphthalenesulfonic acid salt/formalin condensates.

The cationic surfactants for use in the invention are not particularly limited, and known ones can be used. Examples thereof include alkylamine salts, quaternary ammonium salts, polyoxyethylene alkylamine salts, and polyethylene polyamine derivatives.

The amphoteric surfactants for use in the invention are not particularly limited, and known ones can be used. Examples thereof include carboxybetaines, aminocarboxylic acids, sulfobetaines, aminosulfuric acid esters, and imidazoline compounds.

In the surfactant names enumerated above, the term "polyoxyethylene" can be replaced by "polyoxyalkylene" such as polyoxymethylene, polyoxypropylene, or polyoxybutylene. These surfactants also can be used in the invention.

Other preferred examples of the surfactant include fluorochemical surfactants having a perfluoroalkyl group in the molecule. Examples of such fluorochemical surfactants include anionic ones such as perfluoroalkanecarboxylic acid salts, perfluoroalkanesulfonic acid salts, and perfluoroalkylphosphoric acid esters; amphoteric ones such as perfluoroalkyl betaines; cationic ones such as perfluoroalkyltrimethylammonium salts; and nonionic ones such as perfluoroalkylamine oxides, perfluoroalkyl ethylene oxide adducts, oligomers having a perfluoroalkyl group and a hydrophilic group, oligomers having a perfluoroalkyl group and an oleophilic group, oligomers having a perfluoroalkyl group, hydrophilic group, and oleophilic group, and urethanes having a perfluoroalkyl group and an oleophilic group. Furthermore, the fluorochemical surfactants described in JP-A-62-170950, JP-A-62-226143, and JP-A-60-168144 are also preferred.

Surfactants can be used alone or in combination of two or more thereof.

The content of the surfactant is preferably 0.001-10% by mass, more preferably 0.01-5% by mass, based on all solid components of the image-recording layer.

<Colorant>

Besides the ingredients described above, other various compounds may be added in the invention according to need. For example, a dye showing intense absorption in the visible light region can be used as a colorant for images. Examples thereof include Oil Yellow #101, Oil Yellow #103, Oil Pink #312, Oil Green BG, Oil Blue BOS, Oil Blue #603, Oil Black BY, Oil Black BS, and Oil Black T-505 (all manufactured by Orient Chemical Industries Ltd.), Victoria Pure Blue, Crystal Violet (CI 42555), Methyl Violet (CI 42535), Ethyl Violet, Rhodamine B (CI 145170B), Malachite Green (CI 42000), Methylene Blue (CI 52015), and the dyes shown in JP-A-62-293247. Furthermore, pigments such as phthalocyanine pigments, azo pigments, carbon black, and titanium oxide can also be advantageously used.

When those colorants are used, the image areas formed through image formation are easily distinguishable from the nonimage areas. There are hence cases where such a colorant is added as an auxiliary ingredient. The amount of the colorant to be added may be 0.01-10% by mass based on all solid components of the image-recording materials.

<Printing-Out Agent>

A compound which changes in color by the action of an acid or radical can be added to the image-recording layer in the invention in order to form a print-out image. As this compound can be effectively used various dyes such as, e.g., diphenylmethane, triphenylmethane, thiazine, oxazine, xanthene, anthraquinone, iminoquninone, azo, and azomethine dyes.

Examples thereof include dyes such as Brilliant Green, Ethyl Violet, Methyl Green, Crystal Violet, Basic Fuchsine, Methyl Violet 2B, Quinaldine Red, Rose Bengal, Metanil Yellow, Thymolsulfophthalein, Xylenol Blue, Methyl Orange, Paramethyl Red, Congo Red, Benzopurpurine 4B, α-Naphthyl Red, Nile Blue 2B, Nile Blue A, Methyl Violet, Malachite Green, Parafuchsine, Victoria Pure Blue BOH (manufactured by Hodogaya Chemical Co., Ltd.), Oil Blue #603 (manufactured by Orient Chemical Industries Ltd.), Oil Pink #312 (manufactured by Orient Chemical Industries Ltd.), Oil Red 5B (manufactured by Orient Chemical Industries Ltd.), Oil Scarlet #308 (manufactured by Orient Chemical Industries Ltd.), Oil Red OG (manufactured by Orient Chemical Industries Ltd.), Oil Red RR (manufactured by Orient Chemical Industries Ltd.), Oil Green #502 (manufactured by Orient Chemical Industries Ltd.), Spilon Red BEH Special (manufactured by Hodogaya Chemical Co., Ltd.), m-Cresol Purple, Cresol Red, Rhodamine B, Rhodamine 6G, Sulfo Rhodamine B, Auramine, 4-p-diethylaminophenyliminonaphthoquinone, 2-carboxyanilino-4-p-diethylaminophenyliminonaphthoquinone, 2-carboxystearylamino-4-p-N,N-bis(hydroxyethyl)aminophenyliminonaphthoquinone, 1-phenyl-3-methyl-4-p-diethylaminophenylimino-5-pyrazolone, and 1-β-naphthyl-4-p-diethylaminophenylimino-5-pyrazolone and leuco dyes such as p,p',p"-hexamethyltriaminotriphenylmethane (Leuco Crystal Violet) and Pergascript Blue SRB (manufactured by Ciba-Geigy Ltd.).

Besides those, the leuco dyes known as materials for heat-sensitive papers or pressure-sensitive papers are included in preferred examples. Specifically, examples thereof include crystal violet lactone, malachite green lactone, benzoyl leuco methylene blue, 2-(N-phenyl-N-methylamino)-6-(N-p-tolyl-N-ethyl)aminofluoran, 2-anilino-3-methyl-6-(N-ethyl-p-toluidino)fluoran, 3,6-dimethoxyfluoran, 3-(N,N-diethylamino)-5-methyl-7-(N,N-dibenzylamino)fluoran, 3-(N-cyclohexyl-N-methylamino)-6-methyl-7-anilinofluoran, 3-(N,N-diethylamino)-6-methyl-7-anilinofluoran, 3-(N,N-diethylamino)-6-methyl-7-xylidinofluoran, 3-(N,N-diethylamino)-6-methyl-7-chlorofluoran, 3-(N,N-diethylamino)-6-methoxy-7-aminofluoran, 3-(N,N-diethylamino)-7-(4-chloroanilino)fluoran, 3-(N,N-diethylamino)-7-chlorofluoran, 3-(N,N-diethylamino)-7-benzylaminofluoran, 3-(N,N-diethylamino)-7,8-benzofluoran, 3-(N,N-dibutylamino)-6-methyl-7-anilinofluoran, 3-(N,N-dibutylamino)-6-methyl-7-xylidinofluoran, 3-piperidino-6-methyl-7-anilinofluoran, 3-pyrrolidino-6-methyl-7-anilinofluoran, 3,3-bis(1-ethyl-2-methylindol-3-yl)phthalide, 3,3-bis(1-n-butyl-2-methylindol-3-yl)phthalide, 3,3-bis(p-dimethylaminophenyl)-6-dimethylaminophthalide, 3-(4-diethylamino-2-ethoxyphenyl)-3-(1-ethyl-2-methylindol-3-yl)-4-azaphthalide, and 3-(4-diethylaminophenyl)-3-(1-ethyl-2-methylindol-3-yl)phthalide.

The dye changing in color by the action of an acid or radical may be added to the image-recording layer in an amount of preferably 0.01-10% by mass based on the solid components of the layer.

<Polymerization Inhibitor>

A polymerization inhibitor is preferably added in a small amount to the image-recording layer in the invention in order to prevent the polymerizable compound from unnecessarily undergoing heat polymerization during the production or storage of the image-recording layer.

Preferred examples of the heat polymerization inhibitor include hydroquinone, p-methoxyphenol, di-t-butyl-p-cresol, pyrogallol, t-butylcatechol, benzoquinone, 4,4'-thiobis(3-methyl-6-t-butylphenol), 2,2'-methylenebis(4-methyl-6-t-butylphenol), and N-nitroso-N-phenylhydroxylamine aluminum salt.

The amount of the heat polymerization inhibitor is preferably about 0.01-5% by mass based on all solid components of the image-recording layer.

<Higher Fatty Acid Compound>

A higher fatty acid or a derivative thereof, such as behenic acid or behenamide, may be added to the image-recording layer in the invention so as to become present in a higher concentration in the image-recording layer surface during drying after coating, for the purpose of preventing the polymerization inhibition caused by oxygen. The amount of the higher fatty acid or derivative thereof to be added is preferably about from 0.1 to 10% by mass based on all solid components of the image-recording layer.

<Plasticizer>

The image-recording layer in the invention may contain a plasticizer so as to have improved on-press developability.

Examples of the plasticizer include phthalic esters such as dimethyl phthalate, diethyl phthalate, dibutyl phthalate, diisobutyl phthalate, dioctyl phthalate, octyl capryl phthalate, dicyclohexyl phthalate, ditridecyl phthalate, butyl benzyl phthalate, diisodecyl phthalate, and diallyl phthalate; glycol esters such as dimethyl glycol phthalate, ethyl phthalyl ethyl glycolate, methyl phthalyl ethyl glycolate, butyl phthalyl butyl glycolate, and triethylene glycol dicaprylate; phosphoric esters such as tricresyl phosphate and triphenyl phosphate; aliphatic dibasic acid esters such as diisobutyl adipate, dioctyl adipate, dimethyl sebacate, dibutyl sebacate, dioctyl azelate, and dibutyl maleate; and poly(glycidyl methacrylate), triethyl citrate, glycerol triacetyl ester, and butyl laurate.

The content of the plasticizer in the image-recording layer is preferably up to about 30% by mass based on all solid components of the image-recording layer.

<Fine Inorganic Particles>

The image-recording layer in the invention may contain fine inorganic particles for the purposes of improving cured-film strength in image areas and improving the removability of nonimage areas in on-press development.

Preferred examples of the fine inorganic particles include silica, alumina, magnesium oxide, titanium oxide, magnesium carbonate, calcium alginate, and mixtures thereof. Even though these particulate materials do not have the property of converting light to heat, they can be used for strengthening the film, enhancing interfacial adhesion by surface roughening, etc.

Such fine inorganic particles have an average particle diameter of preferably from 5 nm to 10 µm, more preferably 0.5-3 µm. When the fine inorganic particles have an average particle diameter within that range, the particles are stably dispersed in the image-recording layer to enable the image-recording layer to retain sufficient film strength and give nonimage areas which have excellent hydrophilicity and are less susceptible to scumming during printing.

The fine inorganic particles described above are easily available as commercial products, e.g., colloidal silica dispersions.

The content of the fine inorganic particles is preferably 40% by mass or lower, more preferably 30% by mass or lower, based on all solid components of the image-recording layer.

<Low-Molecular Hydrophilic Compound>

The image-recording layer in the invention may contain a hydrophilic low-molecular compound so as to have improved on-press developability. Examples of the hydrophilic low-molecular compound include the following water-soluble organic compounds: glycols such as ethylene glycol, diethylene glycol, triethylene glycol, propylene glycol, dipropylene glycol, and tripropylene glycol and ether or ester derivatives of these; polyhydroxy compounds such as glycerol and pentaerythritol; organic amines such as triethanolamine, diethanolamine, and monoethanolamine and salts of these; organic sulfonic acids such as toluenesulfonic acid and benzenesulfonic acid and salts of these; organic phosphonic acids such as phenylphosphonic acid and salts thereof; and organic carboxylic acids such as tartaric acid, oxalic acid, citric acid, malic acid, lactic acid, gluconic acid, and amino acids and salts of these.

<Formation of Image-Recording Layer>

The image-recording layer in the invention is formed by dispersing or dissolving the necessary ingredients in a solvent to prepare a coating fluid and applying the coating fluid. Examples of the solvent to be used here include ethylene dichloride, cyclohexanone, methyl ethyl ketone, methanol, ethanol, propanol, ethylene glycol monomethyl ether, 1-methoxy-2-propanol, 2-methyoxyethyl acetate, 1-methoxy-2-propyl acetate, dimethoxyethane, methyl lactate, ethyl lactate, N,N-dimethylacetamide, N,N-dimethylformamide, tetramethylurea, N-methylpyrrolidone, dimethyl sulfoxide, sulfolane, γ-butyrolactone, toluene, and water. However, the solvent should not be construed as being limited to these examples. These solvents may be used alone or as a mixture thereof. The solid concentration of the coating fluid is preferably 1-50% by mass.

It is also possible to form the image-recording layer according to the invention by dispersing or dissolving the same or different ingredients described above in the same or different solvents to prepare two or more coating fluids and repeatedly conducting application and drying operations.

The amount of the image-recording layer (on a dry basis) to be obtained on the support through application and drying varies depending on uses. In general, however, the amount thereof is preferably 0.3-3.0 g/m$^2$. When the image-recording layer amount is within this range, the image-recording layer has satisfactory sensitivity and satisfactory film properties.

For applying the coating fluid, various methods can be used. Examples thereof include bar coater coating, spin coating, spray coating, curtain coating, dip coating, air knife coating, blade coating, and roll coating.

[Protective Layer]

In the lithographic printing plate precursor of the invention, a protective layer can be formed according to need on the image-recording layer for the purposes of preventing the image-recording layer from suffering mars, shutting off oxygen, and preventing ablation in high-illuminance laser exposure.

In the invention, exposure is usually conducted in the air. The protective layer serves to prevent low-molecular compounds present in the air, such as, e.g., oxygen and basic substances, which inhibit the image-forming reaction caused in the image-recording layer by exposure, from coming into the image-recording layer to thereby prevent the image-forming reaction from being inhibited by exposure in the air. Consequently, the protective layer is desired to have the following properties: to have low permeability to low-molecular compounds including oxygen; to satisfactorily transmit the light to be used for exposure; to have excellent adhesion to the image-recording layer; and to be capable of being easily removed in an on-press development step after exposure. Various investigations have hitherto been made on protective layers having such properties. Such protective layers are described in detail in, e.g., U.S. Pat. No. 3,458,311 and JP-B-55-49729.

Examples of materials for the protective layer include water-soluble polymeric compounds having relatively excellent crystallinity. Specific examples thereof include water-soluble polymers such as poly(vinyl alcohol), polyvinylpyrrolidone, acid celluloses, gelatin, gum arabic, and poly(acrylic acid). Of these, poly(vinyl alcohol) (PVA), when used as the main component, gives most satisfactory results concerning basic properties such as oxygen barrier properties and removability in development. As long as the poly(vinyl alcohol) contains unsubstituted vinyl alcohol units, which impart the oxygen barrier properties and water solubility required of the protective layer, it may be one which has been partly substituted with an ester, ether, or acetal or may be one which partly has other comonomer units.

Examples of the poly(vinyl alcohol) include ones having a degree of hydrolysis of 71-100% by mole and a degree of polymerization in the range of 300-2,400. Specific examples thereof include PVA-105, PVA-110, PVA-117, PVA-117H, PVA-120, PVA-124, PVA-124H, PVA-CS, PVA-CST, PVA-HC, PVA-203, PVA-204, PVA-205, PVA-210, PVA-217, PVA-220, PVA-224, PVA-217EE, PVA-217E, PVA-220E, PVA-224E, PVA-405, PVA-420, PVA-613, and L-8, manufactured by Kuraray Co., Ltd.

Ingredients for the protective layer (selection of PVA, use of additives, etc.), the amount of the layer to be formed by coating, etc. are suitably selected while taking account of susceptibility to fogging, adhesion, marring resistance, and the like besides oxygen barrier properties and removability in development. In general, the higher the degree of hydrolysis of the PVA (i.e., the higher the content of unsubstituted vinyl alcohol units in the protective layer) and the larger the film thickness, the higher the oxygen barrier properties and the more the protective layer is preferred from the standpoint of sensitivity. Furthermore, it is preferred to regulate oxygen barrier properties so as not to be too high, in order to prevent an unnecessary polymerization reaction from occurring during production and storage and to prevent undesirable fogging, line thickening, or the like in imagewise exposure. Consequently, the oxygen permeability A as measured at 25° C. and 1 atm preferably satisfies 0.2<A<20 (mL/m$^2$ day).

It is preferred that an inorganic layer compound such as, e.g., that described in JP-A-11-38633 be incorporated into the protective layer in the invention. By using an inorganic layer compound in combination with the binder, satisfactory oxygen barrier properties can be obtained.

The inorganic layer compound to be used in the invention is in the form of particles each having a thin platy shape. Examples thereof include micas such as natural and synthetic micas represented by the formula $A(B,C)_{2-5}D_4O_{10}(OH,F,O)_2$ [wherein A is any of K, Na, and Ca; B and C each are any of Fe(II), Fe(III), Mn, Al, Mg, and V; and D is Si or Al], talc represented by the formula $3MgO·4SiO·H_2O$ taeniolite, montmorillonite, saponite, hectorite, and zirconium phosphate.

Of the micas, examples of the natural micas include commonmica, paragonite, phlogopite, biotite, and lepidolite.

Examples of the synthetic micas include nonswelling micas such as fluorophlogopite $KMg_3(AlSi_3O_{10})F_2$ and potassium tetrasilicic mica $KMg_{2.5}(Si_4O_{10})F_2$ and swelling micas such as sodium tetrasilicic mica $NaMg_{2.5}(Si_4O_{10})F_2$, sodium or lithium taeniolite $(Na,Li)Mg_2Li(Si_4O_{10})F_2$, and montmorillonite type sodium or lithium hectorite $(Na,Li)_{1/8}Mg_{2/5}Li_{1/8}(Si_4O_{10})F_2$. Synthetic smectite also is useful.

Of those inorganic layer compounds, the fluorinated swelling micas, which are synthetic inorganic layer compounds, are especially useful in the invention.

The shape of the inorganic layer compound to be used in the invention is as follows from the standpoint of controlling diffusion. The smaller the thickness thereof, the better. With respect to the planar size thereof, larger sizes are preferred as long as the layer compound impairs neither the flatness of the coating surface nor the transmission of actinic rays. Consequently, the aspect ratio thereof may be 20 or higher and is preferably 100 or higher, especially preferably 200 or higher. The aspect ratio of a particle is the ratio of the major-axis length to the thickness of the particle, and can be determined from projected images on photomicrographs of the particle. The higher the aspect ratio, the higher the effect obtained.

The particle diameter of the inorganic layer compound to be used in the invention may be 0.3-20 μm and is preferably 0.5-10 μm, especially preferably 1-5 μm, in terms of average major-axis length. The average thickness of the particles may be 0.1 μm or smaller and is preferably 0.05 μm or smaller, especially preferably 0.01 μm or smaller. For example, swelling synthetic micas, which are typical of inorganic layer compounds, have thicknesses of about 1-50 μm and planar sizes of about 1-20 μm.

The incorporation of such particles of an inorganic layer compound having a high aspect ratio in the protective layer improves coating film strength and can effectively prevent the permeation of oxygen and moisture. The layer compound hence prevents the protective layer from deteriorating through deformation, etc.

The amount of the inorganic layer compound to be contained in the protective layer may be 5-55% by mass based on all solid components of the protective layer. Preferably, the amount thereof is 1-40% by mass. In case where the amount of the compound is smaller than 5% by mass, the incorporation of the compound is ineffective in improving adhesion. In case where the amount thereof exceeds 55% by mass, coating film formation becomes insufficient, resulting in reduced sensitivity. When two or more inorganic layer compounds are used in combination, it is preferred that the sum of these inorganic layer compounds in terms of % by mass be within that range.

Other ingredients for the protective layer include the following. Glycerol, dipropylene glycol, or the like may be added in an amount of several percents by mass based on the (co)polymer to impart flexibility. Furthermore, an anionic surfactant such as a sodium alkyl sulfate or sodium alkylsulfonate, an amphoteric surfactant such as an alkylaminocarboxylic acid salt or alkylaminodicarboxylic acid salt, or a nonionic surfactant such as a polyoxyethylene alkylphenyl ether can be added in an amount of several percents by mass based on the (co)polymer.

The thickness of the protective layer is preferably 0.05-4 μm, especially preferably 0.1-2.5 μm.

The adhesion of the protective layer to the image areas and the marring resistance or the like of the protective layer are also significantly important in the handling of the lithographic printing plate precursor. This is because when a protective layer which comprises a water-soluble polymeric compound and is hence hydrophilic is superposed on the image-recording layer, which is hydrophobic, then the protective layer is apt to peel off due to insufficient adhesive force. There are cases where defects such as, e.g., film cure failures caused by polymerization inhibition by oxygen are developed in the areas from which the protective layer has peeled off.

Various proposals have been made on improvements of adhesion between an image-recording layer and a protective layer to eliminate such failures. For example, JP-A-49-70702 describes a technique in which a hydrophilic polymer consisting mainly of poly(vinyl alcohol) is mixed with 20 to 60% by mass acrylic emulsion, water-insoluble vinylpyrrolidone/vinyl acetate copolymer, or the like and this mixture is applied to an image-recording layer to form a layer thereon to thereby obtain sufficient adhesion. Any of such known techniques can be used in the invention. Coating methods for protective layer formation are described in detail in, e.g., U.S. Pat. No. 3,458,311 and JP-B-55-49729.

Other functions can be imparted to the protective layer. For example, a colorant which highly transmits infrared rays to be used for exposure and is capable of efficiently absorbing light having other wavelengths (e.g., a water-soluble dye) is added to thereby improve suitability for handling in safelight without causing a decrease in sensitivity.

[Support]

The support to be used in the lithographic printing plate precursor of the invention is not particularly limited as long as it is a platy material having dimensional stability. Examples thereof include paper, paper laminated with a plastic (e.g., polyethylene, polypropylene, or polystyrene), metal sheets (e.g., aluminum, zinc, and copper), plastic films (e.g., cellulose diacetate, cellulose triacetate, cellulose propionate, cellulose butyrate, cellulose acetate butyrate, cellulose nitrate, poly(ethylene terephthalate), polyethylene, polystyrene, polypropylene, polycarbonates, and poly(vinyl acetal)), and paper or plastic films to which any of those metals has been laminated or vapor-deposited. Preferred examples of the support include polyester films and aluminum sheets. Of these, aluminum sheets are preferred because they have satisfactory dimensional stability and are relatively inexpensive.

The aluminum sheets are sheets of pure aluminum, sheets of an alloy of aluminum as the main component with a slight amount of one or more other elements, or ones comprising a thin film of aluminum or an aluminum alloy and a plastic laminated thereto. Examples of the non-aluminum elements contained in the aluminum alloy include silicon, iron, manganese, copper, magnesium, chromium, zinc, bismuth, nickel, and titanium. The content of such non-aluminum elements in the alloy is preferably up to 10% by mass. Although a sheet of pure aluminum is preferred in the invention, an aluminum sheet containing a slight amount of non-aluminum elements may be used because completely pure aluminum is difficult to produce by the current refining technology.

The aluminum sheet to be used is not limited in composition and can be suitably selected from sheets of known aluminum materials in general use.

The thickness of the support is preferably 0.1-0.6 mm, more preferably 0.15-0.4 mm.

Before being used, the aluminum sheet is preferably subjected to a surface treatment such as a surface-roughening treatment or anodization treatment. Such a surface treatment facilitates the attainment of improved hydrophilicity and adhesion between an image-recording layer and the support. Before being subjected to a surface-roughening treatment, the aluminum sheet may be degreased according to need with a surfactant, organic solvent, alkaline aqueous solution, or the like to remove a rolling oil remaining on the surface thereof.

The surface-roughening treatment of the aluminum sheet may be conducted by various methods. Examples thereof include mechanical surface-roughening treatment, electrochemical surface-roughening treatment (surface-roughening treatment in which a surface layer is electrochemically dissolved away), and chemical surface-roughening treatment (surface-roughening treatment in which the surface is selectively dissolved away chemically).

For the mechanical surface-roughening treatment, known techniques can be used, such as ball polishing, brushing, blasting, and buffing. Furthermore, use may be made of a transfer method in which a roll having surface irregularities is used in an aluminum rolling step to transfer the irregularities to the aluminum sheet.

Examples of techniques for the electrochemical surface-roughening treatment include a method in which the aluminum sheet is treated in an electrolytic solution containing an acid, e.g., hydrochloric acid or nitric acid, while applying an alternating or direct current thereto. Examples thereof further include the method using a mixed acid as described in JP-A-54-63902.

The aluminum sheet which has undergone a surface-roughening treatment is subjected according to need to an alkali etching treatment with an aqueous solution of potassium hydroxide, sodium hydroxide, or the like and then to a neutralization treatment. Thereafter, the aluminum sheet may be subjected to an anodization treatment for enhancing wearing resistance according to need.

For the anodization treatment of the aluminum sheet, various electrolytes which enable the formation of a porous oxide film can be used. In general, sulfuric acid, hydrochloric acid, oxalic acid, chromic acid, or a mixture of two or more of these acids is used. The concentration of any of these electrolytes is suitably determined according to the kind of the electrolyte.

Conditions for the anodization treatment cannot be unconditionally specified because they vary over a wide range depending on the electrolyte to be used. In general, however, the conditions preferably include an electrolyte concentration in the solution of 1-80% by mass, solution temperature of 5-70° C., current density of 5-60 A/dm$^2$, voltage of 1-100 V, and electrolysis period of from 10 seconds to 5 minutes. The amount of the film to be formed by anodization is preferably 1.0-5.0 g/m$^2$, more preferably 1.5-4.0 g/m$^2$. When the amount of the film is within this range, satisfactory printing durability and the satisfactory marring resistance of nonimage areas of the lithographic printing plate are obtained.

The support to be used in the invention may be one which has undergone a surface treatment such as those shown above and has an anodized coating. Although this substrate may be used as it is, suitably selected treatments can be conducted according to need for the purpose of further improving adhesion to an upper layer, hydrophilicity, unsusceptibility to scumming, heat-insulating properties, etc. Examples of such treatments include the treatment for enlarging or filling micropores of an anodized coating as described in JP-A-2001-253181 and JP-A-2001-322365 and a surface-hydrophilizing treatment in which the support is immersed in an aqueous solution containing a hydrophilic compound. It is a matter of course that the pore-enlarging treatment and pore-filling treatment are not limited to those described in the documents, and any of known methods can be used.

For example, the pore-filling treatment can be conducted not only by pore filling with a vapor but also by a treatment with fluorozirconic acid alone, treatment with sodium fluoride, or pore filling with a vapor containing lithium chloride.

The pore-filling treatment to be used in the invention is not particularly limited and known methods can be used. Preferred of these are a pore-filling treatment with an aqueous solution containing an inorganic fluorine compound, a pore-filling treatment with water vapor, and a pore-filling treatment with hot water. These methods will be explained below.

Preferred examples of the inorganic fluorine compound to be used in the pore-filling treatment with an aqueous solution containing an inorganic fluorine compound include metal fluorides.

Specific examples thereof include sodium fluoride, potassium fluoride, calcium fluoride, magnesium fluoride, sodium fluorozirconate, potassium fluorozirconate, sodium fluorotitanate, potassium fluorotitanate, ammonium fluorozirconate, ammonium fluorotitanate, potassium fluorotitanate, fluorozirconic acid, fluorotitanic acid, hexafluorosilicic acid, nickel fluoride, iron fluoride, fluorophosphoric acid, and ammonium fluorophosphate. Preferred of these are sodium fluorozirconate, sodium fluorotitanate, fluorozirconic acid, and fluorotitanic acid.

The concentration of the inorganic fluorine compound in the aqueous solution is preferably 0.01% by mass or higher, more preferably 0.05% by mass or higher, from the standpoint of sufficiently filling micropores of the anodized coating, and is preferably 1% by mass or lower, more preferably 0.5% by mass or lower, from the standpoint of unsusceptibility to scumming.

The aqueous solution containing an inorganic fluorine compound preferably further contains a phosphoric acid salt compound. Use of the aqueous solution containing a phosphoric acid salt compound improves the hydrophilicity of the surface of the anodized coating and, hence, on-press developability and unsusceptibility to scumming can be improved.

Preferred examples of the phosphoric acid salt compound include phosphates of metals such as alkali metals and alkaline earth metals.

Specific examples thereof include zinc phosphate, aluminum phosphate, ammonium phosphate, diammonium hydrogen phosphate, ammonium dihydrogen phosphate, monoammonium phosphate, monopotassium phosphate, monosodium phosphate, potassium dihydrogen phosphate, dipotassium hydrogen phosphate, calcium phosphate, sodium ammonium hydrogen phosphate, magnesium hydrogen phosphate, magnesium phosphate, ferrous phosphate, ferric phosphate, sodium dihydrogen phosphate, sodium phosphate, disodium hydrogen phosphate, lead phosphate, diammonium phosphate, calcium dihydrogen phosphate, lithium phosphate, phosphotungstic acid, ammonium phosphotungstate, sodium phosphotungstate, ammonium phosphomolybdate, sodium phosphomolybdate, sodium phosphite, sodium tripolyphosphate, and sodium pyrophosphate. Preferred of these are sodium dihydrogen phosphate, disodium hydrogen phosphate, potassium dihydrogen phosphate, and dipotassium hydrogen phosphate.

Inorganic fluorine compound/phosphoric acid salt compound combinations are not particularly limited. It is, however, preferred that the aqueous solution should contain at least sodium fluorozirconate as the inorganic fluorine compound and further contain at least sodium dihydrogen phosphate as the phosphoric acid salt compound.

The concentration of the phosphoric acid salt compound in the aqueous solution is preferably 0.01% by mass or higher, more preferably 0.1% by mass or higher, from the standpoint of on-press developability and unsusceptibility to scumming, and is preferably 20% by mass or lower, more preferably 5% by mass or lower, from the standpoint of solubility.

Proportions of the compounds in the aqueous solution are not particularly limited. However, the ratio of the amount by mass of the inorganic fluorine compound to that of the phosphoric acid salt compound is preferably from 1/200 to 10/1, more preferably from 1/30 to 2/1.

The temperature of the aqueous solution is preferably 20° C. or higher, more preferably 40° C. or higher, and is preferably 100° C. or lower, more preferably 80° C. or lower.

The pH of the aqueous solution is preferably 1 or higher, more preferably 2 or higher, and is preferably 11 or lower, more preferably 5 or lower.

Methods for the pore-filling treatment with an aqueous solution containing an inorganic fluorine compound are not particularly limited. Examples thereof include the immersion method and spraying method. Any one of such methods may be used alone to conduct the treatment once or two or more times. Alternatively, two or more of such methods may be used in combination.

Preferred of these is the immersion method. In the case of using the immersion method to conduct the treatment, the treatment time is preferably 1 second or longer, more preferably 3 seconds or longer, and is preferably 100 seconds or shorter, more preferably 20 seconds or shorter.

Examples of the pore-filling treatment with water vapor include a method in which elevated- or ordinary-pressure water vapor is continuously or discontinuously brought into contact with the anodized coating.

The temperature of the water vapor is preferably 80° C. or higher, more preferably 95° C. or higher, and is preferably 105° C. or lower.

The pressure of the water vapor is preferably in the range of from [(atmospheric pressure)−50 mmAg] to [(atmospheric pressure)+300 mmAq] ($1.008 \times 10^5$–$1.043 \times 10^5$ Pa).

The time period in which water vapor is contacted is preferably 1 second or longer, more preferably 3 seconds or longer, and is preferably 100 seconds or shorter, more preferably 20 seconds or shorter.

Examples of the pore-filling treatment with hot water include a method in which the aluminum plate having an anodized coating is immersed in hot water.

The hot water may contain an inorganic salt (e.g., phosphoric acid salt) or an organic salt. The temperature of the hot water is preferably 80° C. or higher, more preferably 95° C. or higher, and is preferably 100° C. or lower.

The time period in which the anodized coating is immersed in hot water is preferably 1 second or longer, more preferably 3 seconds or longer, and is preferably 100 seconds or shorter, more preferably 20 seconds or shorter.

In the invention, a treatment for enlarging micropores of the anodized coating may be conducted, as described in JP-A-2001-322365, prior to the pore filling. Furthermore, a surface-hydrophilizing treatment may be performed after the pore filling.

Examples of the hydrophilizing treatment include an alkali metal silicate method such as those described in U.S. Pat. Nos. 2,714,066, 3,181,461, 3,280,734, and 3,902,734. In this method, the support is treated by immersion or electrolysis in an aqueous solution of sodium silicate or the like. Other examples of the hydrophilizing treatment include the method in which the support is treated with potassium fluorozirconate as described in JP-B-36-22063 and the method in which the support is treated with poly(vinylphosphonic acid) as described in U.S. Pat. Nos. 3,276,868, 4,153,461, and 4,689,272.

In the case where a support having insufficient surface hydrophilicity, such as, e.g., a polyester film, is used as the support in the invention, it is desirable to apply a hydrophilic layer thereto to hydrophilize the surface. The hydrophilic layer preferably is: the hydrophilic layer described in JP-A-2001-199175 formed by applying a coating fluid containing a colloid of an oxide or hydroxide of at least one element selected from beryllium, magnesium, aluminum, silicon, titanium, boron, germanium, tin, zirconium, iron, vanadium, antimony, and transition metals; the hydrophilic layer described in JP-A-2002-79772 which has an organic hydrophilic matrix obtained by the crosslinking or pseudocrosslinking of an organic hydrophilic polymer; a hydrophilic layer having an inorganic hydrophilic matrix obtained by sol-gel conversion comprising the hydrolysis/condensation reaction of a polyalkoxysilane, titanate, zirconate, or aluminate; or a hydrophilic layer comprising a thin inorganic film having a surface comprising a metal oxide. Preferred of these is the hydrophilic layer formed by applying a coating fluid containing a colloid of an oxide or hydroxide of silicon.

In the case of using a polyester film or the like as the support in the invention, it is preferred to form an antistatic layer on the hydrophilic-layer side or opposite side of this support or on each side. When an antistatic layer is disposed between the support and the hydrophilic layer, it contributes also to an improvement in adhesion between the support and the hydrophilic layer. As the antistatic layer can be used, for example, the polymer layer described in JP-A-2002-79772 which contains fine metal oxide particles or a matting agent dispersed therein.

The support to be used in the invention preferably has a center-line average surface roughness of 0.10-1.2 μm. When the surface roughness thereof is within this range, then satisfactory adhesion to the image-recording layer, satisfactory printing durability, and satisfactory unsusceptibility to scumming are obtained.

[Back Coat Layer]

A back coat can be formed on the back side of the support according to need after the support has undergone a surface treatment or after an undercoat layer has been formed.

Preferred examples of the back coat include a coating layer made of the organic polymeric compound described in JP-A-5-45885 or of the metal oxide obtained by hydrolyzing and condensation-polymerizing an organometallic compound or inorganic metal compound as described in JP-A-6-35174. Preferred of these materials are alkoxy compounds of silicon, such as $Si(OCH_3)_4$, $Si(OC_2H_5)_4$, $Si(OC_3H_7)_4$, and $Si(OC_4H_9)_4$. This is because starting materials for such silicon compounds are easily available at low cost.

[Undercoat Layer]

In the lithographic printing plate precursor of the invention, an undercoat layer may be disposed between the image-recording layer and the support according to need especially when the lithographic printing plate precursor is of the on-press development type. The undercoat layer serves to facilitate the removal of the image-recording layer from the support in unexposed areas and thereby improves on-press developability. Furthermore, in the case of exposure with an infrared laser, the undercoat layer functions as a heat-insulating layer, whereby the heat generated by the exposure does not diffuse to the support and is efficiently utilized. There is hence an advantage that sensitivity can be heightened.

Preferred examples of the undercoat layer include the silane coupling agent having an addition-polymerizable, ethylenic double-bond reactive group described in JP-A-10-282679 and the phosphorus compound having an ethylenic double-bond reactive group described in JP-A-2-304441.

Most preferred examples of the undercoat layer include a polymeric resin obtained by copolymerizing a monomer having an adsorbable group, a monomer having a hydrophilic group, and a monomer having a crosslinkable group.

An essential component of the polymeric undercoat is groups adsorbable onto hydrophilic support surfaces. Whether a compound has adsorbability onto hydrophilic support surfaces can be judged, for example, by the following method.

The test compound is dissolved in a good solvent therefor to prepare a coating fluid. This coating fluid is applied to a support in an amount of 30 mg/m² on a dry basis and dried. Subsequently, the support coated with the test compound is sufficiently washed with the good solvent. Thereafter, the amount of the test compound remaining unremoved after the washing is determined to calculate the amount of the test compound adsorbed to the support. In determining the residual compound amount, the compound amount may be directly determined or may be calculated through the determination of the amount of the test compound dissolved in the washings. The compound amount can be determined by, for example, fluorescent X-ray spectroscopy, reflection spectroscopy/absorptiometry, or liquid chromatography. A compound having adsorbability onto supports is a compound which remains in an amount of 1 mg/m² or larger even after the washing treatment.

The groups adsorbable onto hydrophilic support surfaces are functional groups capable of forming a chemical bond (e.g., an ionic bond, hydrogen bond, coordination bond, or bond by intermolecular force) with a substance (e.g., metal or metal oxide) or functional group (e.g., hydroxyl group) present on the hydrophilic support surfaces. The adsorbable groups preferably are acid groups or cationic groups.

The acid groups preferably have an acid dissociation constant ($pK_a$) of 7 or lower. Examples of the acid groups include phenolic hydroxyl, carboxyl, —$SO_3H$, —$OSO_3H$, —$PO_3H_2$, —$OPO_3H_2$, —$CONHSO_2$—, —$SO_2NHSO_2$—, and —$COCH_2COCH_3$. Especially preferred are the phosphoric acid groups (—$OPO_3H_2$ and —$PO_3H_2$). These acid groups may be metal salts.

The cationic groups preferably are onium salts. Examples of the onium salts include ammonium, phosphonium, arsonium, stibonium, oxonium, sulfonium, selenonium, stannonium, and iodonium groups. Preferred are ammonium, phosphonium, and sulfonium. More preferred are ammonium and phosphonium. Most preferred is ammonium.

Especially preferred examples of the monomer having an adsorbable group include compounds represented by the following formula (ii) or (iii).

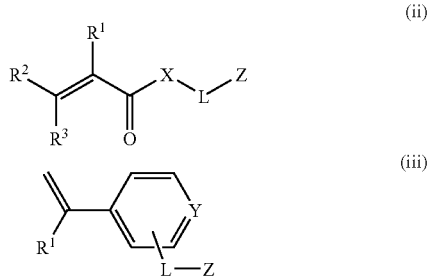

In formula (ii), $R^1$, $R^2$, and $R^3$ each independently represent a hydrogen atom, halogen atom, or alkyl group having 1-6 carbon atoms. $R^1$, $R^2$, and $R^3$ each independently preferably represent a hydrogen atom or an alkyl group having 1-6 carbon atoms, more preferably represent a hydrogen atom or an alkyl group having 1-3 carbon atoms, and most preferably represent a hydrogen atom or methyl. $R^2$ and $R^3$ especially preferably are hydrogen atoms.

In formula (ii), X is an oxygen atom (—O—) or imino (—NH—). X more preferably is an oxygen atom. In formula (ii), L is a divalent connecting group. L preferably is a divalent aliphatic group (alkylene, substituted alkylene, alkenylene, substituted alkenylene, alkynylene, or substituted alkynylene group), a divalent aromatic group (arylene or substituted arylene group), or a divalent heterocyclic group or is a combination of any of these groups with an oxygen atom (—O—), sulfur atom (—S—), imino (—NH—), substituted imino (—NR—, wherein R is an aliphatic, aromatic, heterocyclic group), or carbonyl (—CO—).

The aliphatic group may have a cyclic structure or a branched structure. The number of carbon atoms in the aliphatic group is preferably 1-20, more preferably 1-15, most preferably 1-10. The aliphatic group preferably is a saturated aliphatic group rather than an unsaturated aliphatic group. The aliphatic group may have one or more substituents. Examples of the substituents include halogen atoms, hydroxyl, aromatic groups, and heterocyclic groups.

The number of carbon atoms in the aromatic group preferably is 6-20, more preferably 6-15, most preferably 6-10. The aromatic group may have one or more substituents. Examples of the substituents include halogen atoms, hydroxyl, aliphatic groups, aromatic groups, and heterocyclic groups.

The heterocyclic group preferably comprises a 5-membered or 6-membered heterocycle. The heterocyclic group may comprise a heterocycle and, fused thereto, another heterocycle or an aliphatic or aromatic ring. The heterocyclic group may have one or more substituents. Examples of the substituents include halogen atoms, hydroxyl, oxo (=O), thioxo (=S), imino (=NH), substituted imino (=N—R, wherein R is an aliphatic, aromatic, or heterocyclic group), aliphatic groups, aromatic groups, and heterocyclic groups.

L preferably is a divalent connecting group comprising two or more polyoxyalkylene structures. More preferably, the polyoxyalkylene structures are polyoxyethylene structures. In other words, it is preferred that L comprise —($OCH_2CH_2$)$_n$— (n is an integer of 2 or larger).

In formula (ii), Z is a functional group capable of being adsorbed onto a hydrophilic support surface. Y is a carbon atom or nitrogen atom. When Y is a nitrogen atom and L is bonded to Y to form a quaternary pyridinium group, then Z is not essential because this group itself is adsorbable.

The adsorbable functional group is as described above.

Typical examples of the monomers represented by formula (ii) or (iii) are shown below.

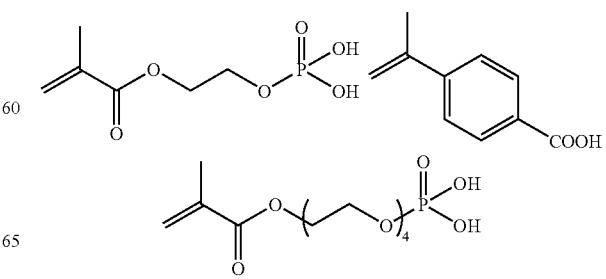

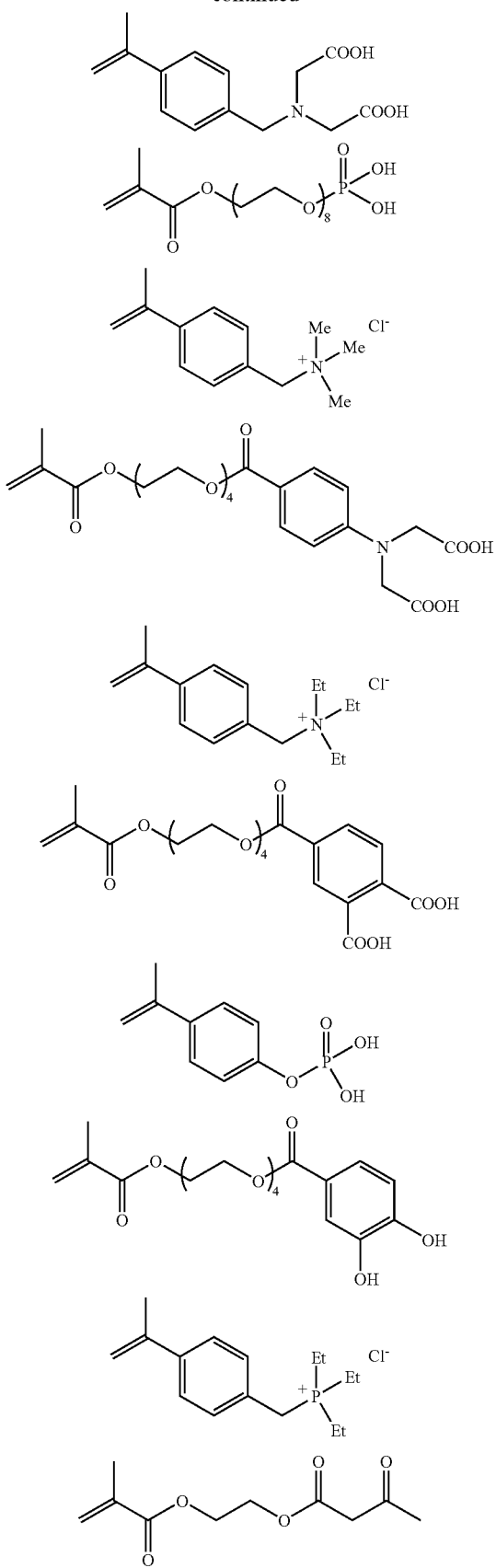

Preferred examples of the hydrophilic groups of the polymeric resin usable for undercoating in the invention include hydroxyl, carboxyl, carboxylate, hydroxyethyl, polyoxyethyl, hydroxypropyl, polyoxypropyl, amino, aminoethyl, aminopropyl, ammonium, amide, carboxymethyl, sulfo, and phosphate groups. A monomer having any of these hydrophilic groups and a polymerizable group is used as a comonomer ingredient for the polymeric resin.

The polymeric resin for undercoating in the invention preferably has crosslinkable groups. Crosslinkable groups improve adhesion to image areas. For imparting crosslinkability to the polymeric resin for undercoating, use may be made of a method in which crosslinkable functional groups such as, e.g., ethylenically unsaturated bonds are incorporated into side chains of the polymer. Alternatively, a method may be used in which a compound which has a substituent having a charge of the polarity opposite to that of the polar substituents of the polymeric resin and further has an ethylenically unsaturated bond is used to form a salt structure and thereby impart crosslinkability.

Examples of polymers having ethylenically unsaturated bonds in side chains of the molecule include a polymer which is a polymer of an ester or amide of acrylic or methacrylic acid and in which ester or amide residues (R in —COOR or —CONHR) have an ethylenically unsaturated bond.

Examples of the residues (the R) having an ethylenically unsaturated bond include —$(CH_2)_n CR_1$=$CR_2R_3$, —$(CH_2O)_n CH_2CR_1$=$CR_2R_3$, —$(CH_2CH_2O)_n CH_2CR_1$=$CR_2R_3$, —$(CH_2)_n NH$—CO—O—$CH_2CR_1$=$CR_2R_3$, —$(CH_2)_n$—O—CO—$CR_1$=$CR_2R_3$, and —$(CH_2CH_2O)_2$—X (wherein $R_1$ to $R_3$ each represent a hydrogen atom, a halogen atom, or an alkyl, aryl, alkoxy, or aryloxy group having 1-20 carbon atoms, provided that $R_1$ may be bonded to $R_2$ or $R_3$ to form a ring; n represents an integer of 1-10; and X represents a dicyclopentadienyl residue).

Examples of the ester residues include —$CH_2CH$=$CH_2$ (given in JP-B-7-21633), —$CH_2CH_2O$—$CH_2CH$=$CH_2$, —$CH_2C(CH_3)$=$CH_2$, —$CH_2CH$=$CH$—$C_6H_5$, —$CH_2CH_2OCOCH$=$CH$—$C_6H_5$, —$CH_2CH_2NHCOO$—$CH_2CH$=$CH_2$, and —$CH_2CH_2O$—X (wherein X represents a dicyclopentadienyl residue).

Examples of the amide residues include —$CH_2CH$=$CH_2$, —$CH_2CH_2O$—Y (wherein Y represents a cyclohexene residue), and —$CH_2CH_2OCO$—$CH$=$CH_2$.

The monomer having a crosslinkable group for the polymeric resin for undercoating preferably is an ester or amide of acrylic or methacrylic acid which has any of the crosslinkable groups shown above.

The content of crosslinkable groups in the polymeric resin for undercoating (the content of radical-polymerizable unsaturated bonds as determined by iodometric titration) is preferably 0.1-10.0 mmol, more preferably 1.0-7.0 mmol, most preferably 2.0-5.5 mmol, per g of the polymeric resin. When the crosslinkable-group content is within this range, satisfactory sensitivity and unsusceptibility to scumming are reconciled and satisfactory storage stability is obtained.

The polymeric resin for undercoating has a mass-average molecular weight of preferably 5,000 or higher, more preferably 10,000, and a number-average molecular weight of preferably 1,000 or higher, more preferably 2,000. The polydispersity coefficient (mass-average molecular weight/number-average molecular weight) thereof is preferably from 1.1 to 10.

The polymeric resin for undercoating may be any of a random polymer, block polymer, graft polymer, and the like. However, it preferably is a random polymer.

A known resin having hydrophilic groups may be used as the polymeric resin for undercoating in the invention. Examples of such resins include gum arabic, casein, gelatin, starch derivatives, carboxymethyl cellulose and the sodium salt thereof, cellulose acetate, sodium alginate, vinyl acetate/maleic acid copolymers, styrene/maleic acid copolymers, poly(acrylic acid)s and salts thereof, poly(methacrylic acid)s and salts thereof, homopolymer and copolymers of hydroxyethyl methacrylate, homopolymer and copolymers of hydroxyethyl acrylate, homopolymer and copolymers of hydroxypropyl methacrylate, homopolymer and copolymers of hydroxypropyl acrylate, homopolymer and copolymers of hydroxybutyl methacrylate, homopolymer and copolymers of hydroxybutyl acrylate, polyethylene glycols, hydroxypropylene polymers, poly(vinyl alcohol)s, hydrolyzed poly(vinyl acetate) having a degree of hydrolysis of 60% by mole or higher, preferably 80% by mole or higher, poly(vinyl formal), poly(vinyl butyral), polyvinylpyrrolidone, homopolymer and copolymers of acrylamide, homopolymer and copolymers of methacrylamide, homopolymer and copolymers of N-methylolacrylamide, alcohol-soluble nylons, and polyethers of 2,2-bis(4-hydroxyphenyl)propane with epichlorohydrin.

Polymeric resins for undercoating may be used alone or as a mixture of two or more thereof.

The amount of the undercoat layer to be formed (on a solid basis) is preferably 0.1-100 mg/m$^2$, more preferably 1-30 mg/m$^2$.

[Platemaking from Lithographic Printing Plate Precursor]

The lithographic printing plate precursor of the invention is imagewise exposed preferably with an infrared laser.

The infrared laser to be used in the invention is not particularly limited. However, preferred examples thereof include solid lasers and semiconductor lasers which emit infrared rays having a wavelength of 760-1,200 nm. The output of the infrared laser is preferably 100 mW or higher. For reducing the period of exposure, it is preferred to use a multi-beam laser device.

The exposure period for each pixel is preferably 20 μsec or shorter. The quantity of irradiation energy is preferably 10-300 mJ/cm$^2$.

After the lithographic printing plate precursor of the invention has undergone imagewise exposure with an infrared laser, it is used, without via any development step, to conduct printing while supplying an oil-based ink and an aqueous ingredient thereto.

Examples of methods for the process include: a method in which the lithographic printing plate precursor is exposed with an infrared laser and then mounted, without via a development step, on a printing machine to conduct printing; and a method in which the lithographic printing plate precursor is mounted on a printing machine, subsequently exposed with an infrared laser on the printing machine, and then used to conduct printing without via a development step.

When the lithographic printing plate precursor is imagewise exposed with an infrared laser and an aqueous ingredient and an oil-based ink are supplied to the exposed precursor to conduct printing without via a development step such as, e.g., a wet development step, then the image-recording layer in its exposed areas, which has been cured by the exposure, forms oil-based-ink-receiving parts having an oleophilic surface. On the other hand, in the unexposed areas, the uncured image-recording layer is dissolved or dispersed in the aqueous ingredient and/or oil-based ink supplied and is thus removed therewith to uncover the hydrophilic surface in these areas.

As a result, the aqueous ingredient adheres to the uncovered hydrophilic surface, while the oil-based ink adheres to the image-recording layer in the exposed areas to initiate printing. In this operation, the liquid to be supplied first to the plate surface may be either the aqueous ingredient or the oil-based ink. It is, however, preferred to supply the oil-based ink first from the standpoint of preventing the aqueous ingredient from being contaminated with those parts of the image-recording layer which are located in the unexposed areas. As the aqueous ingredient may be used an ordinary fountain solution for lithographic printing. According to the lithographic printing plate precursor of the invention, effects of the invention such as, e.g., stable ink receptibility during printing and high printing durability are obtained even with ordinary fountain solutions. It is a matter of course that the lithographic printing process of the invention, which will be described below, may be applied thereto. As the oil-based ink may be used an ordinary printing ink for lithographic printing.

The lithographic printing plate precursor is developed on an offset press in the manner described above and directly used for printing on many sheets.

[Lithographic Printing Process]

One of the lithographic printing process of the invention is characterized in that a lithographic printing plate precursor containing a phosphonium salt represented by formula (1) or (2) in the image-recording layer and/or protective layer is imagewise exposed, subsequently mounted on a printing machine without via a development step, and then used to conduct printing, or that the lithographic printing plate precursor is mounted on a printing machine, subsequently imagewise exposed, and then used to conduct printing.

The other lithographic printing process of the invention is characterized in that a fountain solution containing the phosphonium salt is used in on-press development. The other steps beginning with imagewise exposure and ending with printing can be conducted in the same manners as for the platemaking from the lithographic printing plate precursor. According to this lithographic printing process, effects of the invention such as, e.g., stable ink receptibility during printing are obtained even when a lithographic printing plate precursor not containing the phosphonium salt is used.

In the fountain solution according to the invention which contains the phosphonium salt, the ingredients given in, e.g., JP-A-5-112085 and JP-A-6-183171 can be suitably used besides the phosphonium salt.

For example, (a) a hydrophilic polymeric compound having film-forming properties is usable. Preferred examples thereof include cellulose derivatives such as hydroxyethyl cellulose, hydroxypropyl cellulose, methyl cellulose, hydroxypropyl methyl cellulose, hydroxybutyl methyl cellulose, and glyoxal modifications of these cellulose derivatives, the degree of substitution of each cellulose derivative being 20-90%. Especially preferred of these derivatives is hydroxypropyl cellulose. These derivatives may be used alone or in combination of two or more thereof. A preferred range of the amount of the cellulose derivatives to be used is 0.1-10% by mass.

Water-soluble polymeric compounds other than cellulose derivatives can be further used. Examples thereof include natural polymers and modifications thereof, such as gum arabic, starch derivatives (e.g., dextrin, dextrin obtained by enzymatic decomposition, hydroxypropylated dextrin obtained by enzymatic decomposition, carboxymethylated starch, starch phosphate, and starch octenylsuccinate), alginic acid salts, and cellulose derivatives (e.g., carboxymethyl cellulose, carboxyethyl cellulose, and methyl cellulose) and synthetic polymers such as polyethylene glycol and copolymers thereof, poly(vinyl alcohol) and derivatives thereof, polyvinylpyrrolidone, polyacrylamide and copolymers thereof, poly(acrylic acid) and copolymers thereof, vinyl methyl ether/maleic anhydride copolymers, vinyl acetate/maleic anhydride copolymers, and poly(styrenesulfonic acid) and copolymers thereof. These polymeric compounds may be used alone or as a mixture of two or more thereof. The concentration of such polymeric compounds in the fountain solution composition during use is desirably in the range of 0.005-1% by mass.

(b) A pH buffer is usable. Examples thereof include water-soluble organic acids and inorganic acids and salts thereof. A pH buffer is effective in the pH regulation or pH buffering of the fountain solution and in moderately etching a support for the lithographic printing plate or preventing the support from corroding. Preferred examples of the organic acids include citric acid, ascorbic acid, malic acid, tartaric acid, lactic acid, acetic acid, gluconic acid, hydroxyacetic acid, oxalic acid, malonic acid, maleic acid, levulinic acid, phytic acid, and organic phosphonic acids. Examples of the inorganic acids include phosphoric acid, nitric acid, and sulfuric acid. It is also preferred to use alkali metal salts, alkaline earth metal salts, ammonium salts, or organic amine salts of these organic acids and/or inorganic acids. These organic acids, inorganic acids, ad/or salts thereof may be used alone or in combination of two or more thereof. It is also possible to use alkali metal hydroxides, phosphoric acid, alkali metal salts, alkali metal carbonates, silicic acid salts, and the like.

(c) A compound for further improving the wettability of dampening rollers to realize stable water supply is usable. Examples thereof include propylene glycol, dipropylene glycol, tripropylene glycol, tetrapropylene glycol, propylene glycol monomethyl ether, dipropylene glycol monomethyl ether, tripropylene glycol monomethyl ether, tetrapropylene glycol monomethyl ether, propylene glycol monoethyl ether, dipropylene glycol monoethyl ether, tripropylene glycol monoethyl ether, tetrapropylene glycol monoethyl ether, propylene glycol monopropyl ether, dipropylene glycol monopropyl ether, tripropylene glycol monopropyl ether, tetrapropylene glycol monopropyl ether, propylene glycol monoisopropyl ether, dipropylene glycol monoisopropyl ether, tripropylene glycol monoisopropyl ether, tetrapropylene glycol monoisopropyl ether, propylene glycol monobutyl ether, dipropylene glycol monobutyl ether, tripropylene glycol monobutyl ether, tetrapropylene glycol monobutyl ether, propylene glycol monoisobutyl ether, dipropylene glycol monoisobutyl ether, tripropylene glycol monoisobutyl ether, tetrapropylene glycol monoisobutyl ether, propylene glycol mono-tert-butyl ether, dipropylene glycol mono-tert-butyl ether, tripropylene glycol mono-tert-butyl ether, tetrapropylene glycol mono-tert-butyl ether, and polypropylene glycols having a molecular weight of 200-1,000 and the monomethyl ethers, monoethyl ethers, monopropyl ethers, monoisopropyl ethers, and monobutyl ethers thereof. These compounds may be used alone or in combination of two or more thereof. The amount of such compounds to be used is preferably in the range of 10-70% by mass. Especially preferred of those compounds are ones whose 0.1-0.5% by mass aqueous solutions have a surface tension of 55 dyne/cm or lower.

(d) A compound useful in fountain solution concentration is usable. Examples thereof include 3-methoxybutanol, 3-ethoxybutanol, 3-propoxybutanol, 3-methyl-3-methoxybutanol, 3-methyl-3-ethoxybutanol, and 3-methyl-3-propoxybutanol. These compounds can be advantageously used either alone or in combination of two or more thereof. The amount of these compounds to be used is preferably in the range of 0.1-20% by mass.

(e) A compound effective in preventing the image areas of the printing plate from being deteriorated by solvent residues resulting from water evaporation is usable. Examples thereof include benzenesulfonic acid, p-toluenesulfonic acid, xylenesulfonic acid, cumenesulfonic acid, benzoic acid, salicylic acid, isophthalylsulfonic acid, gallic acid, phenolsulfonic acid, thiosalicylic acid, 4-(butylphenyl)-2-hydroxybenzenesulfonic acid, 4-(butylphenyl)benzenesulfonic acid, and (diphenyl ether)sulfonic acid. Furthermore, alkali metal salts (Na, K, and Li salts) and ammonium salts of these acids can be effectively used. The amount of these compounds to be used is preferably in the range of 0.01-7% by mass. These compounds may be used in combination of two or more thereof.

Besides the ingredients described above, a salt effective in preventing the corrosion of the printing plate and corrosion of metals used in the printing machine can be used. Examples thereof include sodium nitrate, potassium nitrate, ammonium nitrate, magnesium nitrate, calcium nitrate, beryllium nitrate, aluminum nitrate, zinc nitrate, zirconium nitrate, nickel nitrate, manganese nitrate, and chromium nitrate. These salts may be used alone or in combination of two or more thereof.

A surfactant may be further added. Examples of usable anionic surfactants include fatty acid salts, abietic acid salts, hydroxyalkanesulfonic acid salts, alkanesulfonic acid salts, dialkylsulfosuccinic acid salts, (linear alkyl)benzenesulfonic acid salts, (branched alkyl)benzenesulfonic acid salts, alkylnaphthalenesulfonic acid salts, alkylphenoxypolyoxyethylenepropylsulfonic acid salts, polyoxyethylene alkylsulfophenyl ether salts, N-methyl-N-oleyltaurine sodium salts, N-alkylsulfosuccinic acid monoamide disodium salt, petroleumsulfonic acid salts, sulfonated castor oil, sulfonated tallow oil, sulfuric acid ester salts of fatty acid alkyl esters, alkylsulfuric acid ester salts, polyoxyethylene alkyl ether sulfuric acid ester salts, fatty acid monoglyceride sulfuric acid ester salts, polyoxyethylene alkylphenyl ether sulfuric acid ester salts, polyoxyethylene styrylphenyl ether sulfuric acid ester salts, alkylphosphoric acid ester salts, polyoxyethylene alkyl ether phosphoric acid ester salts, polyoxyethylene alkylphenyl ether phosphoric acid ester salts, partly saponified styrene/maleic anhydride copolymers, partly saponified olefin/maleic anhydride copolymers, and naphthalenesulfonic acid salt/formalin condensates. Especially preferred of these are dialkylsulfosuccinic acid salts, alkylsulfuric acid ester salts, and alkylnaphthalenesulfonic acid salts.

Examples of usable nonionic surfactants include polyoxyethylene alkyl ethers, polyoxyethylene alkylphenyl ethers, polyoxyethylene-polystyryl phenyl ethers, polyoxyethylene-polyoxypropylene alkyl ethers, partial fatty acid esters of glycerol, partial fatty acid esters of sorbitan, partial fatty acid esters of pentaerythritol, fatty acid monoesters of propylene glycol, partial fatty acid esters of sucrose, partial fatty acid esters of polyoxyethylene-sorbitan, partial fatty acid esters of polyoxyethylene-sorbitol, fatty acid esters of polyethylene glycol, partial fatty acid esters of polyglycerol, polyoxyethylated castor oils, partial fatty acid esters polyoxyethylene-glycerol, fatty acid diethanolamides, N,N-bis-2-hydroxyalkylamines, polyoxyethylene alkylamines, fatty acid esters of triethanolamaine, and trialkylamine oxides. Fluorochemical surfactants and silicone surfactants are also usable. Preferred of these are polyoxyethylene alkylphenyl ethers, polyoxyethylene/polyoxypropylene block polymers, and the like.

Examples of usable cationic surfactants include alkylamine salts, quaternary ammonium salts, polyoxyethylene alkylamine salts, and polyethylene polyamine derivatives. The content of such surfactants is desirably 10% by mass or lower, preferably 0.01-3.0% by mass, from the standpoint of foaming.

It is preferred to use ethylene glycol, triethylene glycol, butylene glycol, hexylene glycol, octanediol, diethylene glycol, glycerol, trimethylolpropane, diglycerol, or the like as a wetting agent. These wetting agents may be used alone or in combination of two or more thereof. It is generally preferred to use the wetting agent in an amount of 0.1-25% by mass.

Furthermore, a chelate compound may be added to the fountain solution composition according to the invention. The fountain solution composition is usually used after having been diluted with tap water, well water, or the like. The calcium ions and other impurities contained in the tap water or well water used for the dilution may adversely influence printing and be causative of fouled printed matters. In such cases, this trouble can be eliminated by adding a chelate compound. Preferred examples of the chelate compound include ethylenediaminetetraacetic acid and the potassium salt and sodium salt thereof; diethylenetriaminepentaacetic acid and the potassium salt and sodium salt thereof; triethylenetetraminehexaacetic acid and the potassium salt and sodium salt thereof; hydroxyethylethylenediaminetriacetic acid and the potassium salt and sodium salt thereof; nitrilotriacetic acid and the sodium salt thereof; organic phosphonic acid compounds such as 1-hydroxyethane-1,1-diphosphonic acid and the potassium salt and sodium salt thereof and aminotri(methylenephosphonic acid) and the potassium salt and sodium salt thereof; and phosphonoalkanetricarboxylic acids. Also effective are organic amine salts, in place of sodium salts or potassium salts, of these chelating agents. A chelating agent which is stably present in the fountain solution composition and does not adversely influence printing is selected from those chelating agents.

A rust preventive may be used in the fountain solution composition according to the invention. Examples thereof include benzotriazole, 5-methylbenzotriazole, 5-methoxybenzotriazole, 4-chlorobenzotriazole, 4-bromobenzotriazole, 4-bromo-6-methylbenzotriazole, and 4-bromo-6-trifluoromethylbenzotriazole. Examples thereof further include the compounds formed by replacing the 1-position hydrogen atom of those compounds by an alkali metal (K, Na, or Li) or $NH_4$, benzimidazole and derivatives thereof, mercapto compounds and/or thioether compounds such as mercaptoacetic acid, 2-mercaptopropionic acid, 3-mercaptopropionic acid, 4-mercaptobutanoic acid, 2,4-dimercaptobutanoic acid, 2-mercaptotetradecanoic acid, 2-mercaptomyristic acid, mercaptosuccinic acid, 2,3-dimercaptosuccinic acid, cysteine, N-acetylcysteine, N-(2-mercaptopropionyl)glycine, N-(2-mercapto-2-methylpropionyl)glycine, N-(3-mercaptopropionyl)glycine, N-(2-mercapto-2-methylpropionyl)cysteine, penicillamine, N-acetylpenicillamine, glycine/cysteine/glutamine condensates, N-(2,3-dimercaptopropionyl)glycine, 2-mercaptonicotinic acid, thiosalicylic acid, 3-mercaptobenzoic acid, 4-mercaptobenzoic acid, 3-carboxy-2-mercaptopyridine, 2-mercaptobenzothiazole-5-carboxylic acid, 2-mercapto-3-phenylpropanoic acid, 2-mercapto-5-carboxyethylimidazole, 5-mercapto-1-(4-carboxyphenyl)tetrazole, N-(3,5-dicarboxyphenyl)-2-mercaptotetrazole, 2-(1,2-dicarobxyethylthio)-5-mercapto-1,3,5-thiadiazole, 2-(5-mercapto-1,3,4-thiadiazolylthio) hexanoic acid, 2-mercaptoethanesulfonic acid, 2,3-dimercapto-1-propanesulfonic acid, 2-mercaptobeneznesulfonic acid, 4-mercaptobenzenesulfonic acid, 3-mercapto-4-(2-sulfophenyl)-1,2,4-triazole, 2-mercaptobenzothiazole-5-sulfonic acid, 2-mercaptobenzimidazole-6-sulfonic acid, mercaptosuccinimide, 4-mercaptobenzenesulfonamide, 2-mercaptobenzimidazole-5-sulfonamide, 3-mercapto-4-(2-(methylaminosulfonyl)ethoxy) toluene, 3-mercapto-4-(2-(methylsulfonylamino)ethoxy) toluene, 4-mercapto-N-(p-methylphenylsulfonyl) benzamide, 4-mercaptophenol, 3-mercaptophenol, 2-mercaptophenol, 3,4-dimercarptotoluene, 2-mercaptohydroquinone, 2-thiouracil, 3-hydroxy-2-mercaptopyridine, 4-hydroxythiophenol, 4-hydroxy-2-mercaptopyrimidine, 4,6-dihydroxy-2-mercaptopyrimidine, 2,3-dihydroxypropyl mercaptan, 2-mercapto-4-octylphenyl methanesulfonylaminoethyl ether, 2-mercapto-4-octylphenol methaneaminosulfonylbutyl ether, thiodiglycolic acid, thiodiphenol, 6,8-dithiooctanoic acid, 5-methoxy-2-mercaptobenzimidazole, 2-mercaptobenzimidazole-5-sulfonic acid, and alkali metal salts, alkaline earth metal salts, ammonium salts, and organic amine salts of these compounds. The content of those compounds is preferably in the range of 0.0001-5% by mass. Those compounds may be used alone or as a mixture of two or more thereof.

Various colorants, antifoamers, and antiseptics and the like can be further added to the fountain solution composition according to the invention. For example, dyes for foods can be advantageously used as the colorants. Examples thereof include yellow dyes such as C.I. Nos. 19140 and 15985, red dyes such as C.I. Nos. 16185, 45430, 16255, 45380, and 45100, violet dyes such as C.I. No. 42640, blue dyes such as C.I. Nos. 42090 and 73015, and green dyes such as C.I. No. 42095. Preferred antifoamers are silicone antifoamers. The silicone antifoamers are of the emulsion/dispersion type, solution type, etc., and any of these is usable. An optimal range of the addition amount thereof is from 0.001-1% by mass.

Examples of the antiseptics include phenol and derivatives thereof, formalin, imidazole derivatives, sodium dehydroacetate, 4-isothiazolin-3-one derivatives, benzotriazole derivatives, derivatives of amidine or guanidine, quaternary ammonium salts, derivatives of pyridine, quinoline, or guanidine, derivatives of diazines or triazoles, and derivatives of oxazole or oxazine.

The ingredients described above are dissolved in water, preferably in desalted water, i.e., pure water, to give an aqueous solution. Thus, the fountain solution composition for use in the invention is obtained. When a concentrate is used, it is preferred from the standpoint of profitability that the concentrate be diluted 10-100 times with tap water, well water, or the like before use.

EXAMPLES

The invention will be explained below by reference to Examples, but the invention should not be construed as being limited to the following Examples.

1. Production of Support

An aluminum sheet (material, 1050) having a thickness of 0.3 mm was subjected to a degreasing treatment with 10% by mass aqueous sodium aluminate solution at 50° C. for 30 seconds in order to remove the rolling oil remaining on the surface thereof. Thereafter, the aluminum surface was grained with three brushes having nylon bundles set therein having a bristle diameter of 0.3 mm and with an aqueous suspension of pumice having a median diameter of 25 μm (specific gravity of the suspension, 1.1 g/cm³), and then sufficiently washed with water. This sheet was immersed for 9 seconds in 25% by mass aqueous sodium hydroxide solution having a temperature of 45° C. to conduct etching and then washed with water. Thereafter, the sheet was immersed in 20% by mass nitric acid at 60° C. for 20 seconds and washed with water. In this operation, the amount of the grained surface layer removed by etching was about 3 g/m².

Subsequently, an electrochemical surface-roughening treatment was continuously conducted using a 60-Hz AC voltage. The electrolytic solution used for this treatment was 1% by mass aqueous nitric acid solution (containing 0.5% by mass aluminum ions) and the temperature of the solution was 50° C. The AC power source used was one providing a trapezoidal rectangular wave alternating current wherein the TP, which is the time required for the current value to increase from zero to a peak, was 0.8 msec and the duty ratio was 1:1. A carbon electrode was used as a counter electrode to conduct the electrochemical surface-roughening treatment using ferrite as an auxiliary anode. The current density was 30 A/dm² in terms of peak value. To the auxiliary anode was supplied 5% of the current flowing from the power source. The quantity of electricity in the nitric acid electrolysis was 175 C/dm² in terms of the quantity of electricity at the time when the aluminum sheet was functioning as an anode. After this treatment, the aluminum sheet was washed with water by spraying.

Thereafter, an electrochemical surface-roughening treatment with an electrolytic solution consisting of 0.5% by mass aqueous hydrochloric acid solution (containing 0.5% by mass aluminum ions) and having a temperature of 50° C. was conducted under the conditions of a quantity of electricity of 50 C/dm² at the time when the aluminum sheet was functioning as an anode, in the same manner as in the nitric acid electrolysis. The sheet was then water-washed by spraying. This sheet was subjected to direct-current anodization at a current density of 15 A/dm² using 15% by mass sulfuric acid (containing 0.5% by mass aluminum ions) as an electrolytic solution to deposit an anodized coating in an amount of 2.5 g/m², subsequently washed with water, and dried. The resultant support is referred to as support A. This substrate was examined for center-line average surface roughness (Ra) with a pointer having a diameter of 2 μm. As a result, the average surface roughness thereof was found to be 0.51 μm.

The following undercoating fluid (1) was applied to the support in an amount of 6 mg/m² on a dry basis to form an undercoat layer comprising a water-soluble polymer. Thus, undercoated supports for use in the following experiments were produced.

| Undercoating Fluid (1) | |
|---|---|
| Undercoating compound (1) | 0.017 g |
| Methanol | 9.00 g |
| Water | 1.00 g |

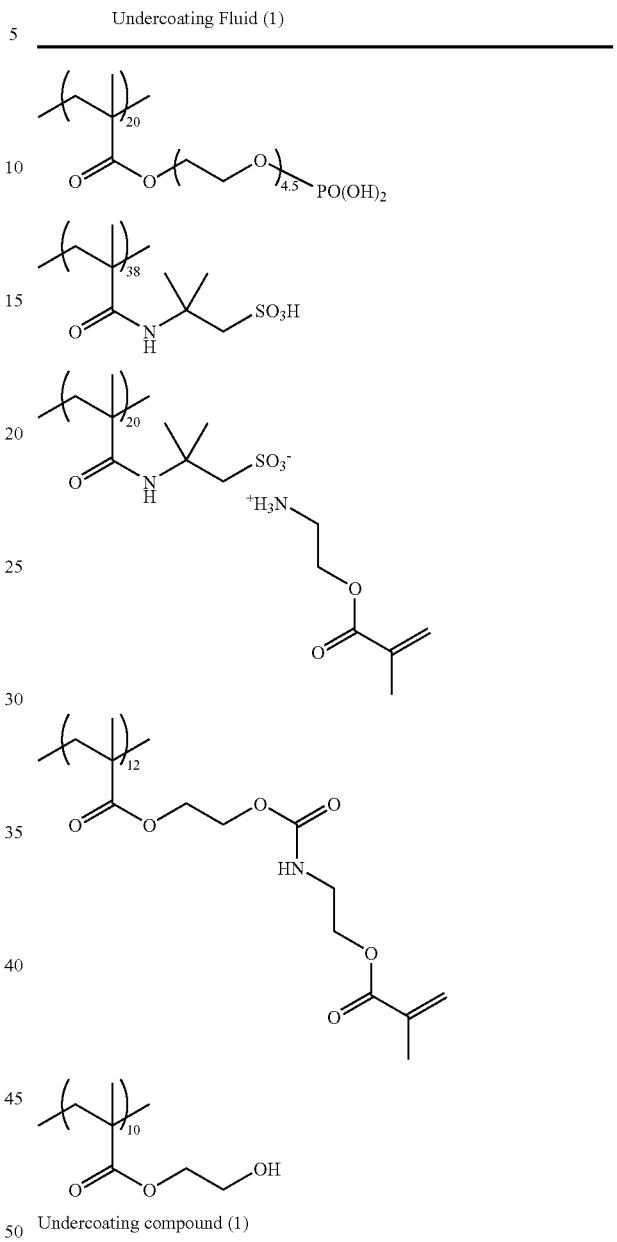

Undercoating compound (1)

2. Production of Lithographic Printing Plate Precursors

Examples 1 to 6

An image-recording-layer coating fluid (1) which had the following composition was applied by bar coating on the support having an undercoat layer and then dried in an oven at 100° C. for 60 seconds to form an image-recording layer in an amount of 1.0 g/m² on a dry basis. The image-recording-layer coating fluid (1) was obtained, just before application, by mixing the following photosensitive liquid (1) with the following microcapsule suspension (1) and stirring the mixture.

| Photosensitive Liquid (1) | |
|---|---|
| Binder polymer (1) | 0.162 g |
| Polymerization initiator (1) | 0.160 g |
| Polymeerization initiator (2) | 0.180 g |
| Infrared absorber (1) | 0.020 g |
| Polymerizable compound Aronix M-215 (manufactured by Toagosei Co., Ltd.) | 0.385 g |
| Fluorochemical surfactant (1) | 0.044 gg |
| Methyl ethyl ketone | 1.091 g |
| 1-Methoxy-2-propanol | 8.210 g |
| Phosphonium salt shown in Table 1 | Amount shown in Table 1 |
| Microcapsule Suspension (1) | |
| Microcapsules (1) synthesized in the manner shown below | 2.640 g |
| Water | 2.425 g |

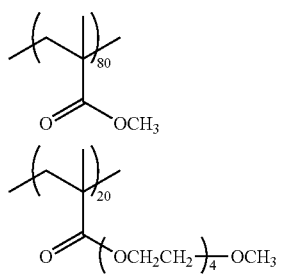

Binder polymer (1)

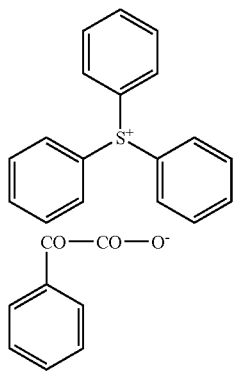

Polymerization initiator (1)

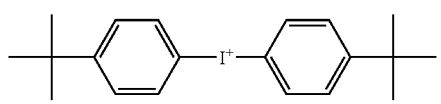

Polymerization initiator (2)

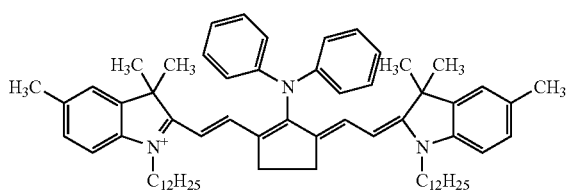

Infrared absorber (1)

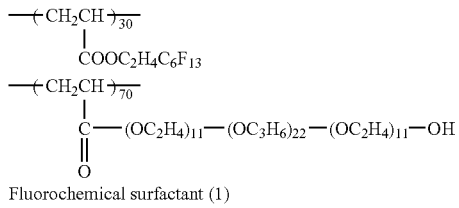

Fluorochemical surfactant (1)

Synthesis of Microcapsules (1)

In 16.67 g of ethyl acetate were dissolved 10 g of a trimethylolpropane/xylene diisocyanate adduct (Takenate D-110N, manufactured by Mitsui Takeda Chemicals, Inc.; 75% by mass ethyl acetate solution), 6.00 g of Aronix SR-399 (manufactured by Toagosei Co., Ltd.), and 0.12 g of Pionin A-41C (manufactured by Takemoto Oil & Fat Co., Ltd.). Thus, an oily-phase ingredient was prepared. On the other hand, a 4% by mass aqueous solution of PVA-205 was prepared as an aqueous-phase ingredient in an amount of 37.5 g. The oily-phase ingredient was mixed with the aqueous-phase ingredient, and this mixture was emulsified by treatment with a homogenizer at 12,000 rpm for 10 minutes. The emulsion obtained was added to 25 g of distilled water, and this mixture was stirred at room temperature for 30 minutes and then at 40° C. for 2 hours. The microcapsule suspension thus obtained was diluted with distilled water so as to result in a solid concentration of 15% by mass. The average particle diameter of the microcapsules was 0.2 μm.

The protective-layer coating fluid (1) shown below was applied on the image-recording layer by bar coating and then dried in an oven at 125° C. for 75 seconds to form a protective layer in an amount of 0.15 g/m² on a dry basis. Thus, a lithographic printing plate precursor was obtained.

| Protective-Layer Coating Fluid (1) | |
|---|---|
| Poly(vinyl alcohol) (PVA 105, manufactured by Kuraray Co., Ltd.; degree of saponification, 98.5 mol %; degree of polymerization, 500) 6% by mass aqueous solution | 2.24 g |
| Polyvinylpyrrolidone (K30) | 0.0053 g |
| Surfactant (Emalex 710, manufactured by Kao Corp.) 1% by mass aqueous solution | 2.15 g |
| Flaky synthetic mica (MEB 3L, manufactured by UNICOO Co., Ltd.; average particle diameter, 1-5 μmφ) 3.4% by mass aqueous dispersion | 3.75 g |
| Distilled water | 10.60 g |

Examples 7 to 12

An image-recording-layer coating fluid (2) which had the following composition was applied by bar coating on the support having an undercoat layer and then dried in an oven at 100° C. for 60 seconds to form an image-recording layer in an amount of 1.3 g/m² on a dry basis. Furthermore, a protective layer was formed in the same manner as in Example 1 to obtain a lithographic printing plate precursor.

The image-recording-layer coating fluid (2) was obtained, just before application, by mixing the following photosensitive liquid (2) with the microcapsule suspension (1) and stirring the mixture.

| Photosensitive Liquid (2) | |
|---|---|
| Binder polymer (1) | 0.162 g |
| Polymerization initiator (3) | 0.180 g |
| Infrared absorber (2) | 0.038 g |
| Polymerizable compound Aronix M-215 (manufactured by Toagosei Co., Ltd.) | 0.385 g |
| Fluorochemical surfactant (1) | 0.044 g |
| Methyl ethyl ketone | 1.091 g |

-continued

| Photosensitive Liquid (2) | |
|---|---|
| 1-Methoxy-2-propanol | 8.210 g |
| Phosphonium salt shown in Table 1 | Amount shown in Table 1 |

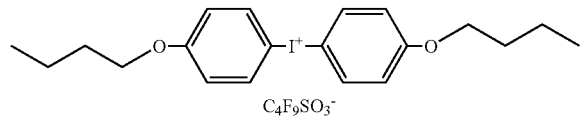

C4F9SO3-

Polymerization initiator (3)

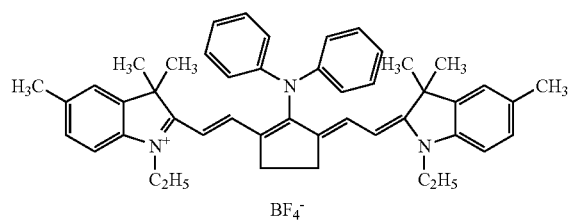

BF4-

Infrared absorber (2)

Comparative Example 1

A lithographic printing plate precursor for comparison was obtained in the same manner as in Example 1, except that the phosphonium salt in the photosensitive liquid (1) was omitted.

Comparative Example 2

A lithographic printing plate precursor for comparison was obtained in the same manner as in Example 7, except that the phosphonium salt in the photosensitive liquid (2) was omitted.

Example 13

The protective-layer coating fluid (2) shown below was applied on the same image-recording layer as in Comparative Example 2 by bar coating and then dried in an oven at 125° C. for 75 seconds to form a protective layer in an amount of 0.15 g/m² on a dry basis. Thus, a lithographic printing plate precursor was obtained.

| Protective-Layer Coating Fluid (2) | |
|---|---|
| Poly(vinyl alcohol) (PVA 105, manufactured by Kuraray Co., Ltd.; degree of saponification, 98.5 mol %; degree of polymerization, 500) 6% by mass aqueous solution | 2.24 g |
| Polyvinylpyrrolidone (K30) | 0.0053 g |
| Surfactant (Emalex 710, manufactured by Kao Corp.) 1% by mass aqueous solution | 2.15 g |
| Flaky synthetic mica (MEB 3L, manufactured by UNICOO Co., Ltd.; average particle diameter, 1-5 μmφ) 3.4% by mass aqueous dispersion | 3.75 g |
| Phosphonium compound (P-8) | 0.20 g |
| Distilled water | 10.60 g |

3. Evaluation of Lithographic Printing Plate Precursors

The lithographic printing plate precursors obtained above were examined and evaluated for on-press developability and printing durability by the following methods. The results obtained are shown in Table 1.

<On-Press Developability>

Each of the lithographic printing plate precursors obtained was exposed with Trendsetter 3244VX, manufactured by Creo Co., Ltd. and equipped with a 40-W infrared semiconductor laser of the water cooling type. The exposure was conducted under the conditions of an output of 9.6 W, outer-drum rotational speed of 150 rpm, and resolution of 2,400 dpi. The exposed plate precursor was attached to the cylinder of printing machine SOR-M, manufactured by Heidelberg. A fountain solution [Ecolity 2 (etchant manufactured by Fuji Photo Film Co., Ltd.)/water=2/98 (volume ratio)] and black ink TRANS-G(N) (manufactured by Dainippon Ink & Chemicals, Inc.) were supplied thereto. Thereafter, printing was conducted on 100 sheets at a printing speed of 6,000 sheets per hour. The number of sheets of printing paper required before the unexposed areas of the image-recording layer were completely removed by development on the printing machine and came not to transfer the ink to the printing paper was counted as a measure of on-press developability.

<Printing Durability>

After the evaluation of on-press developability, printing was further continued. As the number of printed sheets increased, the ink density in the printing paper decreased. Printing durability was evaluated in terms of the number of printed sheets required for the ink density (reflection density) to decrease by 0.1 from the density as measured at printing initiation.

TABLE 1

| | Phosphonium salt | Amount of addition to photosensitive liquid (g) | On-press developability (number of sheets) | Printing durability (number of sheets) |
|---|---|---|---|---|
| Example 1 | P-1 | 0.032 | 30 | 5500 |
| Example 2 | P-3 | 0.04 | 28 | 6000 |
| Example 3 | P-7 | 0.062 | 19 | 6500 |
| Example 4 | P-8 | 0.05 | 15 | 7000 |
| Example 5 | P-9 | 0.068 | 17 | 6800 |
| Example 6 | P-11 | 0.072 | 20 | 6300 |
| Comparative Example 1 | no addition | | 30 | 3000 |
| Example 7 | P-1 | 0.032 | 32 | 6000 |
| Example 8 | P-4 | 0.041 | 30 | 6200 |
| Example 9 | P-6 | 0.042 | 25 | 6000 |
| Example 10 | P-5 | 0.048 | 30 | 5800 |
| Example 11 | P-14 | 0.038 | 20 | 6200 |
| Example 12 | P-8 | 0.05 | 16 | 6800 |
| Comparative Example 2 | no addition | | 32 | 1000 |
| Example 13 | P-8 | 0.20 (*1) | 19 | 6500 |

(*1)addition to protective-layer coating fluid

The following can be seen from Table 1. As compared with the lithographic printing plate precursors heretofore in use (Comparative Examples 1 and 2), the lithographic printing plate precursors of the invention attain highly excellent printing durability (ink receptibility) while retaining on-press developability. Furthermore, as apparent from Examples 1 to 6 and Examples 7 to 12, the lithographic printing plate precursors employing the phosphonium salts represented by formula (2) show better on-press developability than the lithographic printing plate precursors employing the other phosphonium salts.

Example 14 and Comparative Example 3

In Example 14, the same procedure as in Comparative Example 2 was conducted, except that the fountain solution was replaced by one obtained by diluting liquid α shown in the following Table 2 with water to 3% by volume. In Comparative Example 3, the same procedure as in Comparative Example 2 was conducted, except that the fountain solution was replaced by one obtained by diluting liquid β shown in the following Table 2 with water to 3% by volume. The results obtained are shown in Table 3.

TABLE 2

|  | Liquid α | Liquid β |
| --- | --- | --- |
| Pure water | 35.6 | 36.6 |
| Propylene glycol mono-n-butyl ether | 28.4 | 28.4 |
| Propylene glycol | 25 | 25 |
| Octane diol | 4.7 | 4.7 |
| Glycerol | 1 | 1 |
| Maleic acid | 1.9 | 1.9 |
| KOH (48% by mass aqueous solution) | 2.3 | 2.3 |
| Ammonium nitrate | 0.3 | 0.3 |
| Ammonium secondary phosphate | 0.3 | 0.3 |
| Magnesium sulfate | 0.8 | 0.8 |
| Citric acid | 0.2 | 0.2 |
| Ammonium secondary citrate | 0.7 | 0.7 |
| Phosphonium salt (P-8) | 0.1 | 0 |
| 1,2-Benzisothiazol-3(2H)-one | 0.6 | 0.6 |
| Total | 100 | 100 |

TABLE 3

|  | Kind of fountain solution | On-press developability (number of sheets) | Printing durability (number of sheets) |
| --- | --- | --- | --- |
| Example 14 | liquid α | 32 | 7000 |
| Comparative Example 3 | liquid β | 32 | 1000 |

It can be seen from Table 3 that the on-press development type lithographic printing process of the invention employing a fountain solution containing a phosphonium salt attains highly excellent printing durability (ink receptivity) while maintaining on-press developability as compared with the process employing an ordinary fountain solution (Comparative Example 3).

According to the invention, a lithographic printing plate precursor can be provided which gives a lithographic printing plate stably showing ink receptibility during printing and having excellent printing durability. The invention can further provide a lithographic printing plate precursor in which an image can be recorded with a laser and which, after the image recording, can be satisfactorily developed on a printing machine without via a development step to give a printing plate stably showing ink receptibility during printing and having excellent printing durability. The invention can furthermore provide a lithographic printing process which includes image recording with a laser and on-press development and which attains excellent printing durability while maintaining satisfactory on-press developability.

The entire disclosure of each and every foreign patent application from which the benefit of foreign priority has been claimed in the present application is incorporated herein by reference, as if fully set forth.

What is claimed is:

1. A lithographic printing plate precursor, which comprises:
    an aluminum support;
    an image-recording layer comprising a radical polymerization initiator and a radical-polymerizable compound having two or more ethylenically unsaturated double bonds; and
    a protective layer comprising an inorganic layer compound, in this order,
    wherein at least one of the image-recording layer and the protective layer comprises a phosphonium salt represented by formula (1):

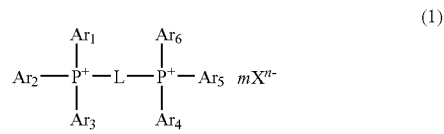

wherein $Ar_1$ to $Ar_6$ each independently represents an aryl group or a heterocyclic group;
L is selected from the group consisting of:

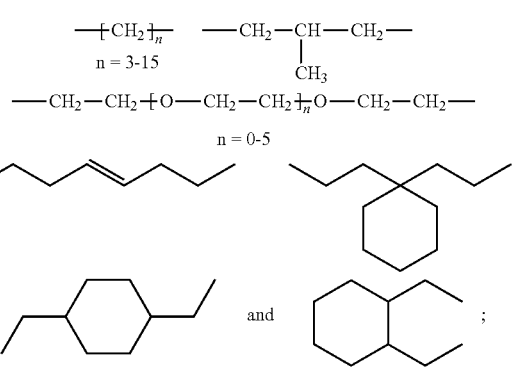

X represents a counter anion having a valence of n;
n represents an integer of from 1 to 3; and
m is a number satisfying n×m=2.

2. A lithographic printing plate precursor, which comprises:
    a support;
    an image-recording layer; and
    a protective layer, in this order,
    wherein at least one of the image-recording layer and the protective layer comprises a phosphonium salt represented by formula (2):

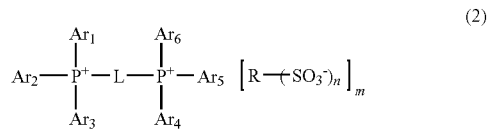

wherein $Ar_1$ to $Ar_6$ each independently represents an aryl group having from 6 to 15 carbon atoms;

L represents a divalent connecting group;

R represents an alkyl group, an aryl group, a heterocyclic group, an alkoxy group, an alkylamino group or an arylamino group;

n represents an integer of from 1 to 3; and m is a number satisfying n×m=2.

3. The lithographic printing plate precursor according to claim 1, wherein the image-recording layer further comprises an infrared absorber.

4. The lithographic printing plate precursor according to claim 1, which can be developed on a printing machine after imagewise exposure.

5. A lithographic printing process, which comprises:

imagewise exposing a lithographic printing plate precursor according to claim 4;

mounting the printing plate precursor on a printing machine without via a development step; and conducting printing, or mounting a lithographic printing plate precursor according to claim 4 on a printing machine; then imagewise exposing the printing plate precursor; and conducting printing.

6. The lithographic printing plate precursor according to claim 2, wherein the image-recording layer further comprises an infrared absorber.

7. The lithographic printing plate precursor according to claim 2, wherein the image-recording layer further comprises a radical polymerization initiator and a radical-polymerizable compound.

8. The lithographic printing plate precursor according to claim 2, wherein the protective layer further comprises an inorganic layer compound.

9. The lithographic printing plate precursor according to claim 2, which can be developed on a printing machine after imagewise exposure.

10. A lithographic printing process, which comprises:

imagewise exposing a lithographic printing plate precursor according to claim 9;

mounting the printing plate precursor on a printing machine without via a development step; and conducting printing, or mounting a lithographic printing plate precursor according to claim 9 on a printing machine; then imagewise exposing the printing plate precursor; and conducting printing.

11. The lithographic printing plate precursor according to claim 1, wherein inorganic layer compound has a particle diameter of 0.3-20 μm.

12. The lithographic printing plate precursor according to claim 1, wherein $mX^{n-}$ is $2PF_6^-$ or $2BF_4^-$.

13. The lithographic printing plate precursor according to claim 1, wherein L is selected from the group consisting of:

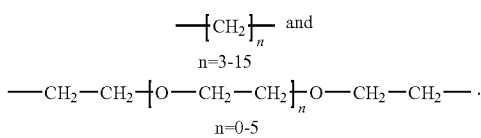

* * * * *